US007645455B2

(12) United States Patent
Jacob et al.

(10) Patent No.: US 7,645,455 B2
(45) Date of Patent: *Jan. 12, 2010

(54) CHIMERIC LYSSAVIRUS NUCLEIC ACIDS AND POLYPEPTIDES

(75) Inventors: Yves Jacob, Maintenon (FR); Pierre Perrin, Montrouge (FR); Noël Tordo, Paris (FR); Chokri Bahloul, Bards (TN)

(73) Assignee: Institut Pasteur, Paris (FR)

( * ) Notice: Subject to any disclaimer, the term of this patent is extended or adjusted under 35 U.S.C. 154(b) by 264 days.

This patent is subject to a terminal disclaimer.

(21) Appl. No.: 11/723,761

(22) Filed: Mar. 22, 2007

(65) Prior Publication Data

US 2008/0206282 A1    Aug. 28, 2008

Related U.S. Application Data

(63) Continuation of application No. 10/608,538, filed on Jun. 30, 2003, now Pat. No. 7,235,245, which is a continuation of application No. 09/549,519, filed on Apr. 14, 2000, now Pat. No. 6,673,601.

(60) Provisional application No. 60/129,501, filed on Apr. 15, 1999.

(51) Int. Cl.
    *A61K 39/205*   (2006.01)
    *A61K 39/295*   (2006.01)
    *C12N 15/47*    (2006.01)

(52) U.S. Cl. .............. 424/224.1; 424/202.1; 424/192.1; 435/320.1

(58) Field of Classification Search ............... 424/224.1
See application file for complete search history.

(56) References Cited

U.S. PATENT DOCUMENTS 6,673,601 B1    1/2004    Jacob et al.

FOREIGN PATENT DOCUMENTS

| EP | 696 191 B1 | 2/1996 |
| WO | WO 90 11092 | 10/1990 |
| WO | WO 93 06223 | 4/1993 |
| WO | WO 95 09249 | 4/1995 |

OTHER PUBLICATIONS

U.S. Appl. No. 09/958,672, filed Jul. 12, 2004, Jacob et al.
Amengual, B. et al., "Evolution of European Bat Lyssaviruses", *J. Gen. Virol.*, 78:2319-2328 (1997).
Bahloul, C. et al., "DNA-based Immunization for Exploring the Enlargement of Immunological Cross-reactivity Against the Lyssaviruses", *Vaccine*, 16:417-425 (1998).
Benmansour et al., "Antigenicity of Rabies Virus Glycoprotein", *J. Virol.*, 65(8):4198-4203 (1991).
Buffett et al., "*P. Falciparum* Domain Mediating Adhesion to Chondroitin Sulfate A: A Receptor for Human Placental Infection", *PNAS*, 96(22):12743-48 (1999).
Coulon et al., "An Avirulent Mutant of Rabies Virus is Unable to Infect Motoneurons In Vivo and In Vitro", *J. Virol.*, 72(1):273-278 (1998).
Desméziéres et al.; Lyssavirus glycoproteins expressing immunologically potent foreign B cell and cytotoxic T lymphocyte epitopes as prototypes for multivalent vaccines; J. Gen. Virol. (1999), 80:2343-2351.
Dietzschold et al., "Structural and Immunological Characterization of a Linear Virus-Neutralizing Epitope of the Rabies Virus Glycoprotein and its Possible Use in a Synthetic Vaccine", *Vaccine*, 64(8):3804-3809 (1990).
Donnelly, J. et al., "DNA Vaccines", *Annu. Rev. Immunol.*, 15:617-648 (1997).
Editorial, Vaccine, vol. 14, pp. 579-732 (1996).
Ertl., et al., "Novel Vaccine Approaches", *Journal of Immunology*, 156:3579-3582 (1996).
European Commission COST/STD-3, "Advantages of Combined Vaccines", *Vaccine*, 14(7):693-700 (1996).
Gaudin, Y., et al., "Reversible Conformational Changes and Fusion Activity of Rabies Virus Glycoprotein", *J. Virol.*, 65(9):4853-4859 (1991).
Gaudin, Y. et al., "Biological Function of the Low-pH, Fusion-inactive Conformation of Rabies Virus Glycoprotein (G): G is Transported in a Fusion-inactive State-like Conformation", *J. Virol.*, 69(9):5528-5533 (1995).
Gaudin, Y., "Folding of Rabies Virus Glycoprotein: Epitope Acquisition and Interaction with Endoplasmic reticulum Chaperones", *J. Virol.*, 71(15):3742-3750 (1997).
Jallet et al., "Chimeric Lyssavirus Glycoproteins with Increased Immunological Potential", *Journal of Virology*, 73(1):225-233 (1999).
Lafay et al., "Immunodominant Epitopes Defined by a Yeast-expressed Library of Random Fragments of the Rabies Virus Glycoprotein Map Outside Major Antigenic Sites", *J.Gen. Virol.*, B77:339-346 (1996).
Lafon et al., "Antigenic Sites on the CVS Rabies Virus Glycoprotein: Analysis with Monoclonal Antibodies", *J. Gen. Virol.*, 64:843-845 (1983).
Lafon, M. et al., "Use of a monoclonal Antibody for Quantitation of Rabies Vaccine Glycoprotein by Enzyme Immunoassay", *J. Biol. Standard*, 13:295-301 (1985).
Lang, J. et al., "Randomised Feasibility Trial of Pre-Exposure Rabies Vaccination with DTP-IPV in Infants", *The Lancet*, 349:1663-1665 (1997).

(Continued)

*Primary Examiner*—Jeffrey Stucker
*Assistant Examiner*—Bao Qun Li
(74) *Attorney, Agent, or Firm*—Finnegan, Henderson, Farabow, Garrett & Dunner, L.L.P.

(57) ABSTRACT

The present invention provides chimeric nucleic acids, preferably contained on an expression vector, that encode chimeric immunogenic polypeptides. The nucleic acids encode at least site III of a lyssavirus glycoprotein, which has been found to improve the immunogenicity of lyssavirus epitopes for protection from rabies. The chimeric nucleic acids and proteins can also contain antigenic determinants for epitopes other than those of lyssavirus. Thus, the invention provides chimeric nucleic acids and polypeptides that elicit a strong immune response to multiple antigens. Use of the methods of the present invention permits DNA vaccination without the need to supply multiple antigens on separate DNA molecules.

6 Claims, 23 Drawing Sheets

OTHER PUBLICATIONS

Liu et al., "Polynucleotide Vaccines:A Potential New Generation of Vaccines," *Proc. Eur. Assoc. Vet. Pharmacol. Toxicol. 6 Meet.*, 301, Abstract Only (1994).

Lodmell, D. et al., "DNA Immunization Protects Nonhuman Primates Against Rabies Virus", *Nature Med.*, 4(8):949-952 (1998a).

Lodmell, D. et al., "Gene Gun Particle-Mediated Vaccination with Plasmid DNA Confers Protective Immunity Against Rabies Virus Infection", *Vaccine*, 16(2/3):115-118 (1998b).

MacFarlan, R. et al., "T Cell Responses to Cleaved Rabies Glycoprotein and to Synthetic Peptides", *J. Immunol.*, 133(5):2748-2752 (1984).

Macy et al., *Vet. Clin. North Am small Anim. Pract.*, Abstract Only, 26(1):103-109 (1996).

Mebatsion et al., "Mokola Virus Glycoprotein and Chimeric Proteins Can Replace Rabies Virus Glycoprotein in the Rescue of Infectious Defective Rabies Virus Particles", *Journal of Virology*, 69(3):1444-1451 (1995).

Paoletti et al., *PNAS*, 93(21):11349-53 (1996).

Pastoret, P-P. et al., "Vaccination Against Rabies", *In Veterinary Vaccinologyl, Pastoret*, Eds. (Elsevier):616-628 (1997). s.

Perrin, P. et al., "Rabies Immunosome (Subunit Vaccine) Structure and Immunogenicity", *Vaccine*, 3:325-332 (1985).

Perrin, P. et al., "The Influence of the Type of Immunosorbent on Rabies Antibody EIA: Advantages of Purified Glycoprotein over Whole Virus", *J. Biol. Standard*, 14:95-102 (1986).

Perrin, P. et al. Interleukin 2 increases protection against experimental rabies, Immunobiology, vol. 177, pp. 199-209 (1988).

Perrin, P., "Techniques for the Preparation of Rabies Conjugates", *In Laboratory Techniques in Rabies*, 4th Ed. (Eds Meslin, F-X; Kaplan, M. and Koprowski, H.) WHO, Geneva:433-445 (1996a).

Perrin, P. et al., "The Antigen-Specific Cell-Mediated Immune Response in Mice is Suppressed by Infection with Pathogenic Lyssaviruses", *Res. Virol.*, 147:289-299 (1996b).

Rogers, S., et al., Amino acid sequences common to rapidly degraded proteins: The PEST hypothesis, Science, vol. 234, pp. 364-369 (1986).

Smith, J. et al., "A Rapid Fluorescent Focus Inhibition Test (RFFIT) for Determining Virus-Neutralizing Antibody", *In Laboratory Techniques in Rabies*, 4th Ed. (Eds Meslin, F-X; Kaplin, M. and Koprowski, H.) WHO, Geneva:181-189 (1996).

Thomson, S. et al., "Delivery of Multiple CD8 Cytotoxic Cell Epitopes by DNA Vaccination", *J. Immunol.*, 160(4):1717-1723 (1998).

Tine et al., "NYVAC-Pf7:A Poxvirus-vectored, Multiantigen, Multistage Vaccine Candidate for Plasmodium Falciparum Malaria," *Infection and Immunity.*, 64(9):3833-3844 (1996).

Tuffereau et al., "Neuronal Cell Surface Molecules Mediate Specific Binding to Rabies Virus Glycoprotein Expressed by a Recombinant Baculovirus on the Surfaces of Lepidopteran Cells", *J. Virol.*, 722):1085-1091 (1998).

Wunner, W. et al., "Localization of Immunogenic Domains on the Rabies Virus Glycoprotein," *Ann. Inst. Pasteur*, 136E:353-362 (1985).

Xiang, Z. et al., "Vaccination with a Plasmid Vector Carrying the Rabies Virus Glycoprotein Gene Induces Protective Immunity Against rabies Virus", *Virol.*, 199:132-140 (1994).

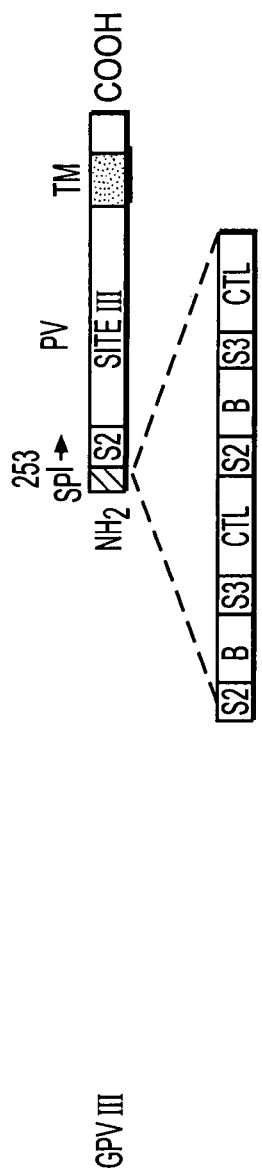
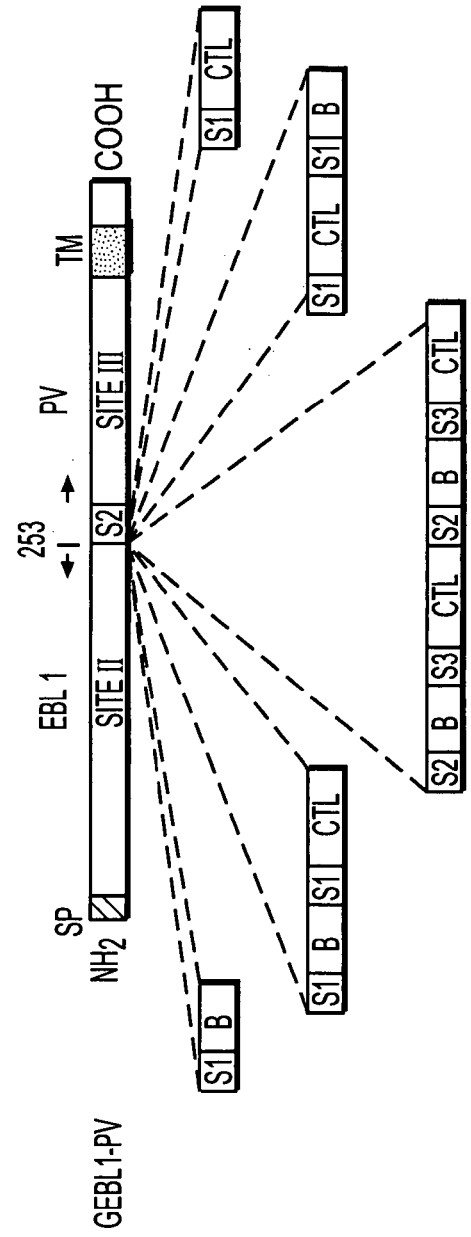

```
                110           130              II   150            170              II   190        IIa
                 .             .                    .               .                    .
PV        d---a----m---------y------k----v-------a-l-p--rs----rv-g-n--vav--ty-s----------rl-m-------n-r--r-s
USA7-BT   d---a-hd-m---------y------k----v-------a-l-p--s-----rv-s--l-itv-ty-s----------ve-rl-t----n-r--r-s
PL        ef--n----v---------y-------------------p--s----------k-t--a-vp-i-s-----l------k--m-------------s
EBL1POL   s----------t-------------k-------------------n-y

FIG. 1E (CONT. 2)

```
            330    III           a    350         III              370              390              410
             .      .             .    .           .                .                .                .
pv         ------f------------------t-n-----rv-----------------------------n----------s-----m---v------ng--
USA7-BT    ------f---i------------kt-n-v---ev-k---pv---------------------n-----------s-----m--------eg--
PL         -----v-----------------------ng-t-n-----vre--py-----------------s------------------m-----------
EBL1POL    ------l-----------------------------------------m---ys-i-------s-g-d------------------m-------yr--i
EBL1FRA    ------l-----------------------------------------m---ys-i-------s-g-d------m-------------------r---
EBL2FIN    ----------------------------t-v-------------------y-h--------s-----------m---------------r---
EBL2HOL    -----v-----------------------tdv------------------y-h--------s-----------m---------------r---
Duv1SAF    -------r-----------e---------k--------------------y-h-i------g-ki-----------m-------------i--g--
Duv2SAF    -------r-----------e---------k--------------------y-h-i------g-ei-----------v-k------n-------s-d--
Lag1NGA    ---------l-qs-iqtnv--lk-dn-s--l----innq-va-de---------------k----i------s-wk--md-fkaa--f------ie-gsl-n--gd-de---d--m--
Lag2CAR    ---------l-qs----tnv--lr-ds-nd-l----mnkq-vdsyr--------------k-h----i------s--k--md--kaa--f------i-qnsl----ga-d---m-
Lag3SAF    ---------l-qs----tnv--lr-ds-nd-l----mnkq-vdsyr--------------k-l----i------s--k--md--kaa--f------i-qnsl---gd
Lag4SAF    ---------l-qs----tnv--lr-ds-nd-l----mnkq-vdsyr--------------k-l----i------s--k--md--kaa--f------i-qnsl---gd
Mok1SAF    ---------l-qs----nvy--r-dr-ad-l----v-qq-mdpv--j-------------k------qi-----eq-k--md--kaa--f------isqea----gd
Mok3ETP    ---------l-qs----tnvy--r-dr-ad-l-r--v-qq-mdpvk--l-----------k------qi-----eq-k--md--kaamf--------inrea----gn-d---dl-m-
Mok2ZIM    ---------l-qs----tnvy--r-dk-ad-l----v-qq-mepvk--l-----------k------qi-----eq-k--md--kaa--f------isrea----gd-d---dl-m-
CONSENS    GKAYTIINKTLMEADAHYKSVREW-ETIPSKGGLKAGGRCHPH-NGVEFNGIILGPDGHVLIPEMQSALLQQHIELLESSVIPLRHPLADPSTVFKKDDEAEDFVEVHLP
```

FIG. 1E (CONT. 3)

```
                        430              450                 470                 490              510
                         .                .                   .                   .                .
PV         --her---v-----n-gk-v-ls-g--ta-m-i-flmt-wr---n-septqh--lrgtg--e----p----i--s-------s-getgl
USA7-BT    --h-r---v-----s-gk-l-ms-g--i-i--vlll--r--nktgstqrghr-srg-m--ap-n--i--s---l--resetgl
PL         ----qv------s-e--li---vi-f-----r-c----kkartdri--d--------------lkpshfrs
EBL1POL    --t--l-------f-----l-v------f-----rp--------t-a----f-----i------ra-----v-pp--es
EBL1FRA    --t--l-------f------------i-v------t-a----sr--rp--------i-----rav------v-tses
EBL2FIN    -----q----------v---------v---m--f---a-----hkkra-------v---------rp--------ve-g--qs
EBL2HOL    -----q----------------------v--f--m-f---a--r---kkra-------v---------rp--------ve-g--qs
Duv1SAF    -tnqk---------v------v---v-----s--mr-------f-n--ks--s--v--t----i-kgngpv------e--t--dvrnttpstre
Duv2SAF    -tnqk---------v------v---v-----s-----------frk--kks--g--v--t----i-kgngpv------e--t--dvrnttpstre
Lag1NGA    --h-lv-dv------d-sl--a----tll--ffl-lcl--rl----krg--nsptnr-dlp-glsttpqpks---s-----gtsnv
Lag2CAR    -i--l--dv------s-gl--vm---avi-f-v-lcl--rl----kkt--t--tsmer-dpp-slsttpqsra--vs-----gssnv
Mok3ETP    -----sv-dv-----h-gfwl-v--tvv-ftvv--cllr----r-mr---slratqdiplsvapapvpra--vs---s-glpgt
Mok2ZIM    --h-sv-dv------h-gfwm----tiv-fvv-vcllr--------r---sgratqeiplsfp--apvpra--vs-----glpgt
CONSENS    DVQK-ISGIDLGLPEWKRYFLIGASALLALALAIIAVCCKRVKRRR--KPNP-ELIRKVSVTSQSGKVIPSWESYK-GT-G

ECTO------>          TM        <------       ENDO
```

*FIG. 1E (CONT. 4)*

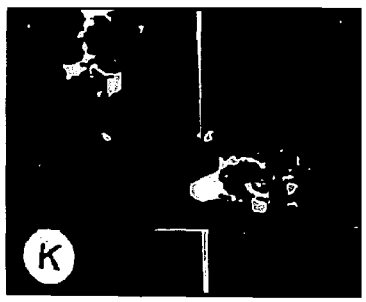
*FIG. 2J*   *FIG. 2K*   *FIG. 2L*
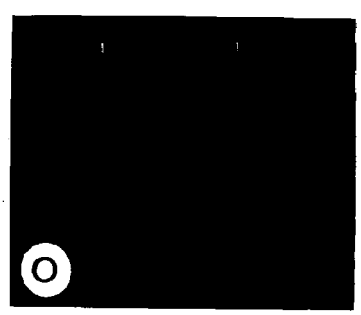
*FIG. 2M*   *FIG. 2N*   *FIG. 2O*

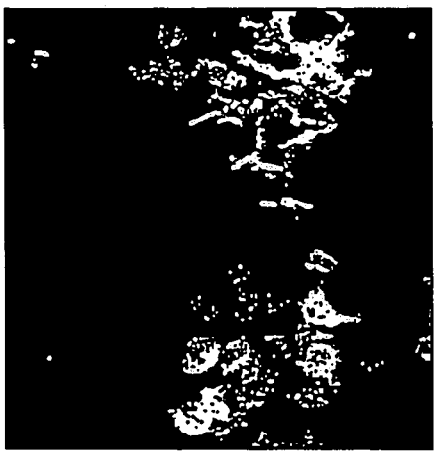
FIG. 13A
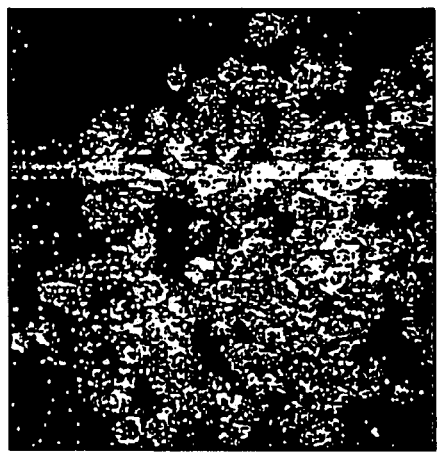
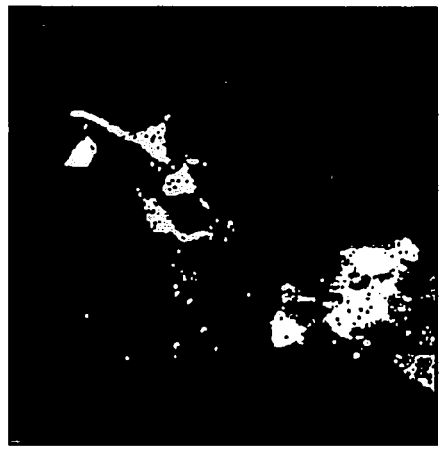
FIG. 13B

CHIMERIC LYSSAVIRUS NUCLEIC ACIDS AND POLYPEPTIDES

CROSS-REFERENCE TO RELATED APPLICATION

This application is a continuation of application Ser. No. 10/608,538, filed Jun. 30, 2003, now U.S. Pat. No. 7,235,245 which is a continuation of application Ser. No. 09/549,519, filed Apr. 14, 2000, now U.S. Pat. No. 6,673,601, and claims the benefit of the filing date of U.S. Provisional Application Ser. No. 60/129,501, filed Apr. 15, 1999, the disclosures of which are all hereby incorporated by reference.

BACKGROUND OF THE INVENTION

1. Field of the Invention

The present invention relates to chimeric lyssavirus nucleic acids, and chimeric polypeptides and proteins encoded by these nucleic acids. More particularly, the invention relates to chimeric lyssavirus nucleic acids and proteins that can be used in immunogenic compositions, such as vaccines. Thus, the invention also relates to carrier molecules for expressing chimeric lyssavirus nucleic acids, methods of producing chimeric lyssavirus proteins and polypeptides, and methods of treating individuals to ameliorate, cure, or protect against lyssavirus infection. The compositions of the invention can also be used to express peptides, polypeptides, or proteins from organisms other than lyssaviruses. Thus, the invention provides methods of treating individuals to ameliorate, cure, or protect against many different infections, diseases, and disorders.

2. Background of the Related Art

Rabies is an encephalopathic disease caused by members of the Lyssavirus genus within the Rhabdoviridae family. Rabies infects all warm-blooded animals and is almost invariably fatal in humans if not treated. On the basis of nucleotide sequence comparisons and phylogenetic analyses, the Lyssavirus genus has been divided into 7 genotypes (GT). GT1 includes the classical rabies viruses and vaccine strains, whereas GT2 to GT7 correspond to rabies-related viruses including Lagos bat virus (GT2); Mokola virus (GT3); Duvenhage virus (GT4); European bat lyssavirus 1 (EBL-1: GT5); European bat lyssavirus 2 (EBL-2: GT6); and Australian bat lyssavirus (GT7).

Based on antigenicity, the Lyssavirus genus was first divided into four serotypes. More recently, this genus was divided into two principal groups according to the cross-reactivity of virus neutralizing antibody (VNAb): Group 1 consists of GT1, GT4, GT5, GT6, and GT7, while Group 2 consists of GT2 and GT3. Viruses of group 2 are not pathogenic when injected peripherally in mice. Virulence of lyssaviruses is dependent, at least in part, on the glycoprotein present in the viral coat. Interestingly, the glycoproteins of group 2 viruses show a high degree of identity, in the region containing amino acids that play a key role in pathogenicity, to the corresponding sequence of avirulent GT1 viruses (see, for example, Coulon et al., 1998, "An avirulent mutant of rabies virus is unable to infect motoneurons in vivo and in vitro", J. Virol. 72:273-278).

Rabies virus glycoprotein (G) is composed of a cytoplasmic domain, a transmembrane domain, and an ectodomain. The glycoprotein is a trimer, with the ectodomains exposed at the virus surface. The ectodomain is involved in the induction of both VNAb production and protection after vaccination, both pre- and post-exposure to the virus. Therefore, much attention has been focused on G in the development of rabies subunit vaccines. Structurally, G contains three regions, the amino-terminal (N-terminal) region, a "hinge" or "linker" region, and the carboxy-terminal (C-terminal) region. (See FIG. 1.)

As depicted in FIG. 1, it is generally thought that the glycoprotein (G) ectodomain has two major antigenic sites, site II and site III, which are recognized by about 72.5% (site II) and 24% (site III) of neutralizing monoclonal antibodies (MAb), respectively. The site II is located in the N-terminal half of the protein and the site III is located in the C-terminal half of the protein. The two halves are separated by a flexible hinge around the linear region (amino acid 253 to 257).

The G ectodomain further contains one minor site (site a), and several epitopes recognized by single MAbs (I: amino acid residue 231 is part of the epitope; V: residue 294 is part of the epitope, and VI: residue 264 is part of the epitope) (Benmansour et al., 1991, "Antigenicity of rabies virus glycoprotein", J. Virol. 65:4198-4203; Dietzschold et al., 1990, "Structural and immunological characterization of a linear virus-neutralizing epitope of the rabies virus glycoprotein and its possible use in a synthetic vaccine", J. Virol. 64:3804-3809; Lafay et al., 1996, "Immunodominant epitopes defined by a yeast-expressed library of random fragments of the rabies virus glycoprotein map outside major antigenic sites", J. Gen. Virol. 77:339-346; Lafon et al., 1983, "Antigenic sites on the CVS rabies virus glycoprotein: analysis with monoclonal antibodies", J. Gen. Virol. 64:843-845). Site II is conformational and discontinuous (amino acid residues 34 to 42 and amino acid residues 198 to 200, which are associated by disulfide bridges), whereas site III is conformational and continuous (residues 330 to 338). Lysine 330 and arginine 333 in site III play a key role in neurovirulence and may be involved in the recognition of neuronal receptors (see, for example, Coulon et al., supra, and Tuffereau et al., 1998, "Neuronal cell surface molecules mediate specific binding to rabies virus glycoprotein expressed by a recombinant baculovirus on the surfaces of lepidopteran cells", J. Virol. 72:1085-1091). Sites II and III seem to be close to one another in the three dimensional structure and exposed at the surface of the protein (Gaudin, Y., 1997, "Folding of rabies virus glycoprotein: epitope acquisition and interaction with endoplasmic reticulum chaperones", J. Virol. 71:3742-3750). However, at low pH, the G molecule takes on a fusion-inactive conformation in which site II is not accessible to MAbs, whereas sites a and III remain more or less exposed (Gaudin, Y. et al., 1995, "Biological function of the low-pH, fusion-inactive on formation of rabies virus glycoprotein (G): G is transported in a fusion-inactive state-like conformation", J. Virol. 69:5528-5533; Gaudin, Y., et al., 1991, "Reversible conformational changes and fusion activity of rabies virus glycoprotein", J. Virol. 65:4853-4859).

Moreover, several regions distributed along the ectodomain are involved in the induction of T helper (Th) cells (MacFarlan, R. et al., 1984, "T cell responses to cleaved rabies virus glycoprotein and to synthetic peptides", J. Immunol. 133:2748-2752; Wunner, W. et al, 1985, "Localization of immunogenic domains on the rabies virus glycoprotein", Ann. Inst. Pasteur, 136 E:353-362). Based on these structural and immunological properties, it has been suggested that the G molecule may contain two immunologically active parts, each potentially able to induce both VNAb and Th cells (Bahloul, C. et al, 1998, "DNA-based immunization for exploring the enlargement of immunological cross-reactivity against the lyssaviruses", Vaccine 16:417-425).

Currently available vaccines predominantly consist of, or are derived from, GT1 viruses, against which they give protection. Many vaccine strains are not effective against GT4, and none are effective against GT2 or GT3. However, the protection elicited against GT4 through 6 depends on the vaccine strain. For example, protection from the European bat lyssaviruses (GT5 and GT6), the isolation of which has become more frequent in recent years, by rabies vaccine strain PM (Pitman-Moore) is not robust. Strain PM induces a weaker protection against EBL1 (GT5) than the protection it provides against strain PV (Pasteur virus).

Because, in part, of the importance of rabies in world health, there is a continuing need to provide safe, effective, fast-acting vaccines and immunogenic compositions to treat and prevent this disease. Many approaches other than use of whole-virus preparations have been proposed and/or pursued to provide an effective, cost-efficient immunogenic composition specific for rabies viruses. For example, as discussed above, subunit vaccines have been developed. Also, vaccines that could generate an immune response to multiple rabies serotypes as well as various other pathogens has been proposed as having some value (European Commission COST/STD-3, 1996, "Advantages of combined vaccines", *Vaccine* 14:693-700). In fact, use of a combined vaccine of diphtheria, tetanus, whole cell pertussis, inactivated poliomyelitis, and rabies has recently been reported (Lang, J. et al., 1997, "Randomised Feasibility trial of pre-exposure rabies vaccination with DTP-IPV in infants", *The Lancet* 349:1663-1665). Combined vaccines including rabies have also been used for immunization of dogs (distemper, hepatitis, leptospirosis, and parvo-canine viruses), cats (panleukopenia, calici- and parvo-feline viruses), and cattle (foot and mouth disease virus) (Pastoret, P-P. et al., 1997, "Vaccination against rabies", In *Veterinary Vaccinology*, Pastoret, P-P. et al., Eds. (Elsevier): 616-628).

Moreover, vaccines produced in tissue culture are expensive to produce despite some attempts to reduce their cost. Consequently DNA vaccines, which are less expensive to produce and offer many advantages, would constitute a valuable alternative. Reports of DNA vaccinations include mouse inoculation with plasmids containing the gene encoding the rabies virus glycoprotein (G). Such inoculation is very potent in inducing humoral and cellular immune responses in association with protection against an intracerebral challenge (see, for example, Lodmell, D. et al., 1998, "DNA immunization protects nonhuman primates against rabies virus", *Science Med.* 4:949-952; Xiang, Z. et al., 1994, "Vaccination with a plasmid vector carrying the rabies virus glycoprotein gene induces protective immunity against rabies virus", *Virol.* 199:132-140; and Lodmell, D. et al., 1998, "Gene gun particle-mediated vaccination with plasmid DNA confers protective immunity against rabies virus infection", *Vaccine* 16, 115). DNA immunization can also protect nonhuman primates against rabies (Lodmell et al, 1998, supra).

Because administration of plasmid DNA generates humoral and cellular immune responses, including cytotoxic T-Lymphocyte (CTL) production (for review see Donnelly, J. et al., 1997, "DNA Vaccines", *Annu. Rev. Immunol.* 15:617-648) and is based on a versatile technology, immunization with plasmid DNA may offer a satisfying prospect for multivalent vaccines. However, the use of a mixture of plasmids or a single plasmid expressing several antigens is believed to induce interference problems at both transcriptional and immunological levels (Thomson, S. et al., 1998, "Delivery of multiple CD8 cytotoxic cell epitopes by DNA vaccination", *J. Immunol.* 160: 1717-1723). Therefore, there exists a need to develop and produce multivalent DNA-based vaccines that are effective against rabies and various other diseases; that are safe; and that are cost-efficient to produce and use.

BRIEF DESCRIPTION OF THE INVENTION

The present invention provides chimeric nucleic acid sequences that encode chimeric polypeptides that induce immunogenic responses in individuals (animals and humans). The nucleic acids of the invention can be expressed to provide chimeric polypeptides that elicit an immune response against rabies and/or rabies-related viruses as well as other pathogenic or otherwise undesirable organisms or polypeptides. Further, the nucleic acids of the invention themselves can elicit at least a portion of the immune response. Thus, the chimeric nucleic acids of the invention can be used to make an immunogenic composition, which can be used to treat an individual.

The present invention also provides a carrier molecule, such as a DNA expression vector, comprising the nucleic acid of the invention, which encodes a chimeric polypeptide. The carrier molecule of the invention can be used as an immunogenic composition, or as part of an immunogenic composition, to elicit the desired immune response. The desired immune response can be a protective response to rabies or rabies-related viruses as well as other organisms or polypeptides. Thus, the carrier molecules of the invention can be used to make an immunogenic composition, which can be used to treat an individual. The carrier molecule can also be used to produce a chimeric polypeptide.

The present invention thus provides a chimeric (fusion) protein that is encoded by the nucleic acid of the invention, or by a nucleic acid sequence present in the carrier molecule of the invention. The chimeric protein can be used to elicit an immunogenic response in an individual. The fusion protein comprises the site III antigenic determinant of a lyssavirus glycoprotein, and can comprise other antigenic sites from one or multiple other polypeptides. Thus, the chimeric polypeptide of the invention can be used to make an immunogenic composition, which can be used to treat an individual.

The present invention further provides immunogenic compositions, including vaccines, that elicit an immunological response in individuals to whom they are administered. The present invention includes immunogenic compositions comprising a polynucleotide sequence that encodes a chimeric (or fusion) polypeptide, or the chimeric polypeptide so encoded, which elicits the immune response. The immunogenic compositions and vaccines of the present invention provide an increased level of immune stimulation and enhanced protection against rabies viruses, and broaden the spectrum of protection against rabies-related viruses, as compared to immunogenic compositions known in the art. The immunogenic compositions also provide multiple immunogenic active sites for induction of an immune response against rabies epitopes as well as epitopes unrelated to rabies.

In view of the above embodiments of the invention, it is evident that the present invention also provides a method of producing a chimeric nucleic acid, a method of producing a carrier molecule, a method of producing a fusion protein, and a method of making an immunogenic composition, such as a vaccine. The immunogenic composition so made can be used to treat (e.g., immunize) individuals.

Included in the invention is the use of the nucleic acid, polypeptide, and/or carrier molecule of the invention to elicit an immune response, such as a protective immune response. Thus, the invention includes the use of a vaccine comprising the polynucleotide, polypeptide, and/or carrier molecule of the invention to treat an individual, either prophylactically or therapeutically. Therefore, the invention includes prophylactic treatment methods, therapeutic treatment methods, and curative treatment methods.

BRIEF DESCRIPTION OF THE DRAWINGS

The invention will be described in greater detail with reference to the drawings, in which:

FIG. 1 depicts lyssavirus glycoproteins and chimeric constructs of lyssavirus glycoproteins. SP—Signal peptide; TM—Transmembrane domain; $S_1$—NL amino acid residues; $S_2$—NS amino acid residues; $S_3$—LFAV amino acid residues.

Figure 2A:
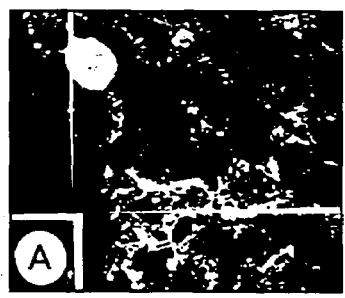
Figure 2B:

(A) A schematic representation of lyssavirus PV glycoprotein (G) is presented at the top, indicating regions encompassing site II, site III, and epitopes I, V, and VI, as well as the transmembrane domain (TM). Chimeric polypeptides are schematically depicted on the other lines, with deletion and/or fusion points indicated by residue numbers. Numbers are the positions of amino acid residues on the mature protein (signal peptide cleaved).

(B) Amino acid sequences of the chimeric polypeptides at the fusion sites, PV-PV (SEQ ID NO: 18); -PVIII (SEQ ID NO: 19); ELB1-PV (SEQ ID NO: 20); MoK-PV (SEQ ID NO: 21); PV-MoK (SEQ ID NO: 22); MoK-Sad (SEQ ID NO: 23). The linear region carrying epitope VI (amino acid 264) is indicated by underlining at residues 251-275. Black and gray boxes outline the EBL-1 and Mok sequences, respectively. Dashes represent amino acids similar to those of the PV sequence, and dots represent gaps.

(C) Schematic representation of the inserted sequences encoding the C3 poliovirus epitope involved in virus neutralizing antibody induction (B), and lymphocytic choriomeningitis virus (LCMV) nucleoprotein CD8 H-$2^d$ (CTL) cell epitope involved in the induction of both cytotoxic T Lymphocytes (CTL) and protection against LCMV challenge in the truncated (GPVIII) and chimeric lyssavirus G protein (GEBL1-PV).

(D) Putative PEST sequence analysis around the junction of the end of EBL1 part and the beginning of B cell epitope is also reported.

(E) Comparison of the deduced amino acid sequences of G proteins of selected lyssaviruses, PV (SEQ ID NO: 24); USA7-BT (SEQ ID NO: 25); P1 (SEQ ID NO: 26); EBLIPOL (SEQ ID NO: 27); EBLIFRA (SEQ ID NO: 28); EBL2FIN (SEQ ID NO: 29); EBL2HOL (SEQ ID NO: 30); Duv1SAF (SEQ ID NO: 31); Duv2SAF (SEQ ID NO: 32); Lag1NGA (SEQ ID NO: 33); Lag2CAR (SEQ ID NO: 34); Mok3ETP (SEQ ID NO: 35); Mok2ZIM (SEQ ID NO: 36). The consensus sequence is presented as the bottom sequence. Light grey boxes indicate the main antigenic sites. Dark grey boxes indicate the hydrophobic signal peptide (SP) and the transmembrane domain (TM). Underlined NX(S/T) motifs are potential N-glycosylation sites.

FIG. 2 shows indirect immunofluorescence microscopy of lyssavirus G production in Neuro-2a cells 48 h after transient transfection with various plasmids: pGPV-PV (A, B and C), pG-PVIII (D, E and F), pGEBL1-PV (G, H, and I), pGMok-PV (J, K, and L), and pGPV-Mok (M, N, and O). Forty-eight hours after transfection, cells were permeabilized and stained with antibodies: anti-PV G PAb (A, D, G, J, and M), PV D1 anti-native PV G site III MAb (B, E, H, and K), 6B1 anti-denatured G site III MAb (C and F), anti-EBL-1 G PAb (I), anti-Mok G PAb (L and N) and serum from an unimmunized mouse (O).

FIG. 3 shows the results of a kinetic study of antigen synthesis in Neuro-2a cells transiently transfected with pGPV-PV (A), pGEBL1-PV (B), or pG-PVIII (C). Cells were permeabilized at various times and stained with PV PAb (white bar) or anti-denatured G site III 6B1 MAb (black bar).

Figure 4:
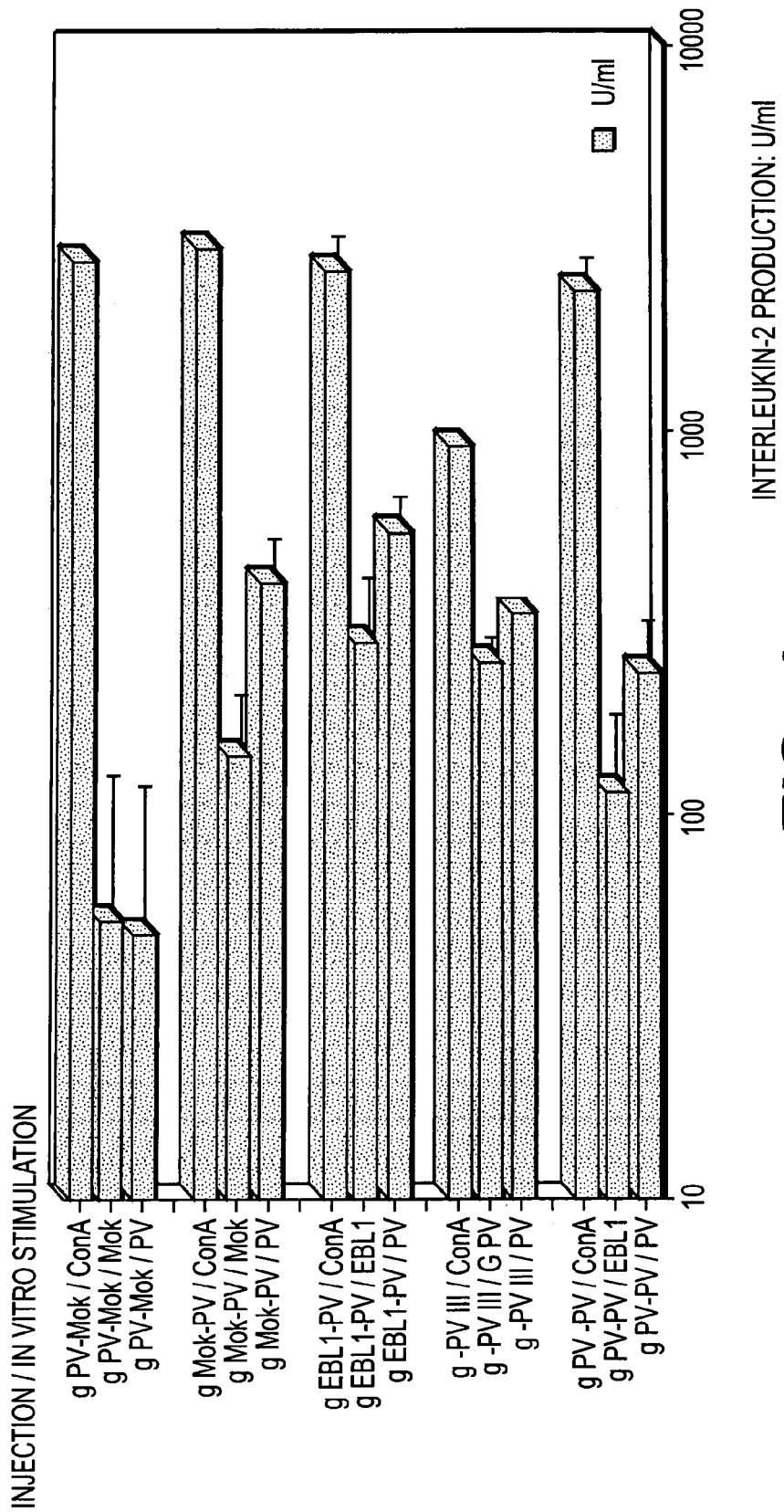

FIG. 4 shows the results of induction of IL-2-producing cells by plasmids encoding various lyssavirus G. BALB/c mice (two animals for each plasmids) were injected i.m. (50 µl in each anterior tibialis muscle) with 40 µg plasmid (pGPV-PV, pG-PVIII, pGEBL1-PV, pGMok-PV and pGPV-Mok). Spleens were removed 21 days later and splenocytes were specifically stimulated in vitro by inactivated and purified viruses (PV, EBL1 or Mok), G PV, or polyclonally stimulated by concanavalin A (ConA). The amount of IL-2 released was then assayed in triplicates by bioassay and titers expressed as U/ml.

FIG. 5 shows induction of VNAb against European lyssavirus genotypes by plasmid. BALB/c mice were injected with 40 µg plasmid in the tibialis muscle.

(A) Injection with pGPV-PV. Mice received a boost on day 30. Sera (pool of 3 samples) were assayed on days 27 and 40 for VNAb against viruses of genotypes 1 (CVS and PV), 5 (EBL1b), and 6 (EBL2b).

(B) Injection with pGEBL1-PV. Four mice received only one injection of plasmid and blood samples were collected at various intervals by trans-orbital puncture. Sera were assayed by RFFIT using PV and EBL1b viruses for VNAb determination.

FIG. 6 shows comparative protection induced by pGPV-PV, pGEBL1-PV plasmids, and rabies PM and PV vaccines against CVS, EBL-1b, and EBL-2b. BALB/c mice (9 animals per series) were injected i.p. on days 0 and 7 with 0.5 ml of PM vaccine diluted 1/10th (solid circles) or with 2 µg of inactivated and purified PV virus (solid squares). For DNA-based immunizations, BALB/c mice (5 animals for each plasmid) were injected in the tibialis muscle with PBS (open circles) or with 40 µg of various plasmids pGPV-PV (diamond), EBL1-PV (solid triangle), pCIneo backbone (cross). Swiss mice (6 animals) were injected with pGPV-PV (open square).

(a) Inactivated virus was injected. BALB/c and Swiss mice were challenged i.c. on day 21 with about 30 $LD_{50}$ of CVS.

(b) Inactivated virus was injected. BALB/c and Swiss mice were challenged i.c. on day 21 with about 30 $LD_{50}$ of EBL-1b.

(c) Inactivated virus was injected. BALB/c and Swiss mice were challenged i.c. on day 21 with about 30 $LD_{50}$ of EBL-2b.

(d) DNA was injected. BALB/c and Swiss mice were challenged i.c. on day 21 with about 30 $LD_{50}$ of CVS.

(e) DNA was injected. BALB/c and Swiss mice were challenged i.c. on day 21 with about 30 $LD_{50}$ of EBL-1b.

(f) DNA was injected. BALB/c and Swiss mice were challenged i.c. on day 21 with about 30 $LD_{50}$ of EBL-2b.

FIG. 7 shows indirect immunofluorescence microscopy of antigens expressed in Neuro-2a cells transfected with plasmids.

(A) Cells were transfected with plasmid pGEBL1-(B-CTL)$_2$-PV and stained with the rabies D1 MAb.

(B) Cells were transfected with plasmid pGEBL1-(B-CTL)$_2$-PV and stained with the poliovirus C3 MAb.

(C) Cells were transfected with plasmid pGEBL1-(B-CTL)$_2$-PV and stained with the anti-poliovirus type 1 PAb.

(D) Cells were transfected with plasmid pCIneo and stained with either 1) the rabies D1 MAb, 2) the poliovirus C3 MAb, or 3) the anti-poliovirus type 1 PAb.

FIG. 8 shows induction of IL-2-producing cells by pGPVIII (A) or pGEBL1-PV (B) carrying poliovirus and LCMV epitopes. BALB/c mice (two animals for each plasmids) were injected i.m. (50 µg in each anterior tibialis muscle) with plasmids. Spleens were removed 14 days later and splenocytes were stimulated in vitro by cell culture medium (solid bar) specifically by inactivated and purified lyssaviruses (IPLV PV: hashed bar; IPLV EBL: brick) or polyclonally stimulated by ConA (open bar). The amount of IL-2 released was then assayed in triplicates by bioassay and titers expressed as U/ml.

(A) Plasmids injected were pCIneo-empty plasmid-, pGPVIII, and p(B-CTL)$_2$-GPVIII.

(B) Plasmids injected were pCIneo, pGEBL1-PV, pGEBL1-(B)-PV, pGEBL1-(CTL)-PV, pGEBL1-(CTL-B)-PV, pGEBL1-(B-CTL)$_2$-PV.

Figure 9:
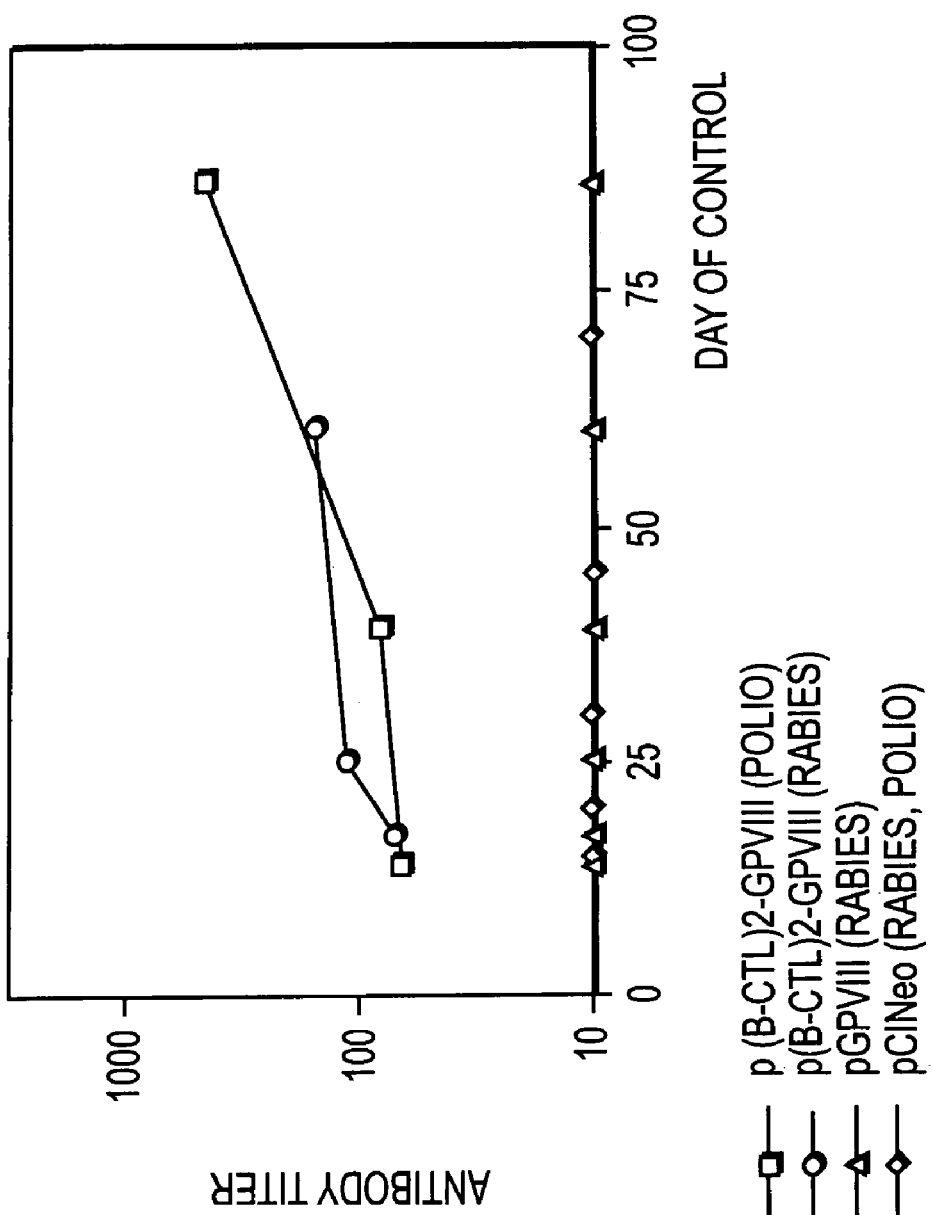

FIG. 9 shows a kinetic study in BALB/c mice of antibody production induced by p(B-CTL)2-GPVIII or pGPVIII against poliovirus peptide and rabies virus. Three mice were injected with 40 μg of p(B-CTL)2-GPVIII (square and circle), or pGPVIII (triangle), or empty pCIneo (diamond). After puncture by retro-orbital route at various times, sera were assayed by ELISA for the determination of antibody against poliovirus peptide (square and diamond) or rabies virus (circle, triangle and diamond).

Figure 10:
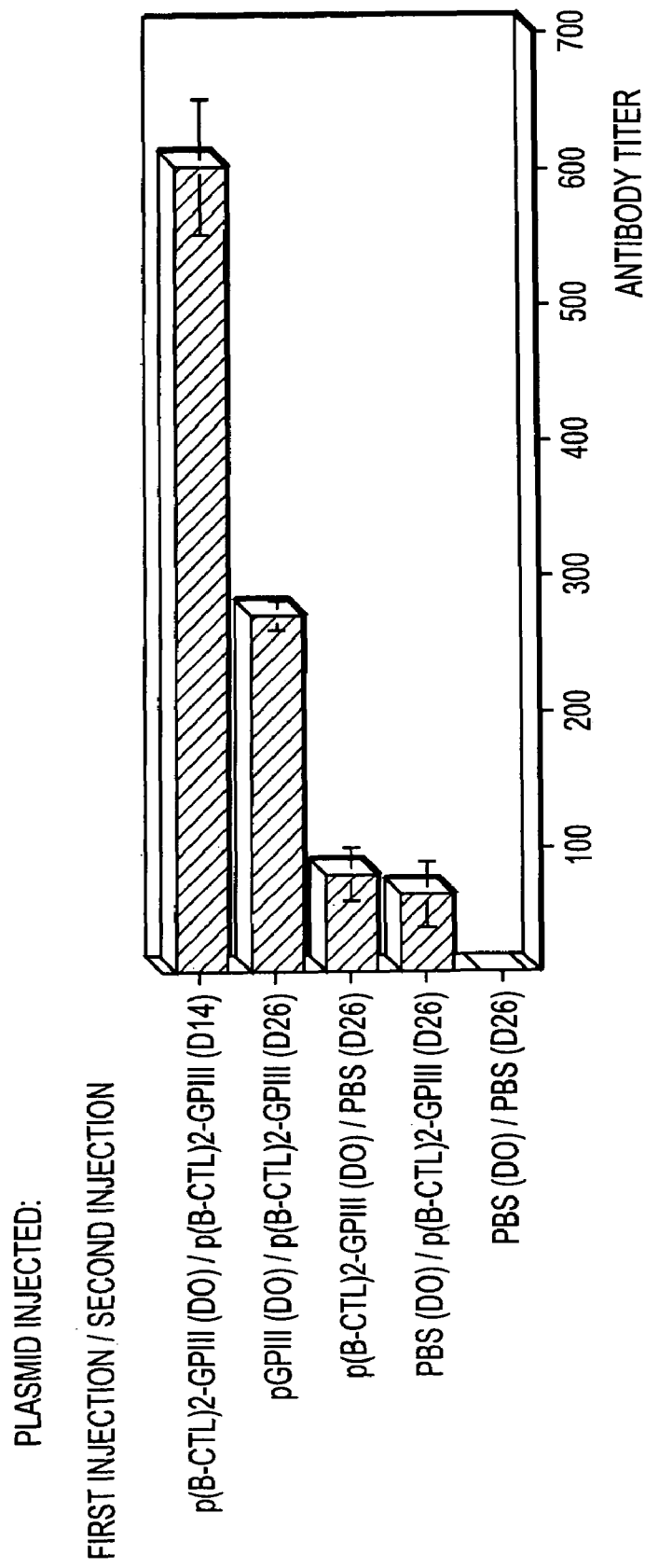

FIG. 10 shows the influence of a priming on the poliovirus anti-peptide antibody production induced by p(B-CTL)2-GPVIII. Five groups of three mice received on day 0 PBS (2 groups), p(B-CTL)2-GPVIII (2 groups), or pPVIII. One group (injected with p(B-CTL)2-GPVIII) was not boosted, whereas the group injected with pPVIII was boosted with p(B-CTL)2-GPVIII on day 26. One group (injected with p(B-CTL)2-GPVIII) was boosted with p(B-CTL)2-GPVIII on day 14. All animals were controlled for anti-peptide antibody production on day 39 by ELISA.

Figure 11:
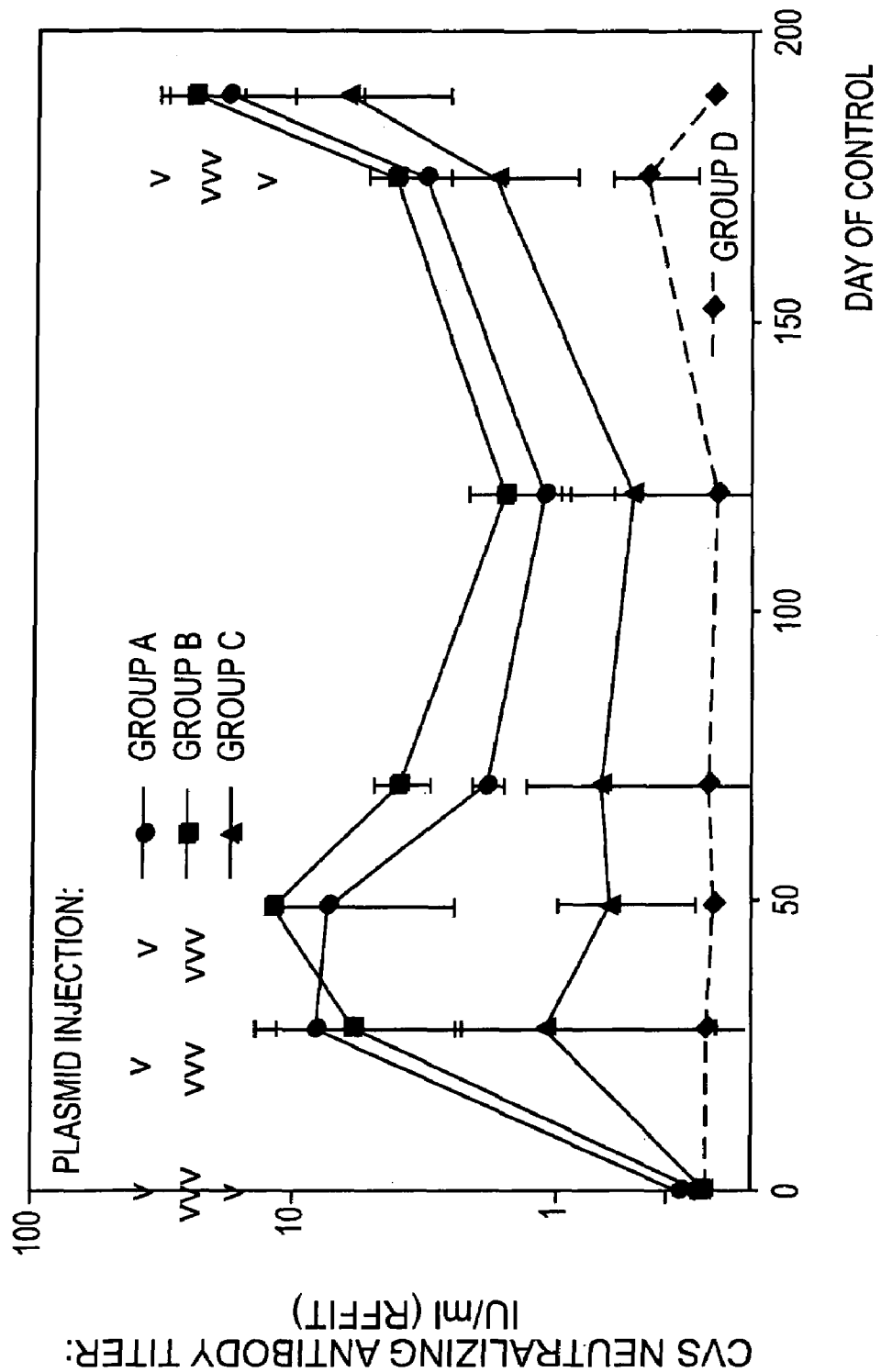

FIG. 11 shows the production of rabies virus neutralizing antibodies against the challenge virus standard (EVS) after injection of the full homogeneous plasmid pGPV in beagle dogs.

Group A: Injection of 100 μg of plasmid in one site on days, 0, 21, 42, and 175.

Group B: Injection of 33 μg of plasmid in three sites on days 0, 21, 42, and 175.

Group C: Injection of 100 μg of plasmid in one site on days 0 and 175.

Group D: Injection of phosphate buffered saline (control).

Figure 12:
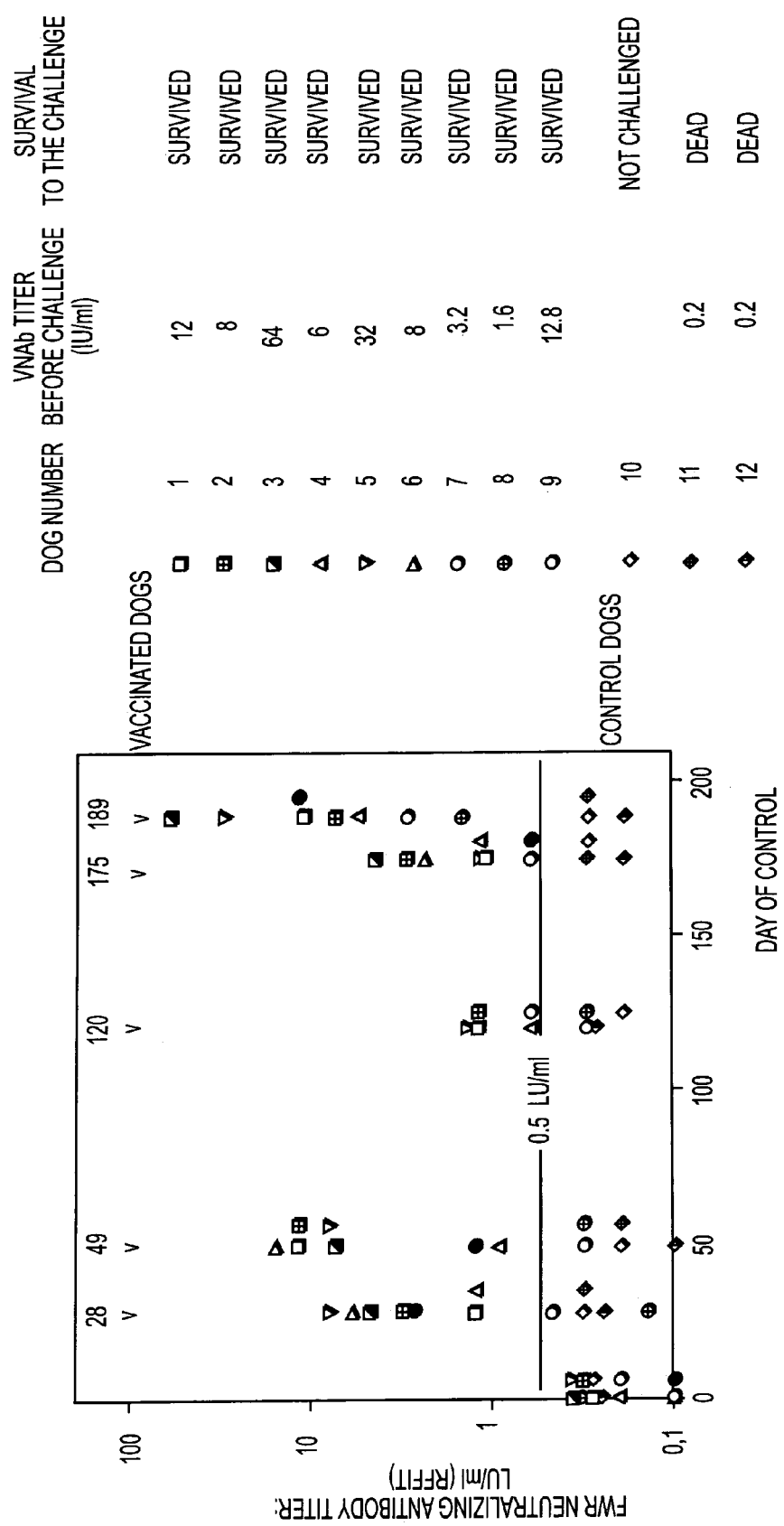

FIG. 12 shows individual neutralizing antibody response against a wild rabies virus (fox from France, fox wild rabies virus FWR) after injection of the full homogeneous plasmid pGPV in beagle dogs. It shows also the protection induced against an intramuscular challenge performed on day 175 with a wild rabies virus isolated from rabid dogs.

| | |
|---|---|
| Dogs nos. 1 to 3 = | group A |
| Dogs nos. 4 to 6 = | group B |
| Dogs nos. 7 to 9 = | group C |
| Dogs nos. 10 to 12 = | group D |

FIG. 13 shows the results of indirect immunofluorescence of N$_2$A cells transfected with plasmid DBL-3/PVIII (Fugene, Roche Molecular Biochemicals) and fixed with acetone (80%) for 10 minutes on ice.

(A) Results of mouse anti-DBL-3 GTST fusion protein (1/1000 dilution) are shown in the top panel. Background reactivity seen with the second antibody (anti-mouse) conjugated to FITC is shown in the bottom panel.

(B) Results of rabbit anti-PVIII (1/400 dilution) are shown in the top panel. Background reactivity seen with the second antibody (anti-rabbit) conjugated to FITC is shown in the bottom panel.

DETAILED DESCRIPTION OF PREFERRED EMBODIMENTS

The inventors have created chimeric nucleic acid sequences that encode chimeric polypeptides that induce immunogenic responses in individuals. As discussed above, it is known in the art that nucleic acids can elicit both humoral and cellular immune responses. In doing so, it is possible for the nucleic acids not only to indirectly induce an immune response via an encoded peptide, polypeptide, or protein, but for the nucleic acids to directly induce an immune response. Thus, the nucleic acids of the invention can themselves induce at least part of the immunogenic response. Accordingly, according to the invention, the chimeric nucleic acids and carrier molecules can directly or indirectly provide or promote an immunogenic response when used according to the invention.

As used herein, "chimeric" and "fusion" are used interchangeably and in reference to both nucleic acids and polypeptides. These terms refer to nucleic acids and polypeptides that comprise sequences that are not found naturally associated with each other in the order or context in which they are placed according to the invention. For example, a chimeric glycoprotein can comprise a C-terminal region from a rabies GT1 and an N-terminal region from a rabies GT3 or GT5. Further, a chimeric nucleic acid can comprise a short segment from one portion of a rabies genotype linked directly to another segment from the same genotype, where the two segments are not naturally adjacent each other. Thus, a chimeric or fusion nucleic acid or polypeptide does not comprise the natural sequence of a rabies virus in its entirety, and may comprise heterologous (from another strain of lyssavirus, or from another organism altogether) sequences. Fusion/chimeric proteins have the two (or more) segments joined together through normal peptide bonds, while fusion/chimeric nucleic acids have the two (or more) segments joined together through normal phosphodiester bonds.

In one aspect of the invention, the chimeric nucleic acids comprise a) a sequence encoding site III of a glycoprotein, b) a sequence encoding the transmembrane domain (or a portion thereof that is functionally equivalent to the transmembrane domain) of a glycoprotein, and c) a sequence that encodes the cytoplasmic domain of the glycoprotein of a lyssavirus. In preferred embodiments of this aspect of the invention, the chimeric nucleic acids further comprise a sequence encoding site II of a lyssavirus glycoprotein. In embodiments, the sequence encoding the transmembrane domain (or portion thereof) is a sequence from a transmembrane glycoprotein of a lyssavirus. In other embodiments, the sequence is from a transmembrane glycoprotein other than a glycoprotein from a lyssavirus. For example, it can be from a glycoprotein from another organism, or from a transmembrane protein that is not a glycoprotein. In embodiments, the sequence encoding the transmembrane domain (or portion thereof) and the sequence encoding the cytoplasmic domain are from the same lyssavirus. In embodiments of this aspect of the invention, the sequence encoding site III and the cytoplasmic domain are from the same protein, preferably a lyssavirus protein, such as a lyssavirus glycoprotein.

In a preferred embodiment of this aspect of the invention, the chimeric nucleic acid includes sequences that encode a site III sequence of a lyssavirus glycoprotein, a site II sequence of a lyssavirus glycoprotein, a transmembrane domain of a transmembrane protein, and a cytoplasmic domain of a lyssavirus glycoprotein. The transmembrane domain can be from a lyssavirus or another organism. It is preferred that the chimeric nucleic acid of the invention comprise sequences encoding an antigenic protein (or antigenic portion thereof), especially between the sequences encoding sites II and III.

In preferred embodiments, this aspect of the invention provides a polynucleotide comprising a polynucleotide sequence, wherein the polynucleotide sequence comprises a sequence encoding site III of a lyssavirus glycoprotein, and wherein the polynucleotide sequence does not comprise a sequence encoding an entire lyssavirus glycoprotein.

The sequences encoding site II and site III are sequences encompassing site II and site III of a glycoprotein of a lyssavirus, respectively. In embodiments, the sequence encoding site III is not identical to any of the known site III sequences of lyssaviruses, but shows at least 60% identity with one of the lyssavirus sequences, extending 30 bp on each side of the site III sequence. Sequence analysis and phylogenetic studies are performed using various packages: GCG (version 8.1, 1994), CLUSTAL W (Thompson, 1994 #1040), PHYLIP (Version 3.5: Felseustein, 1993, #1042), and GDE (Genetic Data Environment, Version 2.2: Institut Pasteur Scientific Computer Service—S.I.S.).

In preferred embodiments of this aspect of the invention, the site III sequence is from rabies virus strain PV, or shows at least 60% identity to that site III sequence. Highly satisfactory results are obtained with the following constructs, displayed in FIG. 1: PV-PV or PV III or EBL1-PV or MOK-PV. In highly preferred embodiments, the site III sequence is a PV III sequence.

The inventors have found that the presence of site III of the lyssavirus glycoproteins improves the immunogenicity of compositions comprising the glycoprotein, or portions thereof. Thus, the present invention includes chimeric nucleic acids that comprise a sequence encoding site III of a lyssavirus glycoprotein that is functionally, operatively, and physically linked to a homologous or heterologous sequence encoding a transmembrane domain from natural or synthetic sequence encoding a transmembrane protein (or a portion thereof that is functionally equivalent to the transmembrane domain), and a sequence encoding a cytoplasmic domain (or a portion thereof that is sufficient to stably exist cytoplasmically) from a glycoprotein. Preferably, the glycoprotein is that of a virus and particularly that of a lyssavirus. The chimeric nucleic acid sequences can all be from the same lyssavirus, can be selected from various lyssaviruses, or can be from both lyssaviruses and other viruses and organisms. In preferred embodiments, the nucleic acid sequences encoding the site III and the cytoplasmic domain are from the same lyssavirus.

In addition, the chimeric nucleic acid of the invention can comprise a sequence that encodes an antigenic polypeptide, or an antigenic portion thereof, from another virus or organism (a heterologous sequence). For example, the chimeric nucleic acid can comprise, in addition to the elements set forth above, a sequence that encodes an epitope from leishmania, diphtheria, tetanus, poliomyelitis, foot and mouth disease virus, herpes viruses, canine distemper viruses, parvovirus, and feline immunodeficiency virus. Alternatively, or in addition, the chimeric nucleic acid can comprise a sequence that encodes a tumor antigen. The sequence encoding the heterologous polypeptide (or antigenic portion thereof) is fused (in frame) with the coding sequence detailed above, at any site that results in a functional product. In this way, the chimeric nucleic acid of the invention provides the coding sequence for multiple antigenic determinants, including, but not limited to, rabies virus epitopes.

The chimeric nucleic acids of the invention can be used to make an immunogenic composition. The immunogenic composition can consist essentially of the chimeric nucleic acid or can comprise the chimeric nucleic acid in addition to other components, including, but not limited to, adjuvants, excipients, stabilizers, supra molecular vectors such as those described in European Patent No. 696,191 (Samain et al.), and antigens. The components typically included in immunogenic compositions are well known to the skilled artisan in the field, as are the techniques for preparation of immunogenic compositions, such as vaccines. Therefore, preparation of the immunogenic composition can be achieved by the skilled artisan using well known techniques without undue or excessive experimentation. In embodiments, the immunogenic compositions of this aspect of the invention induce humoral immunity, cellular immunity, or both.

In another aspect of the invention, the chimeric nucleic acid of the invention is present as part of a carrier molecule. The core of the carrier molecule can be any molecule that is known to be useful to maintain, and preferably express, a heterologous peptide or polypeptide-encoding nucleic acid. The core of the carrier molecule can be, for example, a plasmid, a phage, a phagemid, a cosmid, a virus, a yeast artificial chromosome (YAC), or the like. Such core carrier molecules are also commonly referred to as vectors or expression vectors, and are well-known to the skilled artisan and are widely available to the public. The carrier molecule of the invention can be provided as a naked nucleic acid, or packaged, such as in a viral shell or coat. The carrier molecule can be provided as DNA or RNA. Modified forms of these two nucleic acids are included within the scope of the invention. Preferably, the carrier molecule comprises sequences that permit transcription of the chimeric nucleic acids of the invention. These sequences are operably linked to the chimeric nucleic acids of the invention (i.e. their operation/function directly affects expression of the chimeric nucleic acid). In embodiments, these sequences include regulatory elements that allow controlled expression of the chimeric nucleic acids so that expression of the chimeric nucleic acids can be regulated, by, for example, delaying expression until desired or expressing the chimeric nucleic acids in certain tissues or cell types only. Such control elements are known to the artisan in the field and can routinely be inserted or removed from the carrier molecules as desired or necessary using well-known molecular biology techniques and reagents.

In embodiments, the carrier molecule contains a polynucleotide sequence that comprises a sequence encoding a part of a glycoprotein containing at least the site III of a lyssavirus glycoprotein. In embodiments, the carrier molecule contains a polynucleotide sequence that comprises a) a sequence encoding a part of a glycoprotein containing at least the site III of a lyssavirus glycoprotein, and b) a sequence encoding a transmembrane domain of a transmembrane protein. In embodiments, the carrier molecule contains a polynucleotide sequence that comprises a sequence encoding at least the C-terminal half of a lyssavirus glycoprotein. In embodiments, the carrier molecule contains a polynucleotide sequence that comprises a) a sequence encoding at least the C-terminal half of a lyssavirus glycoprotein, and b) a sequence encoding a transmembrane domain of a transmembrane protein. In embodiments, the carrier molecule contains a polynucleotide sequence that comprises a) a sequence encoding at least the C-terminal half of a lyssavirus glycoprotein, b) a sequence encoding a transmembrane domain of a transmembrane protein, and c) a sequence encoding cytoplasmic domain of the lyssavirus glycoprotein.

In an embodiment of the invention, a carrier molecule according to the invention comprises nucleic acids encoding a) the site III of the glycoprotein of a lyssavirus, b) a transmembrane domain of a glycoprotein (or a portion thereof that is functionally equivalent to the transmembrane domain), and c) a sequence that encodes the cytoplasmic domain of the glycoprotein of a lyssavirus. In preferred embodiments of this aspect of the invention, the carrier molecule further comprises a sequence encoding site II of a lyssavirus glycoprotein. In embodiments, the sequence encoding the transmembrane domain (or portion thereof) is a sequence from the glycoprotein of a lyssavirus. In other embodiments, the sequence is from a transmembrane glycoprotein other than a glycoprotein from a lyssavirus. In embodiments, the sequence encoding the transmembrane domain (or portion thereof) and the sequence encoding the cytoplasmic domain are from the same lyssavirus. In embodiments, the sequence encoding the site III and the cytoplasmic domain are from the same lyssavirus.

In a preferred embodiment, the carrier molecule further comprises at least one antigenic sequence other than site III or site II of a lyssavirus. The additional antigenic sequence(s) can be from any organism and includes, but is not limited to, antigenic sequences from parasites (for example leishmania), bacteria, viruses, and tumor cells. The carrier molecule of the present invention, by providing the region of lyssavirus glycoprotein required for enhanced immunogenicity (site III), allows the production of a high level immune response to not only the lyssavirus antigens (sites III and II), but to the heterologous antigen(s) fused to the lyssavirus sequences. The carrier molecule can thus be used to elicit an immune response to multiple antigens from different organisms.

The carrier molecule of the invention preferably comprises a chimeric sequence that encodes a chimeric polypeptide that comprises at least one antigenic determinant, which is site III of a lyssavirus. More preferably, the carrier molecule comprises a chimeric sequence that encodes a chimeric polypeptide that comprises the site III of a lyssavirus and at least one other antigenic determinant selected from the group consisting of an antigen from the same lyssavirus from which the site III was derived and a heterologous antigen. The other antigenic determinants include, but are not limited to, those of pathogenic parasites (e.g., *Plasmodium*), viruses, bacteria, and those of tumor cells.

A preferred carrier molecule according to the invention is pEBL1-PV, which was deposited at the Collection Nationale de Cultures de Microorganismes (CNCM), located at Institut Pasteur, 28, Rue du Docteur Roux, F-75724 Paris, Cedex 15, France, on Dec. 22, 1998, in accordance with the Budapest Treaty, and which was accorded Accession Number I-2114. Another preferred carrier molecule according to the invention is pVIII, which was deposited at the CNCM on Dec. 22, 1998, in accordance with the Budapest Treaty, and which was accorded Accession Number I-2115.

The carrier molecules of the invention can be used to make an immunogenic composition. The immunogenic composition can consist essentially of the carrier molecule or can comprise the carrier molecule in addition to other components, including, but not limited to, adjuvants, excipients, stabilizers, supra molecular vectors (EP 696,191, Samain et al.), and antigens. The components typically included in immunogenic compositions are well known to those skilled in the field, as are the techniques for preparation of inimunogenic compositions, including vaccines. Preparation of the immunogenic composition is a routine matter that can be achieved by the skilled artisan using well-known techniques without undue or excessive experimentation and thus need not be described in detail herein. In embodiments, the immunogenic compositions of this aspect of the invention induce humoral immunity, cellular immunity, or both.

In another aspect, the present invention provides a chimeric polypeptide or protein that is encoded and/or expressed by the chimeric nucleic acid and/or carrier molecule of the present invention. In embodiments, the chimeric polypeptide comprises a) site III of a lyssavirus glycoprotein, b) a transmembrane domain of a glycoprotein (or a functional portion thereof), and c) a cytoplasmic domain of the glycoprotein of a lyssavirus. In preferred embodiments of this aspect of the invention, the chimeric polypeptides further comprise site II of a lyssavirus glycoprotein. In embodiments, the transmembrane domain (or portion thereof) is from the glycoprotein of a lyssavirus. In other embodiments, the transmembrane domain (or portion thereof) is from a transmembrane glycoprotein other than a glycoprotein from a lyssavirus. In other embodiments, the transmembrane domain (or portion thereof) and the cytoplasmic domain are from the same lyssavirus. In embodiments, the site III and the cytoplasmic domain are from the same lyssavirus.

Site II and site III can be obtained from any lyssavirus, and both can, but do not necessarily, come from the same lyssavirus. Further, the sequence of site II and/or site III does not have to be identical to a site II or site III of a glycoprotein of a lyssavirus. In embodiments, the sequence of one or both is not identical to any of the known site II or site III sequences of lyssaviruses, but shows at least 60% identity with one of the lyssavirus sequences, extending 10 residues on each side of the site II or site III sequence.

In preferred embodiments, the chimeric polypeptide of the invention further comprises at least one antigenic determinant other than lyssavirus glycoprotein site III or site II. The other antigenic determinant can be an antigenic protein, or antigenic portion thereof, from another rabies virus or rabies related virus, from another virus, from a parasite, a bacterium, or any other organism or cell that expresses an undesirable antigenic determinant. In embodiments, the other antigenic determinant is from a tumor cell. In embodiments, the other antigenic determinant is from a parasite that causes malaria, such as *Plasmodium falciparum* or *Plasmodium vivax*.

Thus, the invention provides a chimeric polypeptide comprising, as the only antigenic determinant, site III of a lyssavirus. Because antigenicity is dependent, at least to some extent, on the individual to whom the immunogenic composition is administered, a chimeric polypeptide having only one antigenic determinant in one organism may have more than one antigenic determinant in another. However, according to the invention, if a chimeric polypeptide has only one antigenic determinant in at least one individual, regardless of the number it has in other individuals, it is a chimeric polypeptide according to this embodiment of the invention.

The invention also provides a chimeric polypeptide with multiple antigens including, but not limited to, rabies antigens. The chimeric polypeptide can be used as, or as part of, an immunogenic composition, such as a vaccine. Thus, the polypeptide of the invention is an immunogenic polypeptide that contains at least one region (which can be isolated as a fragment) that induces an immunogenic response. In embodiments where a site II, a site III, and another antigenic determinant are present, it is preferably, but not necessary, for the other antigenic determinant to be located between site II and site III in the linear (primary) amino acid sequence of the polypeptide. A preferred antigen other than site II or site III is a tumor antigen from a tumor cell. In embodiments, the polypeptides or proteins of the invention induce humoral immunity, cellular immunity, or both.

Preferably, the chimeric nucleic acids, carrier molecules, and chimeric polypeptides (the "molecules") of the invention are isolated and/or purified. The terms "isolated" and "purified" refer to a level of purity that is achievable using current technology. The molecules of the invention do not need to be absolutely pure (i.e., contain absolutely no molecules of other cellular macromolecules), but should be sufficiently pure so that one of ordinary skill in the art would recognize that they are no longer present in the environment in which they were originally found (i.e., the cellular milieu). Thus, a purified or isolated molecule according to the invention is one that has been removed from at least one other macromolecule present in the natural environment in which it was found. More preferably, the molecules of the invention are essentially purified and/or isolated, which means that the composition in which they are present is almost completely, or even absolutely, free of other macromolecules found in the environment in which the molecules of the invention are originally found. Isolation and purification thus does not occur by addition or removal of salts, solvents, or elements of the periodic table, but must include the removal of at least one macromolecule.

As can be seen from the above disclosure, the invention provides an immunogenic composition. The immunogenic composition can comprise the chimeric nucleic acid, chimeric protein, and/or carrier molecule of the invention. For example, the chimeric polypeptides of the invention can be used to make an immunogenic composition. The immunogenic composition can consist essentially of the chimeric polypeptide or can comprise the chimeric polypeptide in addition to other components, including, but not limited to, adjuvants, excipients, stabilizers, supra molecular vectors (EP 696,191, Samain et al.) and antigens. The components typically included in immunogenic compositions are well known to those skilled in the field, as are the techniques for preparation of immunogenic compositions, such as vaccines. Therefore, preparation of the immunogenic composition can be achieved by the skilled artisan using well known techniques without undue or excessive experimentation.

The immunogenic composition according to the invention is a composition that elicits an immune response at least to a lyssavirus. Because the chimeric nucleic acids (and thus carrier molecules and polypeptides) of the invention can comprise antigenic determinants from the various lyssavirus genotypes in various combinations, the immunogenic composition of the invention can provide, or elicit, a broad spectrum of protection against lyssaviruses that induce encephalomyelitis, including rabies viruses. Furthermore, because sequences encoding multiple lyssavirus epitopes can be included in one chimeric nucleic acid, the immunogenic composition of the invention can provide an immune response to multiple (including all) genotypes of lyssavirus. Preferably, the immunogenic composition of the invention elicits both a cellular and a humoral immune response.

In addition, the immunogenic composition of the invention can provide epitopes from not only lyssaviruses, but from any other organism as well (including antigens produced by human cells, such as undesirable antigens found on the surface of cancerous cells). This permits the construction of immunogenic compositions, including, but not limited to vaccines, having broad applicability in that a single composition can be used to elicit an immune response to multiple pathogens. For example, an immunogenic composition can be made that provides a protective immunological response to a broad range of lyssaviruses while at the same time providing a protective response to other viruses such as polio and influenza. Such a multivalent immunogenic composition is provided by the chimeric nature of the nucleic acids and polypeptides of the invention, as well as the presence of site III of a lyssavirus, which confers a strong immunogenic response to the epitopes of the antigenic polypeptide.

The immunogenic composition of the invention elicits an immunogenic response in individuals to whom it is administered. The immunogenic response can elicit a protective immune response, but such a response is not necessary. According to the invention, immunogenic compositions that elicit a protective response are referred to as vaccines. The immunogenic responses can be enhanced or otherwise modified by the inclusion of components, in addition to the chimeric nucleic acids, chimeric proteins, and carrier molecules of the invention. Alternatively, the immunogenic compositions can consist essentially of the chimeric nucleic acids, chimeric proteins, and carrier molecules of the invention. Thus, the invention encompasses DNA vaccines comprising the chimeric nucleic acids and/or the carrier molecules of the invention.

The invention thus provides a method of making an immunogenic composition. In one embodiment, the method comprises isolating and/or purifying the chimeric nucleic acid or polypeptide or the carrier molecule. In another embodiment, the method comprises isolating and/or purifying the nucleic acid or polypeptide or the carrier molecule, then combining it with additional components. The additional components can be any suitable compound that does not have an adverse effect on the immunogenicity, safety, or effectiveness of the nucleic acid, polypeptide, or carrier molecule of the invention. The additional components include, but are not limited to, compounds and additives that are typically added to immunogenic compositions to enhance immunogenicity, stability, and bioavailability. Exemplary additives are disclosed above and are well known to those skilled in the art.

In another embodiment of this aspect of the invention, the method of making an immunogenic composition is a method of expressing a chimeric (hybrid) polypeptide for use in the production of an immunogenic composition. In this embodiment, the chimeric nucleic acid or carrier molecule of the invention is expressed (transcribed and translated) so that the chimeric polypeptide is produced. The chimeric polypeptide so produced is then isolated and/or purified to an acceptable level so that it can be used to make an immunogenic composition. Production of an immunogenic composition in this embodiment of the invention is according to the disclosure herein. As used herein, a polypeptide is a polymer of amino acids and includes peptides (more than 3 amino acids in length), and proteins (more than 100 amino acids in length). Production of the chimeric polypeptide can be performed in vivo or in vitro. Preferably, production occurs in vivo by expression in bacterial or tissue cultures, and the chimeric polypeptide is isolated or purified from those cultures using known protein purification techniques.

In a further aspect of the invention, methods of making the chimeric nucleic acid, carrier molecules, and chimeric polypeptides of the invention are provided. The methods include commonly known genetic engineering techniques that are well-known to the skilled artisan. Any known technique that is routinely practiced by the skilled artisan can be used to produce and purify the chimeric molecules of the invention. The novelty of the invention does not lie in these techniques, but in the chimeric molecules constructed through the use of them. In this aspect, the methods can be used to make a nucleic acid or carrier molecule for use in the production of an immunogenic composition, such as a DNA vaccine. The invention thus includes a method of making a composition for use in a DNA vaccine.

The invention also provides methods of treating individuals with the immunogenic compositions of the invention. The methods of treating can be methods of therapy or prophylaxis. In embodiments, a method of treating is provided wherein the method induces an immune response in an individual (an animal or a human). In embodiments, the method of treating is a method of inducing a protective response, i.e., a method of vaccination. In other embodiments, the method of treating is a method of inducing an immune response in an individual already suffering from a disease or disorder, such as an infection or cancer. Preferably, the method is a method of vaccination.

The method of treating comprises administering the immunogenic compositions to individuals, or patients, in need of treatment, suspected of needing treatment, or desiring prophylactic (protective) treatment for a disease or disorder. Any known method of administration can be used in this aspect of the invention, including, but not limited to, injection with syringe and needle (e.g., subcutanaceous, intramuscular, intravenous), oral or mucosal administration, inhalation, topical administration (e.g., applying directly to the skin), and by suppository.

In an embodiment of this aspect of the invention, the method comprises administering the chimeric nucleic acids of the invention to an individual in an amount sufficient to elicit an immunogenic reaction (immune response) in the recipient. Preferably, this response is a protective response. The amount of nucleic acid necessary for such an immunization can be determined by those of skill in the art without undue or excessive experimentation. For example, compositions comprising the chimeric nucleic acids and carrier molecules of the invention can be administered in an amount of 40 to 100 µg intramuscularly in one or several injections. A 100 µg dosage is generally useful for dogs, and a 40 µg dosage for mice (weight 20 g).

In another embodiment of this aspect of the invention, the method comprises administering the chimeric polypeptides of the invention to an individual in an amount sufficient to elicit an immunogenic reaction (immune response) in the recipient. Preferably, the response is a protective response. The amount of polypeptide necessary for such an immunization can be determined by those of skill in the art without undue or excessive experimentation. For example, compositions comprising the chimeric polypeptides of the invention can be administered in an amount of 1 to 10 µg intramuscularly in one or several injections.

In another embodiment of this aspect of the invention, the method comprises administering the carrier molecule of the invention to an individual in an amount sufficient to elicit an immunogenic reaction (immune response) in the recipient. Preferably, the response is a protective response. The amount of carrier molecule necessary for such an immunization can be determined by those of skill in the art without undue or excessive experimentation. For example, compositions comprising the carrier molecules of the invention can be administered in an amount of 40 to 100 µg intramuscularly, in one or several injections.

Thus, this aspect of the invention provides a method of DNA vaccination. The method also includes administering any combination of the chimeric nucleic acids, the chimeric polypeptides, and the carrier molecule of the invention to an individual. In embodiments, the individual is an animal, and is preferably a mammal. Preferably, the mammal is selected from the group consisting of a human, a dog, a cat, a bovine, a pig, and a horse. In a preferred embodiment, the mammal is a human. In a preferred embodiment, the mammal is a dog. In a preferred embodiment, the mammal is a horse.

The methods of treating include administering immunogenic compositions comprising not only polypeptides, but compositions comprising nucleic acids (including the carrier molecule) as well. Those of skill in the art are cognizant of the concept, application, and effectiveness of nucleic acid vaccines (e.g., DNA vaccines) and nucleic acid vaccine technology as well as protein and polypeptide based technologies. The nucleic acid based technology allows the administration of nucleic acids, naked or encapsulated, directly to tissues and cells without the need for production of encoded proteins prior to administration. The technology is based on the ability of these nucleic acids to be taken up by cells of the recipient organism and expressed to produce an immunogenic determinant to which the recipient's immune system responds. Typically, the expressed antigens are displayed on the cell surface of cells that have taken up and expressed the nucleic acids, but expression and export of the encoded antigens into the circulatory system of the recipient individual is also within the scope of the present invention. Such nucleic acid vaccine technology includes, but is not limited to, delivery of naked DNA and RNA, and delivery of expression vectors encoding polypeptides of interest (carrier molecules). Although the technology is termed "vaccine", it is equally applicable to immunogenic compositions that do not result in a protective response. Such non-protection inducing compositions and methods are encompassed within the present invention.

Although it is within the present invention to deliver nucleic acids and carrier molecules as naked nucleic acid, the present invention also encompasses delivery of nucleic acids as part of larger or more complex compositions. Included among these delivery systems are viruses, virus-like particles, or bacteria containing the chimeric nucleic acid or carrier molecule of the invention. Also, complexes of the invention's nucleic acids and carrier molecules with cell permeabilizing compounds, such as liposomes, are included within the scope of the invention. Other compounds, supra molecular vectors (EP 696,191, Samain et al.) and delivery systems for nucleic acid vaccines are known to the skilled artisan, and exemplified in WO 90 111 092 and WO 93 06223, and can be made and used without undue or excessive experimentation.

The methods of treating individuals according to the invention include prophylactic treatment, therapeutic treatment, and curative treatment. Prophylactic treatment is treatment of an individual, using the methods of the invention, before any clinical sign of disease or infection is identified. Thus, prophylactic treatment is a preventative treatment and includes vaccination. Prophylactic treatment also includes treatment that is instituted after actual infection or disease inception, but before at least one clinical sign of the disease or infection is observed. Therapeutic treatment is treatment of an individual after at least one clinical sign of disease or infection is identified, or after an individual is known to (or is highly suspected of) having been exposed to a quantity of an agent that sufficient to cause disease or infection. Therapeutic treatment methods do not necessarily result in elimination of the disease or infection; however they do provide a clinically detectable improvement in at least one clinical sign of the disease or infection. Curative treatment methods result in complete elimination of the clinical signs of the disease or infection in the treated individual. Included in the curative treatment methods are those that result in complete removal of the causative agent of the infection or disease, whether it be a virus, bacterium, or host cell (such as a cancerous cell). Also included in curative treatment methods are those that cause complete remission of a disease, i.e., complete elimination of all outward clinical signs of infection or disease, and repression of all detectable clinical manifestations of the infection or disease.

With respect to rabies vaccination, it is known that the virus can be treated both prophylactically (e.g., by vaccination of dogs) and curatively (e.g., by a series of injections to a human previously bitten by a rabid dog). Thus, a preferred embodiment of the present invention is a method of vaccinating an individual with a vaccine comprising the immunogenic composition of the invention. As discussed above, the immunogenic composition of the invention can comprise (or encode) multiple antigenic determinants. Therefore, a method of the invention can include multiple types of treatment for multiple types of diseases or infections. For example, a single method of treatment can comprise prophylactic treatment of polio, prophylactic and therapeutic treatment of rabies, and prophylactic treatment of influenza.

It will be apparent to those of ordinary skill in the art that various modifications and variations can be made in the construction of the molecules, and practice of the methods of the invention without departing from the scope or spirit of the invention. The invention will now be described in more detail with reference to specific examples of the invention, which are not intended to be, and should not be construed as, limiting the scope of the invention in any way.

EXAMPLES

For the Examples, the following materials and methods were used, unless otherwise specifically stated.

Mice. Female BALB/c (H-$2^d$ BALB/C), 6 to 8 weeks of age, and Swiss (14 to 16 g) mice were purchased from "Centre d'Elevage et de Recherche" Janvier (Legenest St Isle, France).

Cells and lyssaviruses. BHK-21 cells used for the production and titration of lyssaviruses were grown in Eagle's minimal essential medium (MEM) containing 5% fetal bovine serum (FBS) and 5% new born calf serum (Perrin, P., 1996, "Techniques for the preparation of rabies conjugates", In Laboratory techniques in rabies, Meslin, F-X., Kaplan, M., and Koprowski, H. Eds., (WHO Geneva):433-445). Neuroblastoma cells (Neuro-2a) used for transfection studies with plasmids were grown in MEM containing 8% FBS.

The interleukin-2 (IL-2)-dependent cytotoxic T cell line (CTLL) was cultured as previously described (Perrin, P. et al., 1988, "Interleukin-2 increases protection against experimental rabies", *Immunobiol.* 177:199-209) in RPMI-1640 medium (Gibco:Flowbio, Courbevoie, France) containing 10% FBS, 1 mM sodium pyruvate, 1 mM non-essential amino acids, $5 \times 10^{31}$ $^5$ M 2-mercaptoethanol, HEPES buffer (Flow Laboratories, Bethesda, Md., USA) and 5 to 10 units (for $1 \times 10^4$ cells) of rat IL-2 (supernatant of splenocytes stimulated with concanavilin A: Con A). Cells were incubated at 37° C. in a humidified atmosphere containing 7.5% $CO_2$.

Fixed PV-Paris/BHK-21, CVS rabies strains as well as rabies-related virus strains (EBL1b, EBL2b, LCMV, and Mok) were multiplied (passaged) in BHK-21 cells as previously described by Perrin, P., 1996, supra. The European bat lyssaviruses used were EBL1b (strain number 8916FRA) derived from a bat isolate from France and EBL2b (strain number 9007FIN; a gift from H. Bouhry) isolated from a human in Finland (Amengal, B. et al., 1997, "Evolution of European bat lyssaviruses", *J. Gen. Virol.* 78:2319-2328). The LCMV strain Arm/53b was kindly provided by Drs. M. Oldstone and M. McChesney (Scripps Clinic, La Jolla, Calif.).

Rabies virus antigens and vaccines. Inactivated and purified lyssaviruses (IPRV) were prepared as described by Perrin, P., 1996, supra. Virus was purified from inactivated (β-propiolactone) and clarified infected-cell supernatants by ultracentrifugation through a sucrose gradient. PV glycoprotein was solubilized from IPRV and purified (G PV) as previously described by Perrin, P., 1996, supra and Perrin, P., et al., 1985, "Rabies immunosomes (subunit vaccine) structure and immunogenicity", *Vaccine*, 3:325-332.

The two inactivated rabies virus used for comparative protection studies were prepared with two different strains: 1) PM as commercial vaccine for human use; (Pasteur Vaccines Mames-1a-Coquette France; Lot Y0047); 2) PV as a vaccine for laboratory use (IPRV).

Construction of plasmids expressing lyssavirus G genes. The region (amino acids 253-275) overlapping the only nonconformational epitope (VI) (FIG. 1) was chosen for the construction of chimeric genes because it is presumably less structurally constrained than the two major antigenic sites II and III. The homogeneous and chimeric lyssavirus G genes (see FIG. 1) were introduced into the eukaryotic expression vector pCIneo (Promega), propagated and amplified in *E. coli* strain DH5a by standard molecular cloning protocols well known to the skilled artisan. Plasmids pGPV-PV and pGMok-PV were prepared as previously described (Bahloul, C., et al., 1998, "DNA-based immunization for exploring the enlargement of immunological cross-reactivity against the lyssaviruses", *Vaccine* 16:417-425). Plasmids pGPV-Mok, pG-PVIII and pGEBL1-PV were obtained as follows.

For pGPV-Mok, the coding sequence of the site II part of G PV (amino acids 1-257) was amplified by RT-PCR using degenerated primers:

```
                                   (SEQ ID NO.: 1)
PVXbaI:  5' TTCTAGAGCCACCATGGTTCCTCAGGCTCTCCTG 3'

(SEQ ID NO.: 2)
PVBclI:  5' ATTGATCAACTGACCGGGAGGGC 3'
```

The PCR product was inserted into the SmaI site of pUC19, then excised with BclI and EcoRI and ligated between the same sites in pGMok-Mok giving pGPV-Mok, containing an in-frame fusion of amino acids 1-257 from G PV with amino acids 258-503 from G Mok.

The pG-PVIII gene, with an internal in-frame deletion between the end of the PV signal peptide and residue 253, was obtained by introducing a synthetic adaptor between the EcoRI and BclI restriction sites of the pGMok-PV plasmid. This PV adaptor, containing a single EcoRI site, was generated by annealing 200 picomoles of each primer in 250 mM Tris-HCl pH 7.7. pG-PVIII was deposited on Dec. 22, 1998 with the Collection Nationale de Cultures de Microorganismes (CNCM), Paris, France, and given Accession Number I-2115.

```
PVp1:
                                   (SEQ ID NO.: 3)
5' AATTCTAGAGCCGCCACCATGGTTCCTCAGGCTCTCCTGTTTGTACC

CCTTCTGGTTTTTCCATTGTGTTTTGGGAAGAATTCCCCCCCCGGTCAGT

T 3'

Pvp2:
                                   (SEQ ID NO.: 4)
5' GATCAACTGACCGGGGGGGAATTCTTCCCAAAACACAATGGAAAAA

CCAGAAGGGGTACAAACAGGAGAGCCTGAGGAACCATGGTGGCGGCTCTA

G 3'
```

To generate the pGEBL1-PV gene, a synthetic adaptor corresponding to amino acids 2-14 from EBL-1a (strain 8615POL), single BstEII and EcoRI restriction sites were generated in the same way as that for pG-PVIII, by annealing:

EBL1p1:
(SEQ ID NO.: 5)
5' AATTTCCCAATCTACACCATCCCGGATAAAATCGGACCGTGGTCACC

TATTCCG 3'

EBL1p2:
(SEQ ID NO.: 6)
5' AATTCGGAATAGGTGACCACGGTCCGATTTTATCCGGGATGGTGTAG

ATTGGGA 3'

This EBL1 adaptor was ligated in-frame into the EcoRI site of pG-PVIII. A fragment corresponding to amino acids 15-253 from EBL-1a (strain 8615POL) was then generated by RT-PCR of viral RNA using primers EBL1p3 and EBL1p4:

EBL1p3:
(SEQ ID NO.: 7)
5' CCGTGGTCACCTATTGATATAAACCATCTCAGCTGCCCAAACAACTT

GATCGTGGAAGATGAG 3'

EBL1p4:
(SEQ ID NO.: 8)
5' GGAATTCGAGCACCATTCTGGAGCTTC 3'

The RT/PCR product was digested with BstEII and EcoRI and was ligated into the same sites introduced via the EBL1 adaptor, resulting in an in-frame fusion between the PV signal peptide, the EBL1a site II part and the PV site III part. The identity of each construct was confirmed by automatic sequencing with dye terminator reaction on an ABI 377 sequencer (Perkin-Elmer). pEBL1-PV was deposited with the CNCM on Dec. 22, 1998, and assigned the Accession Number I-2114.

Insertion of foreign B and CD8 cell epitopes in truncated or chimeric G genes. The previously reported truncated (pG-PVIII) and chimeric genes (pGEBL1-PV) containing a unique EcoRI cloning site were used for the insertion of foreign B and CD8 cell epitopes. Lyssavirus G genes were introduced into the eukaryotic expression vector pCIneo (Promega), propagated and amplified in *Escherichia coli* strain DH5a by standard molecular cloning protocols.

B and CD8 cell epitopes were inserted into the EcoRI restriction site of the truncated or chimeric lyssavirus G genes in the hinge region (amino acids 253 to 275) of the molecule at position 253. The B cell epitope (named <<B>>) corresponded to fragment C3 (amino acid 93 to 103: DNPASTT-NKDK: SEQ ID NO.: 9) of the poliovirus VP1 protein. The CD8 cell epitope (named <<CTL>>) corresponded to amino acids 119-127 (PQASGVYMG: SEQ ID NO.: 10) or amino acids 117-132 (ERPQASGVYMGNLTAQ: SEQ ID NO.: 11) of the lymphocyte choriomeningitis virus nucleoprotein. Plasmids p(B-CTL)2-GPVIII, pGEBL1-(B)-PV, pGEBL1-(CTL)-PV, pGEBL1-(B-CTL)-PV, pGEBL1-(B-CTL)$_2$-PV, and pGEBL1-(CTL-B)-PV were obtained as follows (see also FIG. 1):

The p(B-CTL)2-GPVIII gene was generated by a two step cloning of a synthetic adapter in the unique EcoRI restriction site by annealing 200 picomoles of each primer:

<<B-CTLp1>>:
(SEQ ID NO.: 12)
5' AATTCAGATAACCCGGCGTCGACCACTAACAAGGATAAGCTGTTCGC

AGTGCCTCAGGCCTCTGGTGTGTATATGGGT 3'

<<B-CTLp2>>:
(SEQ ID NO.: 13)
5' AATTACCCATATACACACCAGAGGCCTGAGGCACTGCGAACAGCTTA

TCCTTGTTAGTGGTCGACGCCGGGTTATCTG 3'.

For pGEBL1-(B)-PV, pGEBL1-(CTL)-PV, the synthetic adaptors used for the insertion were respectively:

B:
<<Bp3'>>:
(SEQ ID NO.: 14)
5' AATTTGGATAACCCGGCGTCGACCACTAACAA 3'

<<Bp4>>:
(SEQ ID NO.: 15)
5' AATTCTTATCCTTGTTAGTGGTCGACGCCGGG 3'

CTL:
<<CTLp5>>:
(SEQ ID NO.: 16)
5' AATTTGGAGAGACCTCAGGCCTCTGGTGTGTATATGGGTAATCTTAC

GGCCCAG 3'

<<CTLp6>>:
(SEQ ID NO.: 17)
5' AATTCTGGGAAGTAAGATTACCCATATACACACCAGAGGCCTGAGGT

CTCTCCA 3'.

For pGEBL1-(B-CTL)-PV and pGEBL1-(CTL-B)-PV plasmid construction, pGEBL1-(B)-PV and pGEBL1-(CTL)-PV were used under the same conditions as above to insert CTL and B sequences, respectively, in the chimeric genes.

The identity of each construct was confirmed by automatic sequencing with dye terminator reaction on an ABI 377 sequencer (Perkin-Elmer).

Transient expression experiments. The ability of plasmids to induce transient expression of G related antigens was tested after transfection of Neuro 2a cells using the DOTAP cationic liposome-mediated method according to the manufacturer's instructions (Boehringer Mannheim). Each well of a cell culture microplate (Falcon) was inoculated with $3 \times 10^4$ cells (in MEM, 10% FBS) and incubated for 24 h at 37° C. in a humidified atmosphere containing 7.5% $CO_2$. The plate was then washed with MEM without FBS and incubated as above for 1 h. The cell supernatant was removed, and the wells were washed and filled with a total volume of 50 µl transfection solution, which contained 0.1 µg plasmid and 6 µl DOTAP ((N-(1-2,3,-dioleoyloxy) propyl)-N,N,N-trimethylammoniummethyl-sulfate) in sterile HEPES-buffered saline (150 mM NaCl, 20 mM HEPES) previously incubated at room temperature for 15 min. The plate was incubated for 5 h at 37° C. in the presence of 7.5% $CO_2$. Two hundred µl MEM containing 2% FBS were added to each well and the plate was incubated for 24 to 140 h in the same conditions, before analysis of transient expression by indirect immunofluorescence.

The ability of plasmids to induce transient expression of G and foreign related antigens was tested after transfection of Neuro 2a cells using the FuGENE 6 transfection reagent according to the manufacturer's instructions (Boehringer Mannheim). Each well of a cell culture Labtek chamber Nunc (Life Technologies) was inoculated with $3\times10^4$ cells (in MEM, 10% FBS) and incubated for 24 h at 37° C. in a humidified atmosphere containing 7.5% $CO_2$. The plates were then washed with MEM without FBS and wells were filled with 50 μl transfection solution: 0.1 μg plasmid, 3 μl of FuGENE 6 transfection reagent, and 47 μl of HEPES-buffered saline. The plate was incubated for 18 h at 37° C. in the presence of 7.5% $CO_2$. Two hundred μl MEM containing 5% FBS were added to each well and the plate was incubated another 24 h under the same conditions before analysis of transient expression by indirect immunofluorescence.

Antibodies. Polyclonal antibodies (PAb) directed against PV and Mok G were obtained as described by Perrin, P., 1996, "Techniques for the preparation of rabies conjugates", In *Laboratory techniques in rabies*, Meslin, F-X., Kaplan, M., and Koprowski, H. Eds. (WHO Geneva):433-445, by rabbit immunization with purified virus glycoprotein. PAb against EBL-1b virus was obtained by mouse immunization with inactivated and purified virus.

Three monoclonal antibodies (MAb) directed against PV G were also used. PVE12 MAb (a MAb developed by M. Lafon et al., 1985, "Use of a monoclonal antibody for quantitation of rabies vaccine glycoprotein by enzyme immunoassay", *J. Biol. Standard* 13:295-301) recognizes site II of native G. D1 MAb (IgG 1 isotype), produced in our laboratory, recognizes site III of native but not SDS-treated G. 6A1 MAb (a MAb reported in Lafay et al., 1996, *J. Gen. Virol.* 77:339-346) recognizes SDS-denatured G protein and more precisely two peptides located downstream from site III, near the COOH-terminal part of the G ectodomain (amino acids 342-433 and 397-450).

Immunofluorescence microscopy. Transient expression of G antigens in transfected cells was assessed with and without permeabilization (30 min incubation with 80% acetone on ice followed by air drying). Transfected cells were incubated for 1 h at 37° C. with PAb or MAb. They were washed with PBS, and incubated for 1 h at 37° C. with goat anti-rabbit or anti-mouse FITC-conjugated secondary antibody (Nordic Immunol. Labs, The Netherlands). Cells were washed, mounted in glycerol, and examined in a Leica inverted fluorescence microscope.

Two mouse monoclonal antibodies directed against PV G (D1 MAb IgG 1 isotype) and poliovirus (C3 MAb) were used for antigen staining by indirect immunofluorescence (IIF). D1 MAb recognizes the site III of native but not SDS-treated G and C3 MAb recognizes the 93-103 region of the PV-1 capsid VP1 protein. A rabbit neutralizing polyclonal antibody directed against the native poliovirus type 1 was also used.

Transient expression was assessed after 3% paraformaldehyde (Sigma) fixation (20 min incubation at room temperature) without permeabilization. Fixed cells were incubated for 1 h at room temperature with MAb. They were washed with phosphate-buffered saline (PBS), and incubated for 1 h at room temperature with goat anti-mouse or anti-rabbit FITC-conjugated secondary antibody (Nordic Immunol. Labs, The Netherlands). Cells were washed, mounted in Mowiol (Sigma) and examined in a Leica inverted fluorescence microscope.

Putative PEST sequence analysis. Polypeptide PEST sequences potentially involved in rapid degradation of protein were analyzed with the computer program PEST find developed according to Rogers, S. et al., 1986, "Amino acid sequences common to rapidly degraded proteins: the PEST hypothesis", *Science* 234:364-369.

Injection of plasmids into mice. For immunological studies, BALB/c mice were anesthetized with pentobarbital (30 mg/kg) and 20-50 μg plasmid (diluted in PBS) was injected into each anterior tibialis muscle. This was more effective than injection via the quadriceps route. Blood was collected for antibody assay of serum on various days by retro-orbital puncture.

For protection studies against LCMV, mice received 3.5 μg of cardiotoxin (Latoxan A.P., Les Ulis, France) in each leg four days before anaesthesia and immunization to degenerate the muscle.

Interleukin-2 release assay. Fourteen days after injection, spleens were removed from naive, or plasmid-injected BALB/c mice. Splenocytes (1 ml aliquots containing $6\times10^6$) were stimulated with 0.5 μg lyssavirus antigen (e.g., IPLV-PV and IPLV-EBL1) or 5 μg concanavilin A (Miles) in 24-well plates (Nuclon-Delta, Nunc) and cultured according to standard procedures in RPMI-1640 medium (Gibco) containing 10% FBS, 1 mM sodium pyruvate, 1 mM non-essential amino acids, $5\times10^{-5}$ M 2-mercaptoethanol, 10 mM HEPES buffer (Flow Laboratories). Cells were incubated for 24 h at 37° C. in a humidified atmosphere containing 7% $CO_2$. Under these conditions, cells producing IL-2 are mainly $CD4^+$ cells. IL-2 produced in supernatants of splenocyte cultures was titrated by bioassay using CTLL cells as previously described by Perrin, P. et al., 1996, "The antigen-specific cell-mediated immune response in mice is suppressed by infection with pathogenic lyssaviruses", *Res. Virol.* 147:289-299. Cell proliferation was determined in triplicate, based on the uptake of $^3$H-thymidine (New England Nuclear). IL-2 concentration was determined as units per ml (U/ml) using mouse recombinant IL-2 (Genzyme Corporation, Cambridge, Mass., USA) as the reference. CTLL cells grew in the presence of mouse IL-2 and anti-IL-4 antibodies but not in the presence of IL-4 (up to 10 U/ml) and in the absence of IL-2. IL-2 was predominantly detected by this technique.

Antibody assays. For antibody assay of serum, blood was collected on various days by retro-orbital puncture. Rabies IgG were titrated by enzyme-linked immunosorbent assay (ELISA) using microplates coated with purified rabies glycoprotein. Titer corresponded to the reciprocal dilution of the serum sample giving the optical density equivalent to twice that given by serum (diluted 1/20) of PBS injected mice. Total anti-rabies IgG or IgG1, IgG2a and IgG3 isotypes were assayed by ELISA using microplates coated with IPRV as previously described (Perrin, P. et al., 1986, "The influence of the type of immunosorbent on rabies antibody EIA; advantages of purified glycoprotein over whole virus", *J. Biol. Standard.* 14:95) with rabbit anti-mouse IgG isotype sera as the secondary antibody (Nordic Immunol. Labs, The Netherlands) and a goat anti-rabbit IgG peroxidase conjugate (Nordic Immunol. Labs, The Netherlands) as the tertiary antibody.

Lyssavirus neutralizing antibodies were titrated by the rapid fluorescent focus inhibition test (RFFIT) (described by Smith, J. et al., 1996, "A rapid fluorescent focus inhibition test (RFFIT) for determining virus-neutralizing antibody", In *Laboratory techniques in rabies*, Fourth edition (Eds Meslin, F-X; Kaplan, M and Koprowski, H) WHO, Geneva.: 181-189) with the previously described modifications of Perrin, P. et al., 1986, *J. Biol. Standard.* 14:95. Infected cell supernatants (PV, CVS, and EBL2 viruses) and purified viruses (Mok and EBL1 viruses) were used. Anti-PV or CVS antibody titers are expressed in international units per ml (IU/ml) using the 2nd International Standard (Statens Seruminstitut, Copenhagen, Denmark) as the reference. For antibody titer determination against other lyssaviruses, the serum dilution causing 50% inhibition of the fluorescent focus rate was defined as having the same VNAb titer as for reference assayed against CVS.

Antibodies to PV-1 were assayed by ELISA as previously described using microplates coated with a synthetic peptide constituted by a trimer of amino acids 93-103 of VP1. Anti-LCM IgG production was also tested by ELISA.

Protection test. The protective activity of vaccines and plasmids was determined according to the NIH potency test. Dilutions of vaccine were injected intra-peritoneally (i.p.) into mice on days 0 and 7 whereas plasmids (40 μg) were injected into each anterior tibialis muscle on day 0 only. Mice were then intra-cerebrally (i.c.) challenged on day 21 with about 30 $LD_{50}$ of various lyssaviruses (CVS, LCMV, EBL1b, or EBL2b). Animals were observed for 28 days or alternatively sacrificed at day 21 post-challenge and blood samples collected in order to control the virus clearance and the anti-LCMV IgG production.

Example 1

Transient Expression of Lyssavirus G Genes

Plasmids containing homogeneous (pGPV-PV), truncated (pG-PVIII), and chimeric (pGEBL1-PV, pGMok-PV and pGPV-Mok) lyssavirus G genes were used to transfect Neuro 2a cells. Cell staining by indirect immunofluorescence is reported in FIG. 2 and can be summarized as follows.

Figure 2C:
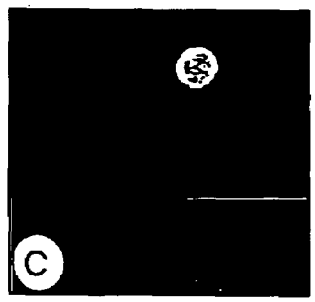
Figure 2D:
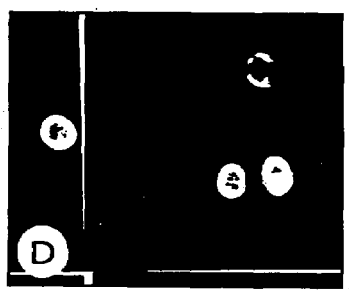
Figure 2E:
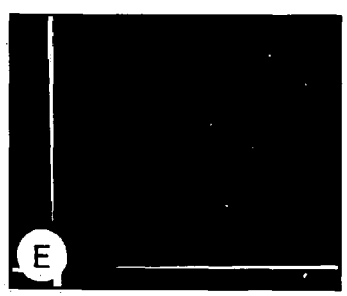
Figure 2F:
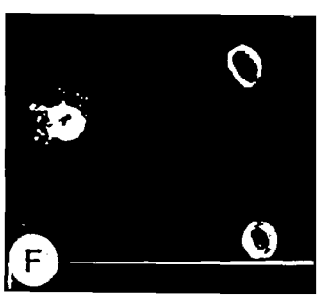
Figure 2G:
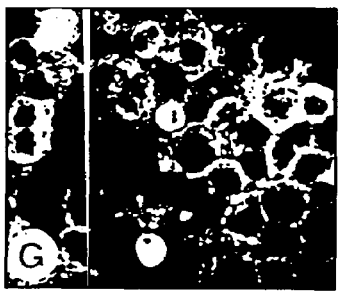
Figure 2H:
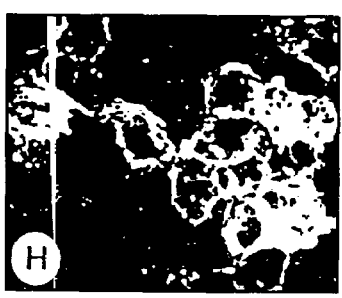
Figure 2I:

After transfection with pGPV-PV, antigen was detected with PV PAb (FIG. 2A), PV D1 MAb (FIG. 2B), or PV E12 MAb (not shown), mostly at the cell membrane (similar results with non-permeabilized cells, data not shown) and very few detected with 6A1 MAb (FIG. 2C). Cells transfected with pG-PVIII were round in shape and completely stained (both cytoplasm and membrane) with PV PAb (FIG. 2D) or 6A1 MAb (FIG. 2F), but not with PV D1 MAb (FIG. 2E). Cells transfected with pGEBL1-PV were stained mostly at the cell membrane with PV PAb (FIG. 2G), PV D1 MAb (FIG. 2H), or EBL-1 PAb (FIG. 2I). Cells transfected with pGMok-PV were stained (mainly at the membrane) with PV PAb (FIG. 2J), PV D1 MAb (FIG. 2K), Mok PAb (FIG. 2L), and very few stained with 6A1 MAb (not shown). Cells transfected with pGPV-Mok were stained with PV PAb (FIG. 2M) or Mok PAb and round in shape (FIG. 2N).

Cell transfection distinguishes two types of G antigens: 1) stained principally at the membrane of cells normal in shape, in particular using neutralizing MAb directed to site II (PV E12) and III (PV D1); and 2) stained in both the cytoplasm and membrane of cells round in shape, in particular using MAb (6A1), which recognizes the denatured G molecule.

Figure 3A:
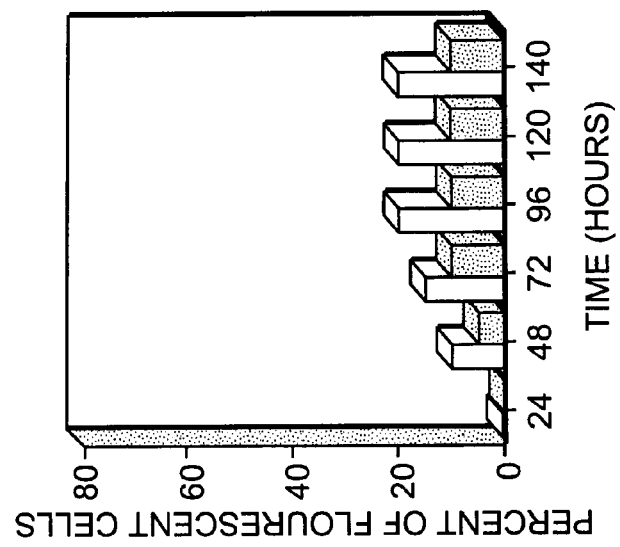
Figure 3B:
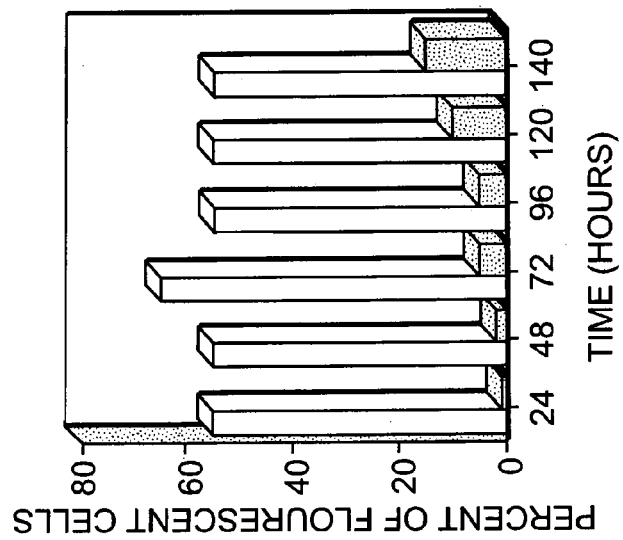
Figure 3C:
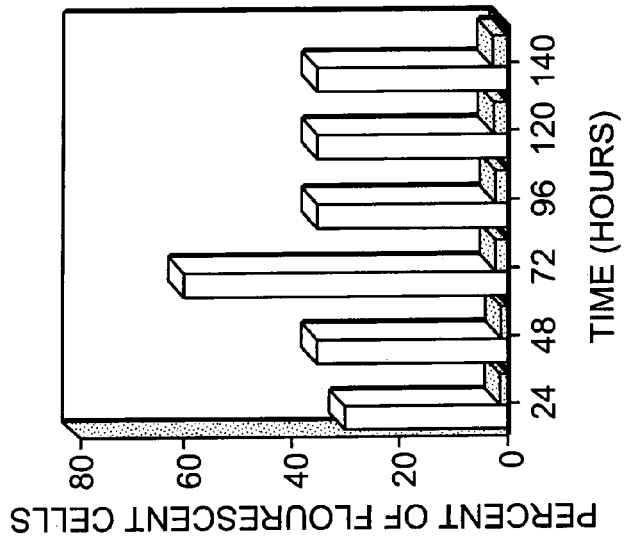

The kinetics of G protein expression was studied upon transfection of cells with three representative plasmids: pGPV-PV (homogenous), pGEBL1-PV (chimeric), and pG-PVIII (truncated). pGPV-PV produced G antigens in about 60% of cells when stained with PV PAb, whereas very few cells were stained with PV 6A1 MAb at any time point (FIG. 3A). About 55% of cells transfected with pGEBL1-PV were stained with PV PAb and up to 15% with 6A1 MAb (FIG. 3B) indicating that some G molecules were denatured. Ten to twenty percent of cells transfected with pG-PVIII were round in shape and stained with PV PAb whereas 5 to 10% were positive with 6A1 MAb, indicating that G molecules were denatured (FIG. 3C).

Example 2

Induction of IL-2-Producing Cells

The ability of the plasmids, pGPV-PV, pG-PVIII, pGEBL1-PV, pGMok-PV and pGPV-Mok to induce IL-2-producing cells was assayed and the results are shown in FIG. 4. Plasmids with the site III part of PV, whether unfused (pG-PVIII) or with any lyssavirus site II part (PGPV-PV, pGEBL1-PV and pGMok-PV), efficiently induced IL-2 producing cells (240 to 550 mU/ml). This was true even for pG-PVIII, which, however, had only low efficiency for both cell transfection (see above) and antibody induction (see below). For the chimeric plasmids EBL1-PV and Mok-PV, the T-cell response was greater after stimulation with inactivated and purified PV than with EBL-1b or Mok viruses. This was not due to the quality of the purified antigens because immunization of BALB/c mice with PV, EBL-1b, or Mok inactivated and purified virus followed by in vitro stimulation with the same antigen induced similar levels of IL-2 production (PV: 250 mU/ml, EBL-1b: 350 mU/ml and Mok: 400 mU/ml). In contrast, the plasmid pGPV-Mok induced only a weak Th cell response (IL-2 titer: 50 mU/ml), which was similarly produced in vitro after stimulation with either inactivated and purified PV or Mok virus.

Example 3

Serological Assays

The truncated pG-PVIII plasmid did not induce the production of rabies antibodies, when assayed by RFFIT and ELISA. However when IL-2 was injected together with pG-PVIII, and then alone 7 days later, antibodies were detected on day 21 only by ELISA (data not shown). Thus, the site III part was expressed in vivo and induced a weak production of non-neutralizing antibodies, which was boosted by exogenous IL-2.

Figure 5A:
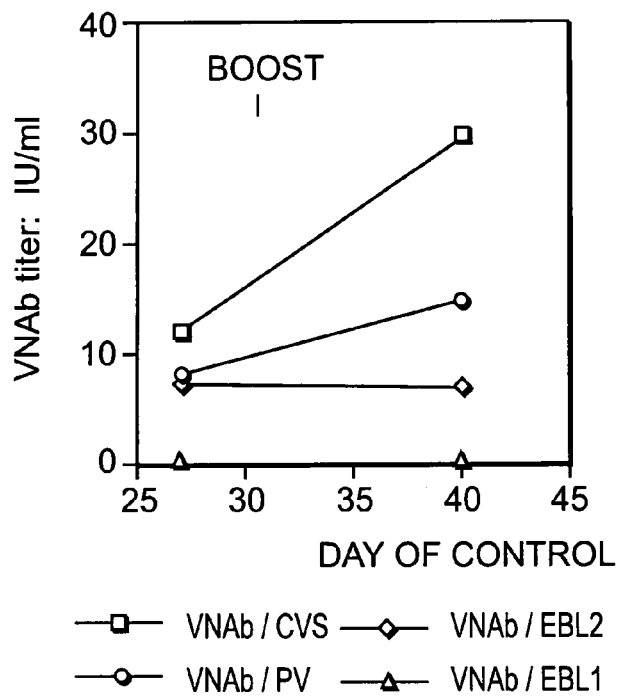

In contrast, when the site III part of PV was linked with the homologous site II part, as in pGPV-PV, it displayed strong immunogenicity. A single injection of pGPV-PV plasmid into mice resulted in high levels of VNAb measured 27 days later against both the homologous PV and CVS viruses and the heterologous EBL-2b virus (FIG. 5A). The antibody isotype induced was mainly IgG 2a, but a weak IgG 1 response was also observed (data not shown). However, the correlation between VNAb titers against PV was stronger with IgG 2a (r=0.974) than with IgG 1 titer (r=0.71), indicating that VNAb induced by DNA-based immunization were mainly IgG 2a. The VNAb titer against the homologous PV and CVS viruses increased when mice received a booster injection on day 30 and their sera were checked at day 40, but not the VNAb titers against the heterologous EBL-2b virus which remained unchanged (FIG. 5A). Likewise, under these conditions, a relationship between VNAb level induced by pGPV-PV and the protection of mice against an i.c. challenge with CVS was seen: all animals with a VNAb titer (on day 20) above 1.5 IU/ml survived the challenge on day 21 (not shown). In contrast, no significant amount of VNAb against EBL-1b was produced after a single injection or after a boost.

Figure 5B:
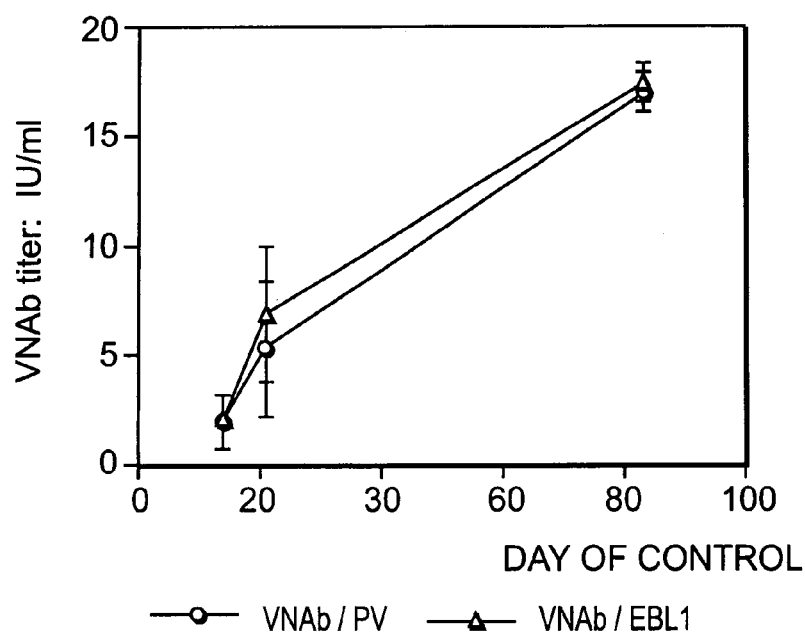

In view of these results and a previous observation that the chimeric plasmid pGMok-PV induced VNAb against both PV and Mok viruses, the capability of the site III part of PV to carry the heterologous EBL1 site II part was investigated. A single injection of the chimeric plasmid pGEBL1-PV similarly induced VNAb against both PV and EBL-1b viruses (FIG. 5B). Fourteen days after injection, titers were 2 IU/ml and they increased to 17 IU/ml after 80 days. The level of VNAb production against EBL-1b was always higher than that against PV, but the difference was not significant.

Taken together, these results clearly demonstrate that chimeric G genes encoding the site III part of PV and the site II part of G of other lyssaviruses such as EBL-1b or Mok are very potent inducers of VNAb against both parental viruses. In contrast, the symmetric pGPV-Mok construct did not induce VNAb against either PV or Mok viruses (not shown).

Example 4

Protection Assays Against European Lyssaviruses

The ability of both the homogenous pGPV-PV and the chimeric pGEBL1-PV plasmid to induce protection against an i.c. challenge with viruses representing lyssavirus genotypes involved in the transmission of encephalomyelitis in Europe (CVS for GT1, EBL1b for GT5, and EBL2b for GT6) was tested. Their efficiency was compared with that of a commercially available vaccine (PM strain: GT1) and a laboratory preparation (PV strain: GT1), and the results are presented in FIG. 6.

Figure 6B:
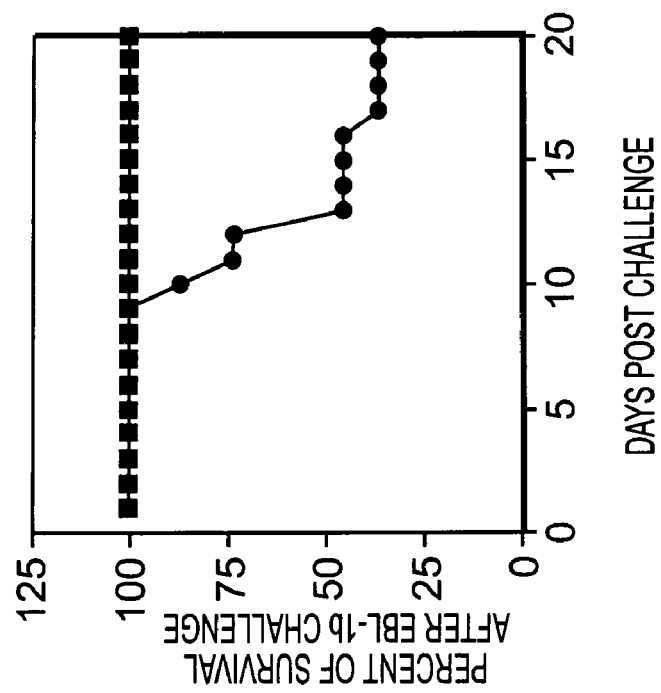
Figure 6A:
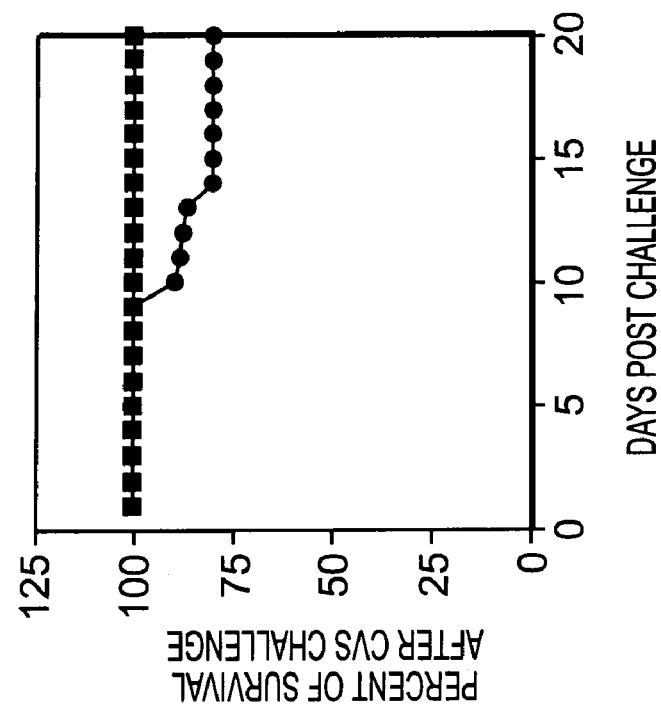
Figure 6D:
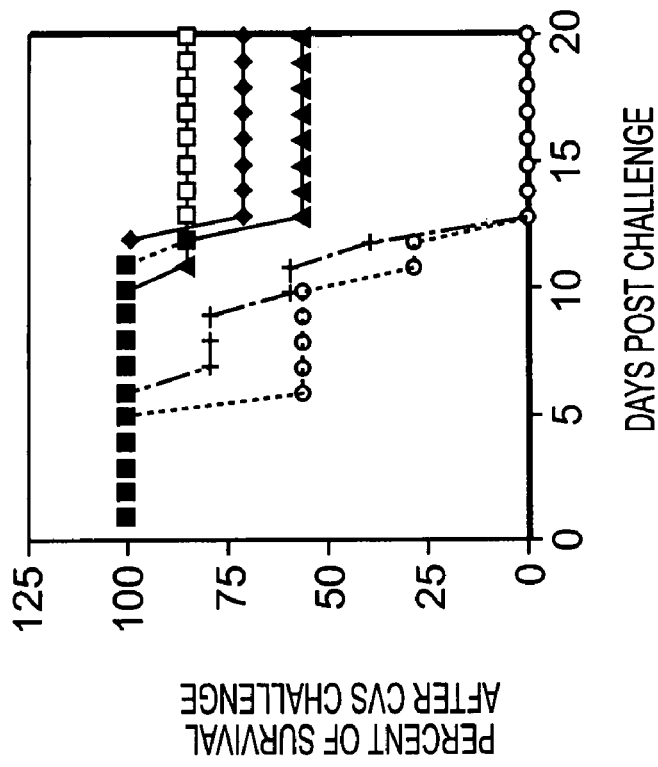

The plasmid backbone (pCIneo) did not induce protection against any virus (FIGS. 6d, e, and f). In contrast, pGPV-PV protected 70% of BALB/c (and 85% of Swiss) mice against CVS (FIG. 6d), 30% against EBL1b (FIG. 6e), and 72% against EBL2b (FIG. 6f). In the same conditions, pGEBL1-PV protected 60% of BALB/c mice against CVS (FIG. 6d), 75% against EBL1b (FIG. 6e) and 80% against EBL2b (FIG. 6f). Thus, if immunization with any of the two plasmids showed no significant difference in the protection against CVS (GT1) and EBL2b (GT6), the chimeric pGEBL1-PV was far more efficient against EBL1b (GT5) and is clearly the best candidate for protection with DNA-based immunization against the three European lyssavirus genotypes.

Figure 6C:
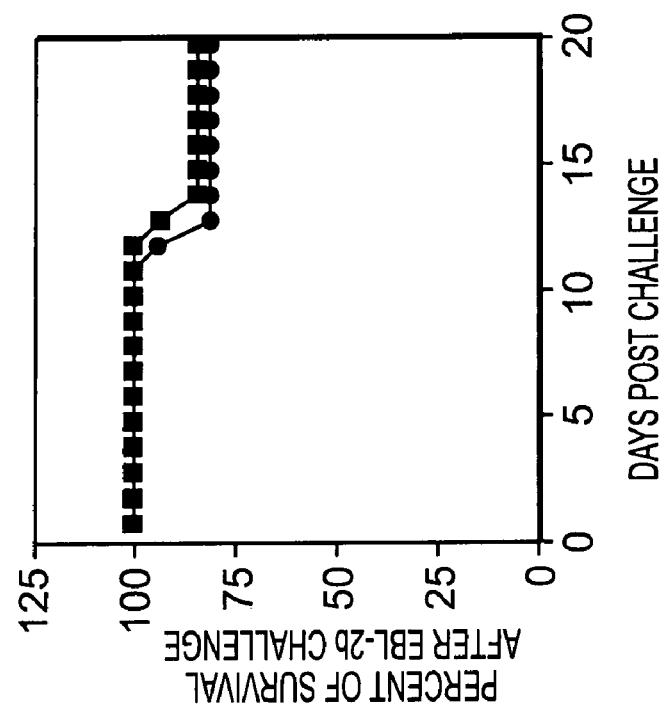
Figure 6F:
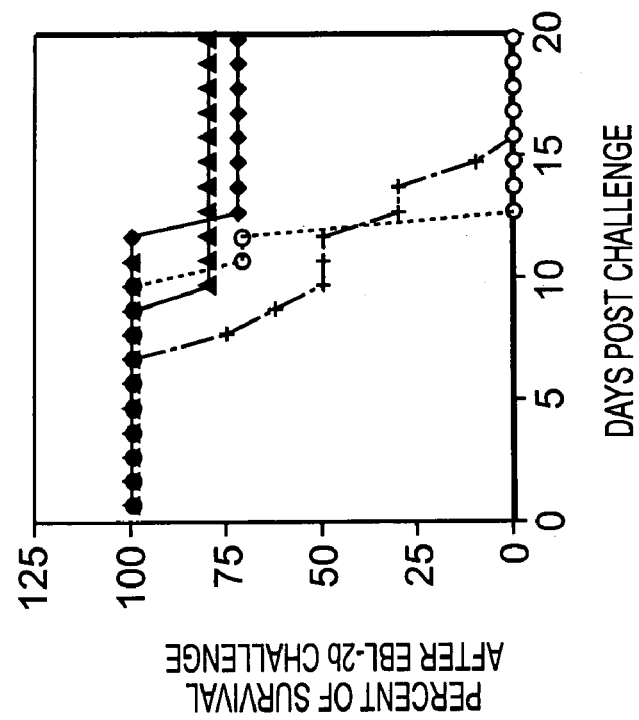
Figure 6E:
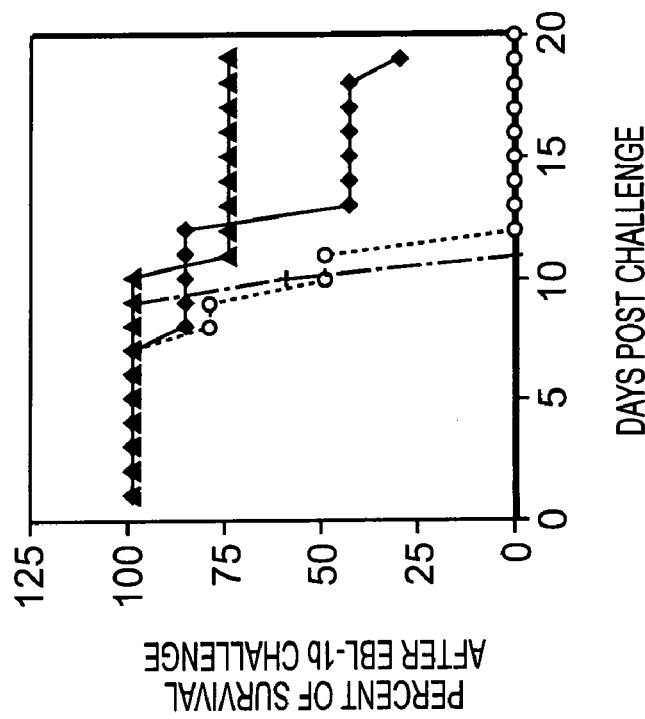
Figure 7A:
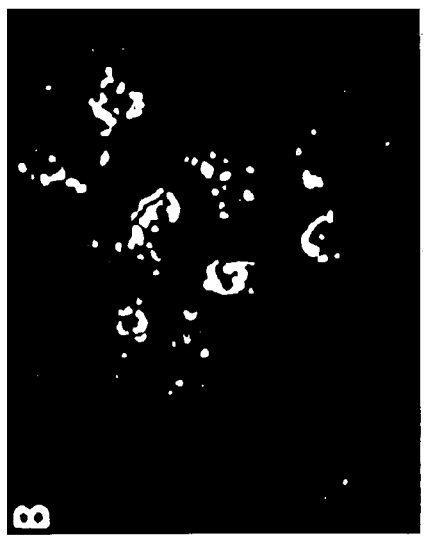
Figure 7B:
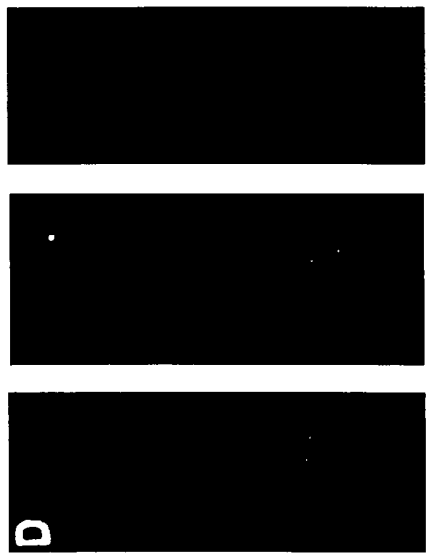
Figure 7C:
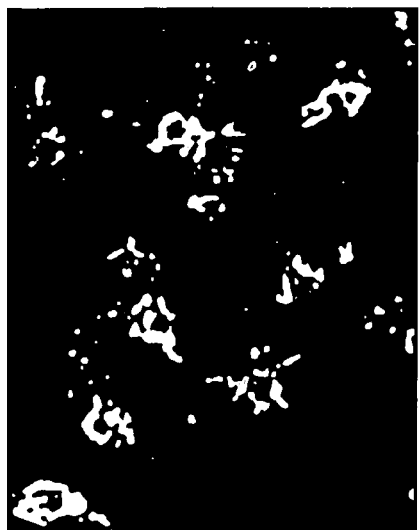
Figure 7D:
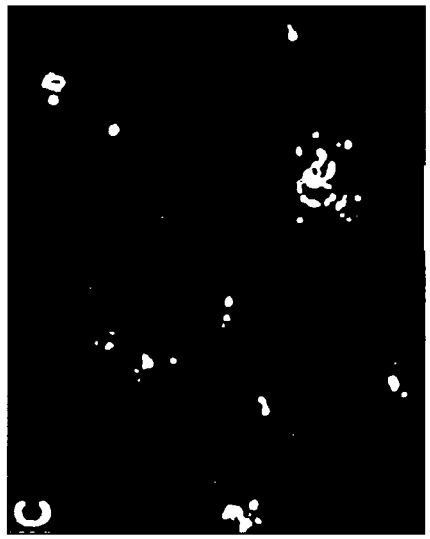

Concerning the protection induced by inactivated cell culture vaccines using the PM and PV strains against the same challenges, a human dose of PM vaccine diluted 1/10th protected 80% of mice against CVS (FIG. 6a), 36% against EBL1b (FIG. 6b), and 80% against EBL2b (FIG. 6c). Under the same conditions, 2 µg of PV IPRV protected 100% of mice against both CVS (FIG. 6a) and EBL1b (FIG. 6b) and 85% against EBL2b (FIG. 6c). For a vaccine dose that protected 80 to 85% of the animals against EBL2b, the PV strain protected 100% and PM strain only 36% against EBL1b. Thus, the PM strain is less effective than the PV strain against EBL1b.

Example 5

Transient Expression of Lyssavirus G Genes

Plasmids containing the foreign antigen encoding sequences associated with the truncated (pG-PVIII) or chimeric (pGEBL1-PV) lyssavirus G genes were tested for their ability to transiently transfect Neuro 2a cells. Except for pG(B-CTL)$_2$-PVIII, which induced an IIF staining (in the cytoplasm) only after permeabilization, all plasmids induced the expression of polio- and lyssaviruses related antigens at the cell membrane of non-permeabilized cells, as previously reported for the same plasmids without foreign epitopes.

For illustration, transfection results obtained with pGEBL1-(B-CTL)$_2$-PV are reported in FIG. 7. Both rabies virus G part recognized by PV D1 MAb (FIG. 7A) and poliovirus insert recognized either by the C3 MAb (FIG. 7B) or the anti poliovirus type 1 PAb (FIG. 7C) were evidenced, whereas no staining was observed with the same MAb and PAb on PChIeo transfected cells (FIG. 7D). This clearly indicates that, except for pG(B-CTL)$_2$-PVIII, the chimeric pGEBL1-PV glycoprotein allowed the expression of the poliovirus B cell epitope alone or in association with the LCMV CTL cell epitope at the cell surface membrane under a native form whereas the expression of lyssavirus G was maintained.

Example 6

Immunogenicity of Foreign Epitopes Carried by the Truncated Glycoprotein

The truncated pGPVIII gene was used to carry and expressed C3 VP1 B cell and LCMV CD8$^+$ CTL epitopes in mice after DNA-based immunization.

Figure 8A:
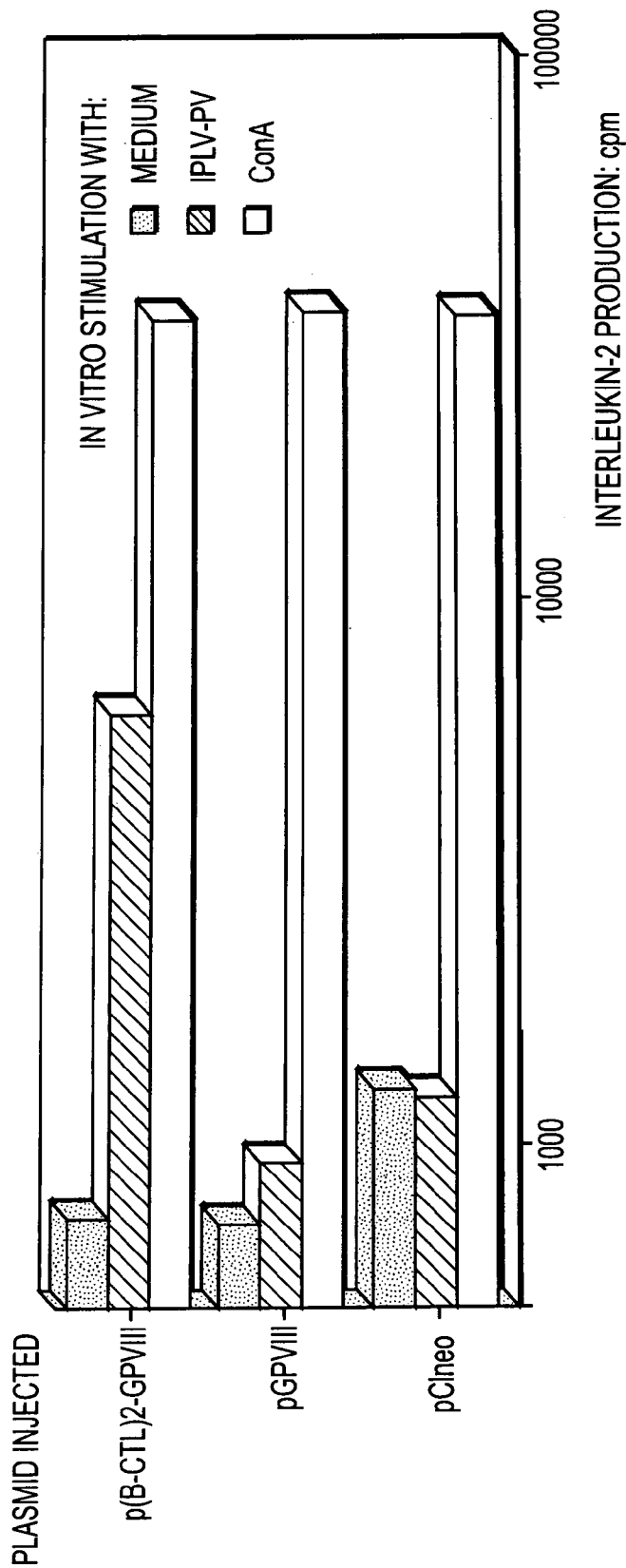

While the pGPVIII gene induced IL-2 producing cells that can be stimulated in vitro by IPRV 21 days after injection, no production was observed after 14 days (FIG. 8A). However, a significant production was observed with pG(B-CTL)$_2$-GPVIII after 14 days (FIG. 8A). This indicates that the fusion of foreign epitopes with GPVIII significantly enhances the production of Th cells directed to site III part of rabies G.

Although pGPVIII induced no anti-rabies antibody in the absence of exogenous IL-2 (FIG. 9), the kinetic study of antibody induced by pG(B-CTL)$_2$-GPVIII showed that significant antibody production occurred against both rabies G and poliovirus peptide (FIG. 9). This also indicates that the fusion of foreign epitopes with GPVIII significantly enhances the production of antibody directed to site III part of rabies PV G. Moreover, the truncated GPVIII was able to carry and to allow the expression of poliovirus B cell epitope in vivo with antibody production.

Production of antibodies induced by p(B-CTL)$_2$-GPVIII against a poliovirus peptide was also tested after priming with either pGPVIII or p(B-CTL)$_2$-GPVIII itself (FIG. 10). When p(B-CTL)$_2$-CPVIII was injected without priming and controlled 13 days (PBS/p(B-CTL)2-GPVIII-D26-) or 39 days after (p(B-CTL)2-GPVIII-D0-), anti-peptide antibody titer was 65 and 80, respectively. However, if a priming was performed with pGPVIII or p(B-CTL)$_2$-GPVIII, the titer was 200 and 600, respectively. This clearly demonstrates that the two types of priming enhanced antibody production against a poliovirus peptide.

Example 7

Immunogenicity of Foreign Epitopes Carried by the Chimeric Glycoprotein

Figure 8B:
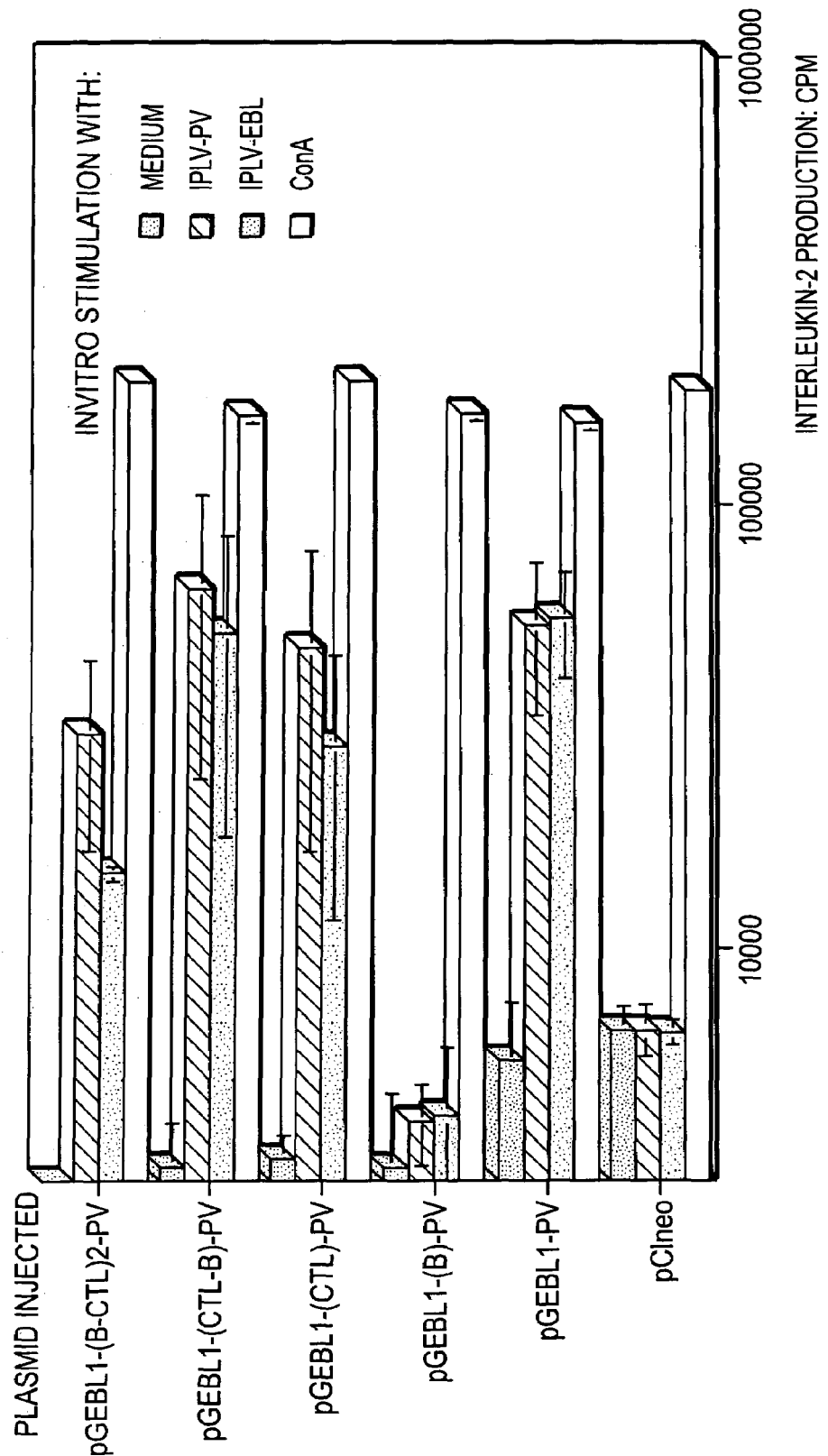

Immunogenicity of both B and CD8 T cell epitopes and the consequence of their insertion on the immunogenicity of the chimeric glycoprotein were analyzed according to humoral and cell mediated immune responses after DNA-based immunization. When epitopes were inserted in the chimeric pGEBL1-PV plasmid, the induction of IL-2-producing cells able to be stimulated by IPLV depended on inserted epitopes. Two types of results were obtained, and are shown in FIG. 8B: i) IL-2 production induced by pGEBL1-(B-CTL)$_2$-PV, pGEBL1-(CTL-B)-PV, and pGEBL1-(CTL)-PV was similar to that induced by pGEBL1-PV; and ii) IL-2 production induced by pGEBL1-(B-CTL)-PV (data not shown) and pGEBL1-(B)-PV was inhibited. Consequently, the chimeric G EBL1-PV can carry foreign B and CD8 T cell epitopes without negative effects on its ability to induce IL-2-producing cells. However, concerning the B cell epitope, a position effect was observed since its insertion immediately behind the EBL1 sequence was deleterious for the induction of T helper cells stimulated by lyssavirus G. However, this phenomenon was not evidenced with pGEBL1-(B-CTL)$_2$-PV.

Insertion of foreign epitopes in pGEBL1-PV was also studied for its consequence on the induction of antibodies against poliovirus peptide and VNAb against both PV and EBL1 lyssaviruses. Table 1 shows antibody production induced by the chimeric pGEBL1-PV plasmid carrying various foreign epitopes. BALB/c mice (three for each plasmid) were injected with 50 µg of various plasmids in each tibialis muscle. Sera were assayed on day 21 for rabies or EBL1 virus neutralizing antibody by the RFFIT method (titer expressed in IU/ml) and for poliovirus anti-peptide antibody by ELISA. Results are expressed as the mean titer, and standard deviation are reported in brackets.

The four plasmids containing the B cell epitope (pGEBL1-(B)-PV, pGEBL1-(CTL-B)-PV, pGEBL1-(B-CTL)$_2$-PV, and pGEBL1-(B-CTL)-PV) induced antibody against the poliovirus peptide. However, when the B cell epitope followed EBL1 sequence (pGEBL1-(B-CTL)-PV and pGEBL1-(B)-PV), antibody production was weaker than when the B epitope was separated by the CD8 cell epitope (pGEBL1-(CTL-B)-PV). The results for pGEBL1-(B-CTL)$_2$-PV were intermediary. The insertion of foreign epitopes induced a decrease of anti-lyssavirus VNAb production but was maintained at a high level when animals were injected with pGEBL1-(CTL)-PV or pGEBL1-(CTL-B)-PV. However, when the B cell epitope was inserted immediately behind the EBL1 sequence, not as great of an anti-lyssavirus VNAb production was observed.

In summary, the chimeric G EBL1-PV can carry and allow the in vivo expression of both poliovirus and lyssavirus neutralizing B cell epitopes but the presence of the poliovirus B cell epitope immediately behind the EBL1 sequence (excepted for (B-CTL)$_2$ insertion) is deleterious for the immunogenicity of both the site II and site III part of the chimeric glycoprotein. On the other hand, when the foreign epitopes are fused with the truncated G PVIII, both T helper and non-neutralizing antibody production can be induced.

ditions, the surviving animals completely eliminated the virus when controlled by RT-PCR 21 days post-infection (data not shown). This indicates that the chimeric G is a very potent carrier of a protective CD8 cell epitope. However, as for anti-lyssavirus and poliovirus immune responses, the insertion of the poliovirus B cell epitope immediately behind the EBL1 sequence induced an inhibition of the protective activity of the following CD8 cell epitope.

TABLE 2

Protection induced by the truncated pGPVIII and the chimeric pGEBL1-PV plasmid encoding the LCMV CD8' epitope.

| Plasm id injected | Survival animals (%) |
| --- | --- |
| pCIneo | 0/10 (0) |
| p(B-CTL)$_2$-GPVIII | 2/5 (40) |
| pGEBL1-(B-CTL)-PV | 0/10 (0) |
| pGEBL1-(CTL-B)-PV | 7/10 (70) |

Example 9

Putative PEST Sequence

Since a deleterious position effect was clearly observed for the position of the insertion of the B cell epitope before or after the CTL cell epitope, the presence of putative PEST sequences in the different plasmids was analyzed (FIG. 1D). Only two plasmids (pGEBL1-(B)-PV and pGEBL1-(B-CTL)$_2$-PV) contained putative PEST sequences due to the junction of the end of EBL1 and the B cell epitope sequences.

TABLE 1

Antibody production induced by the chimeric pGEBL1-PV plasmid carrying various combinations of B and CD8' T cell foreign epitopes.

| | Neutralizing antibody (IU/ml) against: | | Poliovirus anti-peptide antibody |
| --- | --- | --- | --- |
| Plasmid injected | Rabies virus | European Bat Lyssavirus 1 | (Reciprocal dilution) |
| pGEBL1-(B-CTL)$_2$-PV | 0.9 (0.05) | 1.1 (0.07) | 1100 (200) |
| pGEBL1-(CTL-B)-PV | 1.8 (0.2) | 8.0 (1.0) | 1510 (490) |
| pGEBL1-(B-CTL)-PV | 0.06 (0.06) | 0.6 (0.07) | 810 (210) |
| pGEBL1-(CTL)-PV | 2.6 (0.2) | 5.2 (0.2) | 0 (0) |
| pGEBL1-(B)-PV | 0.1 (0.01) | 0.21 (0.09) | 355 (45) |
| pGEBL1-PV | 5.9 (2.1) | 21.9 (1.8) | 0 (0) |
| pCIneo | 0 (0) | 0 (0) | 0 (0) |

Example 8

Protection Against a Lethal Dose of LCMV

As the CD8 T cell epitope is involved in the induction of protection against LCMV, the truncated and chimeric G carrying the LCMV CD8$^+$ T cell epitope were tested for their protective activity. Table 2 shows the protection induced by the chimeric pGEBL1-PV plasmid carrying the LCMV CD8$^+$ epitopes. BALB/c mice (three for each plasmid) were injected with 40 µg of various plasmids and i.c. challenged on day 21. Percentage of surviving animals is reported in brackets.

The truncated p(B-CTL)$_2$-GPVIII induced only a partial protection. When the B and CD8 T cell epitopes were inserted into the chimeric GEBL1-PV, a significant protection was observed with pGEBL1-(CTL-B)-PV against a lethal challenge with LCMV (70% of mice survived). Under these con- However, the substitution of the serine (S) in pGEBL1-(B-CTL)$_2$-PV by a leucine (L) in pGEBL1-(B)-PV reduced the PEST value from +8.38 to +4.20.

Example 10

Dog Immunization and Challenge

Beagle dogs ranging in age from 4 to 8 years were assigned in four experimental groups (Table 3). They were kept in isolated cages and fed with commercial food (400 g each day). They were injected intramuscularly in the thigh with either with 100 µg of plasmid (group A, B, and C) or PBS (group D). Plasmid was injected in one site on day 0, 21, 42, and 175 (group A) or on day 0 and 175 (group C). It was also injected in three sites (3×33 µg) on day 0, 21, 42, and 175 (group B). Blood samples were collected (from veinpuncture) on day 0, 28, 49, 70, 120, 175, and 189.

Lyssavirus neutralizing antibodies were titrated by the rapid fluorescent focus inhibition test (RFFIT) with the previously described modifications using PV, CVS, or FWR viruses. Anti-PV, CVS, or FWR neutralizing antibody titers are expressed in international units per ml (IU/ml) using the 2nd International Standard (Statens Seruminstitut, Copenhagen, Denmark) as the reference or as the reciprocal serum dilution that inhibit 50% of fluorescent focus. Under these conditions, a titer of 40, 70, or 60 (reciprocal serum dilution) was equivalent to 0.5 IU/ml against PV, CVS or FWR respectively.

As shown in FIG. 11, a virus neutralizing antibody (VNAb) can be induced by the plasmid containing the gene encoding the G protein groups (A, B, and C), whereas no antibody was detected in PBS injected animals (group D) whatever the injection protocol. Heightened levels of VNAb were obtained after one injection and a boost on day 21 (group A) or on day 175 (group C). As the seroconversion occurs for 0.5 IU/ml, it was concluded that all animals serconverted.

Moreover, the results presented in FIG. 12 show that all plasmid-injected (vaccinated) dogs were protected against a rabies virus challenge. This is in contrast to the two unvaccinated animals (dogs 11 and 12) that were challenged, but did not survive.

These results are representative and the dosage can be extrapolated to other rabies-susceptible animals, including humans.

TABLE 3

Dog characteristics and injection protocol

| Group | Dog number | Sex* | Age (years) | Product injected | Injection Site number | Day |
|---|---|---|---|---|---|---|
| A | 1 | M | 8 | Plasmid | 1 | 0, 21, 42 and 175 |
|   | 2 | F | 6 | Plasmid | 1 | 0, 21, 42 and 175 |
|   | 3 | F | 6 | Plasmid | 1 | 0, 21, 42 and 175 |
| B | 4 | F | 6 | Plasmid | 3 | 0, 21, 42 and 175 |
|   | 5 | M | 6 | Plasmid | 3 | 0, 21, 42 and 175 |
|   | 6 | F | 8 | Plasmid | 3 | 0, 21, 42 and 175 |
| C | 7 | M | 4 | Plasmid | 1 | 0 and 175 |
|   | 8 | F | 7 | Plasmid | 1 | 0 and 175 |
|   | 9 | F | 4 | Plasmid | 1 | 0 and 175 |
| D | 10** | M | 4 | PBS | 1 | 0, 21, 42 and 175 |
|   | 11 | M | 4 | PBS | 1 | 0, 21, 42 and 175 |
|   | 12 | M | 4 | PBS | 1 | 0, 21, 42 and 175 |

*M: male; F: female
**Discarded on day 160 (sick)

Example 11 pG-PVIII as a Carrier for *Plasmodium* Proteins

Malaria during a woman's first pregnancy results in a high rate of fetal and neonatal death. The decreasing susceptibility during subsequent pregnancies correlates with acquisition of antibodies that block binding of infected red blood cells to chondroitin sulfate A (CSA), a receptor for parasites in the placenta. The inventors have identified a domain within a particular *Plasmodium falciparum* erythrocyte membrane protein-1 (PfEMP-1) that binds CSA (Buffet et al., 1999, "*P. falciparum* domain mediating adhesion to chondroitin sulfate A: A receptor for human placental infection", *PNAS*, 96:12743-48). More specifically, a var gene, which is a *Plasmodium*-derived protein that is expressed in CSA-binding parasitized red blood cells (PRBCs), was cloned. The gene encodes a protein that has eight receptor-like domains. The inventors and their colleagues successfully demonstrated that the Duffy-binding-like (DBL) domain called DBL-3 binds CSA and displays the same binding specificity as PRBCs.

The DBL-3 domain contains a number of cysteines, which seem to be important for the correct folding of the CSA binding region. This folding can, most likely, not be achieved in bacterial expression systems, but can certainly be achieved using a eukaryotic expression system.

A chimeric expression plasmid (DBL-3/PVIII) having 1) a nucleic acid sequence encoding the DBL-3 domain and 2) a nucleic acid sequence encoding the PVIII site was prepared and transfected into $N_2A$ cells. After transfection, washing, and outgrowth of transfected cells in microtiter plate wells, the cells were fixed with 80% acetone for 10 minutes on ice, then subjected to indirect immunofluorescence to determine whether the DBL-3 and/or PVIII epitopes were expressed, and if so, where the encoded epitopes were located within the cells.

FIG. 13 shows that both the DBL-3 domain and the PVIII site were efficiently expressed at the membrane of transfected cells. This result has a great number of implications, not the least of which is that expression of the heterologous *Plasmodium* DBL-3 epitope on the surface of eukaryotic cells using a chimeric nucleic acid carrier molecule of the invention can be accomplished. For example, expression of the DBL-3 epitope from a carrier molecule of the invention can be used to induce immunity that protects a pregnant woman and her fetus from the harmful and potentially deadly effects of malaria.

Example 12

Protection Against Malaria

Because protective antibodies present after pregnancy block binding of parasites from different parts of the world to CSA, pregnant women and their fetuses can be protected via cross-reactivity induced by exposure to DBL-3. Thus, vaccines containing or expressing the DBL-3 domain can be used to immunize women, including pregnant women, especially those women in tropical regions of Africa, Asia, and South and Central America.

Thus, the present invention provides an excellent means to induce antibodies capable of interfering with the CSA binding of infected erythrocytes, thereby protecting women and their fetuses from the harm caused by malaria.

A DNA vaccine is administered to women who are pregnant or who are planning to become pregnant. The DNA vaccine comprises a chimeric nucleic acid carrier molecule, in which an expression vector having a nucleic acid sequence encoding the DBL-3 domain is fused to a nucleic acid sequence encoding the rabies PVIII site. Fusion of the DBL-3 encoding sequences to the rabies glycoprotein PVIII sequences, and expression in the recipient woman, promotes efficient induction of an immune response in the woman against the encoded DBL-3 polypeptide sequence, and protects the woman and her fetus from the harmful effects of malaria.

The invention has been described in detail above with reference to preferred embodiments. However, it will be understood by the ordinary artisan that various modifications and variations can be made in the practice of the present invention without departing from the scope or spirit of the invention. All references cited herein are hereby incorporated by reference in their entirety.

SEQUENCE LISTING

<160> NUMBER OF SEQ ID NOS: 40

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 1
ttctagagcc accatggttc ctcaggctct cctg                             34

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 2
attgatcaac tgaccgggag ggc                                         23

<210> SEQ ID NO 3
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide PVp1

<400> SEQUENCE: 3
aattctagag ccgccaccat ggttcctcag gctctcctgt ttgtacccct tctggttttt    60
ccattgtgtt ttgggaagaa ttcccccccc ggtcagtt                            98

<210> SEQ ID NO 4
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide PVp2

<400> SEQUENCE: 4
gatcaactga ccgggggggg aattcttccc aaaacacaat ggaaaaacca gaaggggtac    60
aaacaggaga gcctgaggaa ccatggtggc ggctctag                            98

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide EBL1p1

<400> SEQUENCE: 5
aatttcccaa tctacaccat cccggataaa atcggaccgt ggtcacctat tccg          54

<210> SEQ ID NO 6
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide EBL1p2

```
<400> SEQUENCE: 6
aattcggaat aggtgaccac ggtccgattt tatccgggat ggtgtagatt ggga          54

<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence: Primer

<400> SEQUENCE: 7
ccgtggtcac ctattgatat aaaccatctc agctgcccaa caacttgat cgtggaagat     60 gag                                                                 63

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 8
ggaattcgag caccattctg gagcttc                                        27

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Asn Pro Ala Ser Thr Thr Asn Lys Asp Lys
  1               5                  10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Gln Ala Ser Gly Val Tyr Met Gly
  1               5

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Arg Pro Gln Ala Ser Gly Val Tyr Met Gly Asn Leu Thr Ala Gln
  1               5                  10                  15

<210> SEQ ID NO 12
<211> LENGTH: 78
<212> TYPE: DNA
<213> ORGANISM: Artificial Sequence
<220> FEATURE:
```

-continued

<223> OTHER INFORMATION: Description of Artificial Sequence: Primer

<400> SEQUENCE: 12
aattcagata acccggcgtc gaccactaac aaggataagc tgttcgcagt gcctcaggcc    60
tctggtgtgt atatgggt    78

<210> SEQ ID NO 13
<211> LENGTH: 78
<212> TYPE: DNA
<213> ORGANISM: Artificial Sequence
<220> FEATURE:
<223> OTHER INFORMATION: Description of Artificial Sequence: Primer

<400> SEQUENCE: 13
aattacccat atacacacca gaggcctgag gcactgcgaa cagcttatcc ttgttagtgg    60
tcgacgccgg gttatctg    78

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      adaptor

<400> SEQUENCE: 14
aatttggata acccggcgtc gaccactaac aa    32

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      adaptor

<400> SEQUENCE: 15
aattcttatc cttgttagtg gtcgacgccg gg    32

<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence: Synthetic
      adaptor

<400> SEQUENCE: 16
aatttggaga gacctcaggc ctctggtgtg tatatgggta atcttacggc ccag    54

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence: Synthetic
      adaptor

<400> SEQUENCE: 17
aattctggga agtaagatta cccatataca caccagaggc ctgaggtctc tcca    54

<210> SEQ ID NO 18
<211> LENGTH: 61
<212> TYPE: PRT
<213> ORGANISM: Artificial Sequence

```
<220> FEATURE:
<223> OTHER INFORMATION: Description of Artificial Sequence: Chimeric
      polypeptide PV-PV

<400> SEQUENCE: 18

Val Leu Gly Leu Arg Leu Met Asp Gly Thr Trp Val Ser Met Gln Thr
 1               5                  10                  15

Ser Asn Glu Thr Lys Trp Cys Pro Gly Gln Leu Ile Asn Leu His
            20                  25                  30

Asp Phe Arg Ser Asp Glu Ile Glu His Leu Val Val Glu Glu Leu Val
        35                  40                  45

Lys Lys Arg Glu Glu Cys Leu Asp Ala Leu Glu Ser Ile
    50                  55                  60

<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence: Chimeric
      polypeptide -PVIII

<400> SEQUENCE: 19

Ser Pro Pro Gly Gln Leu Ile Asn Leu His Asp Phe Arg Ser Asp Glu
 1               5                  10                  15

Ile Glu His Leu Val Val Glu Glu Leu Val Lys Lys Arg Glu Glu Cys
            20                  25                  30

Leu Asp Ala Leu Glu Ser Ile
        35

<210> SEQ ID NO 20
<211> LENGTH: 64
<212> TYPE: PRT
<213> ORGANISM: Artificial Sequence
<220> FEATURE:
<223> OTHER INFORMATION: Description of Artificial Sequence: Chimeric
      polypeptide EBL1-PV

<400> SEQUENCE: 20

Val Pro Gly Met Arg Leu Met Asp Gly Ser Trp Val Ser Leu Gln Lys
 1               5                  10                  15

Thr Glu Ala Pro Glu Trp Cys Ser Asn Ser Pro Pro Gly Gln Leu Ile
            20                  25                  30

Asn Leu His Asp Phe Arg Ser Asp Glu Ile Glu His Leu Val Val Glu
        35                  40                  45

Glu Leu Val Lys Lys Arg Glu Glu Cys Leu Asp Ala Leu Glu Ser Ile
    50                  55                  60

<210> SEQ ID NO 21
<211> LENGTH: 61
<212> TYPE: PRT
<213> ORGANISM: Artificial Sequence
<220> FEATURE:
<223> OTHER INFORMATION: Description of Artificial Sequence: Chimeric
      polypeptide Mok-PV

<400> SEQUENCE: 21

Arg Pro Gly Ile Arg Leu Phe Asp Gly Thr Trp Val Ser Phe Thr Lys
 1               5                  10                  15

Pro Asp Val His Val Trp Cys Thr Pro Asn Gln Leu Ile Asn Leu His
            20                  25                  30

Asp Phe Arg Ser Asp Glu Ile Glu His Leu Val Val Glu Glu Leu Val
```

35                  40                  45

Lys Lys Arg Glu Glu Cys Leu Asp Ala Leu Glu Ser Ile
        50                  55                  60

<210> SEQ ID NO 22
<211> LENGTH: 61
<212> TYPE: PRT
<213> ORGANISM: Artificial Sequence
<220> FEATURE:
<223> OTHER INFORMATION: Description of Artificial Sequence: Chimeric
      polypeptide PV-Mok

<400> SEQUENCE: 22

Val Leu Gly Leu Arg Leu Met Asp Gly Thr Trp Val Ser Met Gln Thr
 1               5                  10                  15

Ser Asn Glu Thr Lys Trp Cys Pro Pro Gly Gln Leu Ile Asn Ile His
            20                  25                  30

Asn Asp Arg Leu Asp Glu Ile Glu His Leu Ile Val Glu Asp Ile Ile
        35                  40                  45

Lys Lys Arg Glu Glu Cys Leu Asp Thr Leu Glu Thr Ile
    50                  55                  60

<210> SEQ ID NO 23
<211> LENGTH: 61
<212> TYPE: PRT
<213> ORGANISM: Artificial Sequence
<220> FEATURE:
<223> OTHER INFORMATION: Description of Artificial Sequence: Chimeric
      polypeptide Mok-Sad

<400> SEQUENCE: 23

Lys Pro Gly Ile Arg Leu Phe Asp Gly Thr Trp Val Ser Phe Thr Lys
 1               5                  10                  15

Pro Asp Glu Thr Lys Trp Cys Pro Pro Asp Lys Leu Val Asn Leu His
            20                  25                  30

Asp Phe Arg Ser Asp Glu Ile Glu His Leu Val Val Glu Glu Leu Val
        35                  40                  45

Arg Lys Arg Glu Glu Cys Leu Asp Ala Leu Glu Ser Ile
    50                  55                  60

<210> SEQ ID NO 24
<211> LENGTH: 524
<212> TYPE: PRT
<213> ORGANISM: Lyssavirus sp.
<220> FEATURE:
<223> OTHER INFORMATION: PV

<400> SEQUENCE: 24

Met Val Pro Gln Ala Leu Leu Phe Val Pro Leu Leu Val Phe Pro Leu
 1               5                  10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Ser Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

-continued

```
Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
            115                 120                 125

Glu Ser Leu His Asn Pro Tyr Pro Asp Tyr His Trp Leu Arg Thr Val
            130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Gly Gly
                165                 170                 175

Asn Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
            195                 200                 205

Asp Ile Phe Thr Asn Ser Arg Gly Lys Arg Ala Ser Lys Gly Ser Glu
            210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Gly Gln Leu Val Asn Leu His Asp Phe Arg Ser Asp Glu Ile Glu
            275                 280                 285

His Leu Val Val Glu Glu Leu Val Lys Lys Arg Glu Glu Cys Leu Asp
            290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Arg Val Gly Gly
            355                 360                 365

Arg Cys His Pro His Val Asn Gly Val Phe Phe Asn Gly Ile Ile Leu
            370                 375                 380

Gly Pro Asp Gly Asn Val Leu Ile Pro Glu Met Gln Ser Ser Leu Leu
385                 390                 395                 400

Gln Gln His Met Glu Leu Leu Val Ser Ser Val Ile Pro Leu Met His
                405                 410                 415

Pro Leu Ala Asp Pro Ser Thr Val Phe Lys Asn Gly Asp Glu Ala Glu
            420                 425                 430

Asp Phe Val Glu Val His Leu Pro Asp Val His Glu Arg Ile Ser Gly
            435                 440                 445

Val Asp Leu Gly Leu Pro Asn Trp Gly Lys Tyr Val Leu Leu Ser Ala
            450                 455                 460

Gly Ala Leu Thr Ala Leu Met Leu Ile Ile Phe Leu Met Thr Cys Trp
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser Tyr Lys Ser Gly Gly Glu Thr Gly Leu
```

```
                515                 520

<210> SEQ ID NO 25
<211> LENGTH: 524
<212> TYPE: PRT
<213> ORGANISM: Lyssavirus sp.
<220> FEATURE:
<223> OTHER INFORMATION: USA7-BT

<400> SEQUENCE: 25

Met Ile Pro Gln Ala Leu Leu Phe Val Pro Leu Leu Ile Pro

-continued

```
                355                 360                 365
Lys Cys His Pro Pro Val Asn Gly Val Phe Phe Asn Gly Ile Ile Leu
        370                 375                 380
Gly Pro Asp Gly Asn Val Leu Ile Pro Glu Met Gln Ser Ser Leu Leu
385                 390                 395                 400
Gln Gln His Met Glu Leu Leu Glu Ser Ser Val Ile Pro Leu Met His
                405                 410                 415
Pro Leu Ala Asp Pro Ser Thr Val Phe Lys Glu Gly Asp Glu Ala Glu
                420                 425                 430
Asp Phe Val Glu Val His Leu Pro Asp Val His Lys Arg Ile Ser Gly
            435                 440                 445
Val Asp Leu Gly Leu Pro Ser Trp Gly Lys Tyr Leu Leu Met Ser Ala
        450                 455                 460
Gly Ala Leu Ala Ile Leu Ile Leu Ala Ile Val Leu Ile Ile Cys Cys
465                 470                 475                 480
Arg Arg Val Asn Lys Thr Gly Ser Thr Gln Arg Gly His Arg Glu Ser
                485                 490                 495
Arg Gly Lys Met Ser Val Ala Pro Gln Asn Gly Lys Ile Ile Ser Ser
                500                 505                 510
Trp Glu Leu Tyr Lys Arg Glu Ser Glu Thr Gly Leu
            515                 520

<210> SEQ ID NO 26
<211> LENGTH: 525
<212> TYPE: PRT
<213> ORGANISM: Lyssavirus sp.
<220> FEATURE:
<223> OTHER INFORMATION: PL

<400> SEQUENCE: 26

Met Leu Leu Gln Ile Val Leu Leu Met Ser Leu Met Val Phe Ser Pro
1               5                   10                  15
Cys Pro Gly Lys Phe Pro Leu Tyr Thr Ile Pro Asp Lys Leu Gly Pro
                20                  25                  30
Trp Ser Pro Ile Asp Ile His His Leu Ser Cys Pro Asn Asn Leu Ile
            35                  40                  45
Val Glu Asp Glu Gly Cys Thr Ser Leu Ser Gly Phe Ser Tyr Met Glu
        50                  55                  60
Leu Lys Val Gly Phe Ile Thr Thr Ile Lys Val Ser Gly Phe Thr Cys
65                  70                  75                  80
Thr Gly Val Val Thr Glu Ser Glu Thr Tyr Thr Asn Phe Phe Gly Tyr
                85                  90                  95
Val Thr Thr Thr Phe Lys Arg Lys His Phe Arg Pro Thr Pro Glu Phe
                100                 105                 110
Cys Arg Asn Ala Tyr Asn Trp Lys Val Ala Gly Asp Pro Arg Tyr Glu
            115                 120                 125
Glu Ser Leu His Asn Pro Tyr Pro Asp Tyr His Trp Leu Arg Thr Val
        130                 135                 140
Thr Thr Thr Lys Glu Ser Leu Leu Ile Ile Ser Pro Ser Val Val Asp
145                 150                 155                 160
Met Asp Pro Tyr Asp Lys Ser Leu His Ser Lys Met Phe Pro Lys Gly
                165                 170                 175
Thr Cys Ser Gly Ala Ser Val Pro Ser Ile Phe Cys Ser Thr Asn His
                180                 185                 190
Asp Tyr Thr Leu Trp Met Pro Glu Asn Pro Lys Pro Gly Met Ser Cys
```

```
                195                 200                 205
Asp Ile Phe Thr Thr Ser Lys Gly Lys Lys Ala Ser Lys Gly Gly Lys
    210                 215                 220

Val Cys Gly Phe Val Asp Glu Arg Gly Leu Tyr Lys Ser Leu Lys Gly
225                 230                 235                 240

Ala Cys Lys Leu Lys Leu Cys Gly Ile Ser Gly Leu Arg Leu Met Asp
                245                 250                 255

Gly Ser Trp Val Ser Ile Gln Asn His Glu Ala Lys Trp Cys Ser
                260                 265                 270

Pro Asp Gln Leu Val Asn Ile His Asp Phe His Ser Asp Glu Ile Glu
                275                 280                 285

His Leu Ile Val Glu Glu Leu Val Arg Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Val Asn Lys Thr Leu Met Glu Ala Asp Ala His Tyr Asn Gln Val Arg
                340                 345                 350

Thr Trp Asn Glu Ile Ile Pro Ser Lys Gly Cys Leu Lys Val Arg Glu
            355                 360                 365

Arg Cys His Pro Pro Tyr Asn Gly Val Phe Phe Asn Gly Ile Ile Leu
    370                 375                 380

Ser Pro Asp Gly His Val Leu Ile Pro Glu Met Gln Ser Ser Leu Leu
385                 390                 395                 400

Gln Gln His Ile Glu Leu Leu Glu Ser Ser Val Ile Pro Leu Ile His
                405                 410                 415

Pro Leu Ala Asp Pro Ser Thr Val Phe Tyr Arg Asp Asp Glu Ala Glu
                420                 425                 430

Asp Phe Ile Glu Val His Leu Pro Asp Val Gln Lys Gln Val Ser Gly
            435                 440                 445

Ile Asp Leu Gly Leu Ser Glu Trp Glu Arg Tyr Leu Ile Ile Gly Ala
    450                 455                 460

Ser Ala Val Ile Leu Phe Ala Leu Ala Ile Ile Phe Ala Val Cys Cys
465                 470                 475                 480

Arg Arg Cys Lys Arg Arg Lys Lys Ala Arg Thr Asp Arg Ile Glu Leu
                485                 490                 495

Asp Arg Lys Val Ser Val Thr Ser Gln Ser Gly Lys Val Ile Pro Ser
                500                 505                 510

Trp Glu Ser Tyr Lys Leu Pro Lys Ser His Phe Arg Ser
            515                 520                 525

<210> SEQ ID NO 27
<211> LENGTH: 524
<212> TYPE: PRT
<213> ORGANISM: Lyssavirus sp.
<220> FEATURE:
<223> OTHER INFORMATION: EBL1POL

<400> SEQUENCE: 27

Met Leu Leu Ser Thr Ala Ile Phe Ala Phe Phe Leu Asn Cys Ala Pro
1               5                   10                  15

Cys Leu Ala Lys Phe Pro Ile Tyr Thr Ile Pro Asp Lys Ile Gly Pro
                20                  25                  30

Trp Ser Pro Ile Asp Ile Asn His Leu Ser Cys Pro Asn Asn Leu Ile
```

```
                    35                  40                  45
Val Glu Asp Glu Gly Cys Thr Thr Leu Thr Pro Phe Ser Tyr Met Glu
     50                  55                  60

Leu Lys Val Gly Tyr Ile Thr Thr Ile Ile Glu Ser Gly Phe Thr Cys
 65                  70                  75                  80

Thr Gly Val Ile Thr Glu Ala Glu Thr Tyr Thr Asn Phe Val Gly Tyr
                     85                  90                  95

Val Thr Thr Thr Phe Lys Arg Lys His Phe Arg Pro Thr Val Ser Ala
                100                 105                 110

Cys Arg Asp Ala Tyr Asn Trp Lys Ile Thr Gly Asp Pro Arg Tyr Glu
                115                 120                 125

Glu Ser Leu His Asn Pro Tyr Pro Asp Ser His Trp Leu Arg Thr Val
            130                 135                 140

Lys Thr Thr Lys Glu Ser Leu Leu Ile Ile Ser Pro Ser Val Val Asp
145                 150                 155                 160

Met Asp Ala Tyr Asp Lys Asn Leu Tyr Ser Lys Met Phe Pro Asn Gly
                165                 170                 175

Lys Cys Leu Ala Ser Pro Ser Ala Ile Cys Cys Pro Thr Asn His
            180                 185                 190

Asp Tyr Thr Ile Trp Ile Pro Glu Asn Pro Lys Pro Gly Leu Ser Cys
                195                 200                 205

Asp Ile Phe Thr Thr Ser Lys Gly Lys Lys Ala Thr Lys Asp Gly Arg
            210                 215                 220

Leu Cys Gly Phe Val Asp Glu Arg Gly Leu Tyr Lys Ser Leu Lys Gly
225                 230                 235                 240

Ala Cys Lys Leu Arg Leu Cys Gly Val Pro Gly Met Arg Leu Met Asp
                245                 250                 255

Gly Ser Trp Val Ser Leu Gln Lys Thr Glu Ala Pro Glu Trp Cys Ser
                260                 265                 270

Pro Asp Gln Leu Val Asn Val His Asp Phe His Thr Asp Glu Ile Glu
            275                 280                 285

His Leu Val Val Glu Glu Leu Val Lys Lys Arg Glu Glu Cys Leu Asp
        290                 295                 300

Ala Leu Glu Thr Ile Ile Thr Thr Lys Ser Ile Ser Phe Arg Arg Leu
305                 310                 315                 320

Ser His Phe Arg Lys Leu Val Pro Gly Phe Gly Lys Ala Tyr Thr Leu
                325                 330                 335

Ile Asn Lys Thr Leu Met Glu Ala Asp Ala His Tyr Lys Ser Val Arg
            340                 345                 350

Glu Trp Lys Glu Val Ile Pro Ser Lys Gly Cys Leu Met Ala Gly Gly
            355                 360                 365

Arg Cys His Pro His Tyr Ser Gly Ile Phe Phe Asn Gly Ile Ile Leu
        370                 375                 380

Ser Pro Gly Gly Asp Val Leu Ile Pro Glu Met Gln Ser Ala Leu Leu
385                 390                 395                 400

Gln Gln His Ile Glu Leu Leu Glu Ser Ser Met Ile Pro Leu Arg His
                405                 410                 415

Pro Leu Ala Asp Pro Ser Thr Val Phe Arg Lys Asp Glu Ala Glu
            420                 425                 430

Asp Phe Val Glu Val His Leu Pro Asp Thr Gln Lys Leu Ile Ser Gly
        435                 440                 445

Ile Asp Leu Gly Phe Pro Glu Trp Lys Arg Tyr Phe Leu Ile Gly Ile
450                 455                 460
```

```
Ser Val Leu Ala Leu Leu Ala Leu Ala Ile Ile Thr Ala Ala Cys Cys
465                 470                 475                 480

Lys Arg Phe Lys Arg Arg Arg Pro Lys Pro Asn Pro Ile Glu Leu
            485                 490                 495

Ile Arg Lys Val Ser Val Thr Ser Gln Ser Gly Arg Ala Ile Pro Ser
                500                 505                 510

Trp Glu Ser Tyr Lys Val Gly Pro Pro Gly Glu Ser
            515                 520

<210> SEQ ID NO 28
<211> LENGTH: 524
<212> TYPE: PRT
<213> ORGANISM: Lyssavirus sp.
<220> FEATURE:
<223> OTHER INFORMATION: EBL1FRA

<400> SEQUENCE: 28

Met Leu Leu Ser Thr Ala

```
Ala Leu Glu Thr Ile Ile Thr Thr Lys Ser Ile Ser Phe Arg Arg Leu
305                 310                 315                 320

Ser His Phe Arg Lys Leu Val Pro Gly Phe Gly Lys Ala Tyr Thr Leu
                325                 330                 335

Ile Asn Lys Thr Leu Met Glu Ala Asp Ala His Tyr Lys Ser Val Arg
            340                 345                 350

Glu Trp Thr Glu Val Ile Pro Ser Lys Gly Cys Leu Met Ala Gly Gly
        355                 360                 365

Arg Cys His Pro His Tyr Ser Gly Ile Phe Phe Asn Gly Ile Ile Leu
    370                 375                 380

Ser Pro Gly Gly Asp Val Leu Ile Pro Glu Met Gln Ser Ala Leu Leu
385                 390                 395                 400

Gln Gln His Ile Glu Leu Leu Glu Ser Ser Met Ile Pro Leu Arg His
                405                 410                 415

Pro Leu Ala Asp Pro Ser Thr Val Phe Lys Arg Asp Asp Glu Ala Glu
                420                 425                 430

Asp Phe Val Glu Val His Leu Pro Asp Thr Gln Lys Leu Ile Ser Gly
            435                 440                 445

Ile Asp Leu Gly Phe Pro Glu Trp Lys Arg Tyr Phe Leu Ile Gly Ile
        450                 455                 460

Ser Val Leu Ala Leu Leu Ala Leu Ala Ile Ile Thr Ala Ala Cys Cys
465                 470                 475                 480

Lys Arg Phe Lys Arg Arg Arg Pro Lys Pro Asn Pro Ile Glu Leu
                485                 490                 495

Ile Arg Lys Val Ser Val Thr Ser Gln Ser Gly Arg Ala Ile Pro Ser
                500                 505                 510

Trp Glu Ser Tyr Lys Val Gly Thr Ser Glu Ser
                515                 520

<210> SEQ ID NO 29
<211> LENGTH: 524
<212> TYPE: PRT
<213> ORGANISM: Lyssavirus sp.
<220> FEATURE:
<223> OTHER INFORMATION: EBL2FIN

<400> SEQUENCE: 29

Met Pro Phe Gln Thr Val Leu Ser Ala Leu Leu

```
Thr Thr Thr Lys Glu Ser Leu Leu Ile Ile Ser Pro Ser Val Val Asn
145                 150                 155                 160

Met Asp Ala Tyr Asp Lys Thr Leu Tyr Ser Lys Ile Phe Leu Asn Gly
                165                 170                 175

Lys Cys Ser Gly Val Ser Gln Val Ser Pro Phe Cys Ser Thr Asn His
            180                 185                 190

Asp Tyr Thr Ile Trp Met Pro Glu Asn Pro Asn Pro Gly Val Ser Cys
        195                 200                 205

Asp Ile Phe Thr Thr Ser Lys Gly Lys Ala Thr Lys Asp Gly Lys
    210                 215                 220

Leu Cys Gly Phe Val Asp Glu Arg Gly Leu Tyr Lys Ser Leu Lys Gly
225                 230                 235                 240

Ala Cys Lys Leu Lys Leu Cys Gly Ile Ser Gly Met Arg Leu Met Asp
                245                 250                 255

Gly Ser Trp Val Ser Ile Gln Asn His Asp Glu Ala Lys Trp Cys Ser
                260                 265                 270

Pro Asp Gln Leu Val Asn Ile His Asp Phe His Ser Asp Glu Val Glu
            275                 280                 285

His Leu Ile Ala Glu Glu Leu Val Lys Lys Arg Glu Glu Cys Leu Asp
        290                 295                 300

Ala Leu Glu Ser Ile Met Thr Thr Lys Ser Ile Ser Phe Arg Arg Leu
305                 310                 315                 320

Ser His Leu Arg Lys Leu Val Pro Gly Phe Gly Lys Ala Tyr Thr Ile
                325                 330                 335

Ile Asn Lys Thr Leu Met Glu Ala Asp Ala His Tyr Lys Ser Ile Arg
                340                 345                 350

Glu Trp Thr Asp Val Ile Pro Ser Lys Gly Cys Leu Met Ala Gly Gly
            355                 360                 365

Arg Cys Tyr Pro His His Asn Gly Val Phe Phe Asn Gly Ile Ile Leu
370                 375                 380

Ser Pro Asp Gly His Val Leu Ile Pro Glu Met Gln Ser Ala Met Leu
385                 390                 395                 400

Gln Gln His Ile Glu Leu Leu Glu Ser Ser Val Ile Pro Leu Met His
                405                 410                 415

Pro Leu Ala Asp Pro Ser Thr Ile Phe Lys Lys Asp Asp Gly Ala Glu
            420                 425                 430

Asp Phe Val Glu Val His Leu Pro Asp Val Gln Lys Gln Ile Ser Gly
            435                 440                 445

Ile Asp Leu Gly Leu Pro Glu Trp Lys Arg Tyr Phe Leu Ile Gly Val
    450                 455                 460

Ser Ala Leu Ala Leu Leu Ala Leu Met Ile Phe Ile Ala Ala Cys Cys
465                 470                 475                 480

Lys Arg Val Lys His Lys Lys Arg Ala Lys Pro Asn Pro Val Glu Leu
                485                 490                 495

Ile Arg Lys Val Ser Val Thr Ser Gln Ser Gly Arg Pro Ile Pro Ser
                500                 505                 510

Trp Glu Ser Tyr Lys Val Glu Thr Gly Gly Gln Ser
                515                 520

<210> SEQ ID NO 30
<211> LENGTH: 524
<212> TYPE: PRT
<213> ORGANISM: Lyssavirus sp.
<220> FEATURE:
```

<223> OTHER INFORMATION: EBL2HOL

<400> SEQUENCE: 30

```
Met Pro Phe Gln Ala Val Leu Ser Ala Leu Leu Ser Ala Leu Thr Leu
 1               5                  10                  15

Cys Val Gly Lys Phe Pro Ile Tyr Thr Ile Pro Asp Lys Leu Gly Pro
             20                  25                  30

Trp Ser Pro Ile Asp Ile His His Leu Ser Cys Pro Thr Asn Met Val
         35                  40                  45

Val Glu Asp Glu Gly Cys Thr Thr Leu Thr Val Phe Ser Tyr Met Glu
     50                  55                  60

Leu Lys Val Gly Tyr Ile Thr Thr Ile Lys Val Asn Glu Phe Thr Cys
 65                  70                  75                  80

Thr Gly Val Val Thr Glu Ala Glu Thr Tyr Thr Asn Phe Val Gly Tyr
                 85                  90                  95

Val Thr Thr Thr Phe Lys Arg Lys Asp Phe Arg Pro Ser Pro Ser Ala
            100                 105                 110

Cys Arg Asp Ala Tyr Ser Cys Lys Thr Ala Gly Asp Pro Arg Tyr Glu
        115                 120                 125

Glu Ser Leu His Asn Pro Tyr Pro Asp Ser His Trp Leu Thr Cys Thr
    130                 135                 140

Thr Thr Thr Lys Glu Ser Val Leu Ile Ile Ser Pro Ser Val Ala Asp
145                 150                 155                 160

Met Asp Ala Tyr Asp Lys Thr Leu Tyr Ser Lys Ile Phe Leu Asn Gly
                165                 170                 175

Lys Cys Ser Gly Val Ser Gln Val Ser Pro Phe Cys Ser Thr Asn His
            180                 185                 190

Asp Tyr Thr Ile Trp Met Pro Glu Asn Pro Asn Pro Gly Val Ser Cys
        195                 200                 205

Asp Ile Phe Thr Thr Ser Lys Gly Lys Ala Thr Lys Asp Gly Lys
    210                 215                 220

Leu Cys Gly Phe Val Asp Glu Arg Gly Leu Tyr Lys Ser Leu Lys Gly
225                 230                 235                 240

Ala Cys Lys Leu Lys Leu Cys Gly Ile Ser Gly Met Arg Leu Met Asp
                245                 250                 255

Gly Ser Trp Val Ser Ile Gln Asn His Asp Glu Ala Lys Trp Cys Ser
            260                 265                 270

Pro Asp Gln Leu Val Asn Ile His Asp Phe His Ser Asp Glu Val Glu
        275                 280                 285

His Leu Ile Ala Glu Glu Leu Val Lys Lys Arg Glu Glu Cys Leu Asp
    290                 295                 300

Ala Leu Glu Ser Ile Met Thr Thr Lys Ser Ile Ser Phe Arg Arg Leu
305                 310                 315                 320

Ser His Leu Arg Lys Leu Val Pro Gly Phe Gly Lys Ala Tyr Thr Val
                325                 330                 335

Ile Asn Lys Thr Leu Met Glu Ala Asp Ala His Tyr Lys Ser Ile Arg
            340                 345                 350

Glu Trp Thr Asp Val Ile Pro Ser Lys Gly Cys Leu Met Ala Gly Gly
        355                 360                 365

Arg Cys Tyr Pro His His Asn Gly Val Phe Phe Asn Gly Ile Ile Leu
    370                 375                 380

Ser Pro Asp Gly His Val Leu Ile Pro Glu Met Gln Ser Ala Met Leu
385                 390                 395                 400
```

```
Gln Gln His Ile Glu Leu Leu Glu Ser Ser Val Ile Pro Leu Met His
            405                 410                 415

Pro Leu Ala Asp Pro Ser Thr Ile Phe Lys Lys Asp Gly Ala Glu
        420                 425                 430

Asp Phe Val Glu Val His Leu Pro Asp Val Gln Lys Gln Ile Ser Gly
                435                 440                 445

Ile Asp Leu Gly Leu Pro Glu Trp Lys Arg Tyr Phe Leu Ile Gly Val
    450                 455                 460

Ser Ala Leu Ala Phe Leu Ala Leu Met Ile Phe Ile Ala Ala Cys Cys
465                 470                 475                 480

Arg Arg Val Lys Arg Lys Arg Ala Lys Pro Asn Pro Val Glu Leu
                485                 490                 495

Ile Arg Lys Val Ser Val Thr Ser Gln Ser Gly Arg Pro Ile Pro Ser
                500                 505                 510

Trp Glu Ser Tyr Lys Val Glu Thr Gly Gly Gln Ser
            515                 520

<210> SEQ ID NO 31
<211> LENGTH: 533
<212> TYPE: PRT
<213> ORGANISM: Lyssavirus sp.
<220> FEATURE:
<223> OTHER INFORMATION: Duv1SAF

<400> SEQUENCE: 31

Met Pro Leu Asn Ala Val Ile Phe Thr Leu Leu Leu Arg Cys Ser Ile
 1               5                  10                  15

Cys Leu Gly Lys Phe Pro Phe Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Thr Leu Thr Pro Phe Ser Tyr Met Glu
    50                  55                  60

Leu Lys Val Gly Tyr Ile Thr Ser Ile Lys Val Ser Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Arg Arg Arg His Phe Arg Pro Ser Val Asn Ser
            100                 105                 110

Cys Arg Asp Ala Tyr Asn Trp Lys Ile Ala Gly Asp Pro Arg Tyr Glu
        115                 120                 125

Glu Ser Leu His Asn Pro Tyr Pro Asp Ser His Trp Leu Arg Thr Val
    130                 135                 140

Lys Thr Thr Lys Glu Ser Leu Leu Ile Ile Ser Pro Ser Val Ala Asp
145                 150                 155                 160

Met Asp Ala Tyr Asp Lys Lys Leu Tyr Ser Lys Met Phe Pro Asn Gly
                165                 170                 175

Arg Cys Ser Glu Ile Ser Pro Gly Ser Pro Phe Cys Pro Thr Asn His
            180                 185                 190

Glu Tyr Thr Ile Trp Met Pro Glu Ser Ser Asn Pro Gly Ile Ser Cys
        195                 200                 205

Asp Ile Phe Thr Arg Ser Met Gly Lys Lys Ala Thr Lys Asp Gly Gln
    210                 215                 220

Leu Cys Gly Phe Val Asp Glu Arg Gly Leu Tyr Lys Ser Leu Lys Gly
225                 230                 235                 240
```

```
Ala Cys Arg Leu Arg Leu Cys Gly Ile Ser Gly Leu Arg Leu Met Asp
                245                 250                 255

Gly Ser Trp Val Ser Leu Pro Gln Val Asn Asn Ser Glu Trp Cys Ser
            260                 265                 270

Pro Asp Gln Leu Val Asn Ile His Asp Phe His Ser Asp Glu Ile Glu
        275                 280                 285

His Leu Val Ala Asp Glu Leu Val Lys Lys Arg Glu Asp Cys Leu Asp
    290                 295                 300

Ala Leu Glu Thr Ile Ile Phe Thr Lys Ser Ile Ser Phe Arg Arg Leu
305                 310                 315                 320

Ser Arg Leu Arg Lys Leu Val Pro Gly Phe Gly Lys Ala Tyr Thr Ile
                325                 330                 335

Ile Asn Arg Thr Leu Met Glu Ala Glu Ala His Tyr Lys Ser Val Arg
            340                 345                 350

Glu Trp Lys Glu Ile Ile Pro Ser Lys Gly Cys Leu Lys Ala Gly Gly
        355                 360                 365

Arg Cys Tyr Pro His His Asn Ile Val Phe Phe Asn Gly Ile Ile Leu
    370                 375                 380

Gly Pro Gly Gly Lys Ile Leu Ile Pro Glu Met Gln Ser Ala Leu Leu
385                 390                 395                 400

Gln Gln His Ile Glu Leu Leu Glu Ser Ser Val Val Pro Leu Lys His
                405                 410                 415

Pro Leu Ala Asp Pro Ser Thr Val Phe Lys Asn Asp Asp Glu Ala Glu
            420                 425                 430

Ser Phe Val Asp Val His Leu Pro Asp Thr Asn Gln Lys Ile Ser Gly
        435                 440                 445

Ile Asp Leu Gly Leu Pro Glu Trp Lys Arg Tyr Phe Leu Ile Gly Val
    450                 455                 460

Ser Ala Val Ala Leu Leu Ala Leu Ser Ile Ile Met Arg Val Cys Cys
465                 470                 475                 480

Lys Arg Phe Lys Asn Arg Arg Lys Ser Lys Pro Ser Pro Val Glu Leu
                485                 490                 495

Thr Arg Lys Val Ser Val Ile Ser Lys Gly Asn Gly Pro Val Pro Ser
            500                 505                 510

Trp Glu Ser Tyr Lys Glu Gly Thr Thr Gly Asp Val Arg Asn Thr Thr
        515                 520                 525

Pro Ser Thr Arg Glu
    530

<210> SEQ ID NO 32
<211> LENGTH: 533
<212> TYPE: PRT
<213> ORGANISM: Lyssavirus sp.
<220> FEATURE:
<223> OTHER INFORMATION: Duv2SAF

<400> SEQUENCE: 32

Met Pro Leu Asn Ala Val Ile Phe Thr Leu Leu Leu Arg Cys Ser Ile
1               5                   10                  15

Cys Leu Gly Lys Phe Pro Phe Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Thr Leu Thr Pro Phe Ser Tyr Met Glu
    50                  55                  60
```

```
Leu Lys Val Gly Tyr Ile Thr Ser Ile Lys Val Ser Gly Phe Thr Cys
 65                  70                  75                  80

Thr Gly Val Val Thr Glu Ala Glu Thr Tyr Thr Asn Phe Val Gly Tyr
                 85                  90                  95

Val Thr Thr Thr Phe Arg Arg Arg His Phe Arg Pro Ser Val Asn Ser
            100                 105                 110

Cys Arg Asp Ala Tyr Asn Trp Lys Ile Ala Gly Asp Pro Arg Tyr Glu
            115                 120                 125

Glu Ser Leu His Asn Pro Tyr Pro Asp Ser His Trp Leu Arg Thr Val
            130                 135                 140

Lys Thr Thr Lys Glu Ser Leu Leu Ile Ile Ser Pro Ser Val Ala Asp
145                 150                 155                 160

Met Asp Ala Tyr Asp Lys Lys Leu Tyr Ser Lys Met Phe Pro Asn Gly
                165                 170                 175

Arg Cys Ser Glu Ile Ser Pro Gly Ser Pro Phe Cys Pro Thr Asn His
            180                 185                 190

Glu Tyr Thr Ile Trp Met Pro Glu Ser Ser Asn Pro Gly Ile Ser Cys
            195                 200                 205

Asp Ile Phe Thr Arg Ser Met Gly Lys Lys Ala Thr Lys Asp Gly Gln
210                 215                 220

Leu Cys Gly Phe Val Asp Glu Arg Gly Leu Tyr Lys Ser Leu Lys Gly
225                 230                 235                 240

Ala Cys Arg Leu Arg Leu Cys Gly Ile Ser Gly Leu Arg Leu Met Asp
                245                 250                 255

Gly Ser Trp Val Ser Leu Pro Gln Val Asn Asn Ser Glu Trp Cys Ser
            260                 265                 270

Pro Asp Gln Leu Val Asn Ile His Asp Phe His Ser Asp Glu Ile Glu
            275                 280                 285

His Leu Val Ala Asp Glu Leu Val Lys Lys Arg Glu Asp Cys Leu Asp
            290                 295                 300

Ala Leu Glu Thr Ile Leu Phe Thr Lys Ser Ile Ser Phe Arg Arg Leu
305                 310                 315                 320

Ser His Leu Arg Lys Leu Val Pro Gly Phe Gly Lys Ala Tyr Thr Ile
                325                 330                 335

Ile Asn Arg Thr Leu Met Glu Ala Glu Ala His Tyr Lys Ser Val Arg
            340                 345                 350

Glu Trp Lys Glu Ile Ile Pro Ser Lys Gly Cys Leu Lys Ala Gly Gly
            355                 360                 365

Arg Cys Tyr Pro His His Asn Gly Ile Phe Phe Asn Gly Ile Ile Leu
            370                 375                 380

Gly Pro Gly Gly Glu Ile Leu Ile Pro Glu Met Gln Ser Ala Leu Leu
385                 390                 395                 400

Gln Gln His Ile Glu Leu Leu Glu Ser Ser Val Val Pro Leu Lys His
                405                 410                 415

Pro Leu Ala Asp Pro Ser Thr Val Phe Lys Asn Asp Asp Glu Ala Glu
            420                 425                 430

Ser Phe Val Asp Val His Leu Pro Asp Thr Asn Gln Lys Ile Ser Gly
            435                 440                 445

Ile Asp Leu Gly Leu Pro Glu Trp Lys Arg Tyr Phe Leu Ile Gly Val
450                 455                 460

Ser Ala Val Ala Leu Leu Ala Leu Ser Ile Ile Ile Ala Val Cys Cys
465                 470                 475                 480

Lys Arg Phe Arg Lys Arg Lys Lys Ser Lys Pro Gly Pro Val Glu Leu
```

```
                         485                 490                 495
Thr Arg Lys Val Ser Val Ile Ser Lys Gly Asn Gly Pro Val Pro Ser
                 500                 505                 510

Trp Glu Ser Tyr Lys Glu Gly Thr Thr Gly Asp Val Arg Asn Thr Thr
                 515                 520                 525

Pro Ser Thr Arg Glu
        530

<210> SEQ ID NO 33
<211> LENGTH: 522
<212> TYPE: PRT
<213> ORGANISM: Lyssavirus sp.
<220> FEATURE:
<223>

```
                305                 310                 315                 320
Ser His Phe Arg Lys Leu Val Pro Gly Tyr Gly Lys Ala Tyr Thr Ile
            325                 330                 335

Leu Asn Gly Ser Leu Ile Gln Thr Asn Val His Tyr Leu Lys Val Asp
            340                 345                 350

Asn Trp Ser Glu Ile Leu Pro Ser Lys Gly Cys Leu Lys Ile Asn Asn
            355                 360                 365

Gln Cys Val Ala His Asp Glu Gly Val Phe Phe Asn Gly Ile Ile Lys
            370                 375                 380

Gly Pro Asp Gly His Ile Leu Ile Pro Glu Met Gln Ser Ser Leu Trp
385                 390                 395                 400

Lys Gln His Met Asp Leu Phe Lys Ala Ala Val Phe Pro Leu Arg His
            405                 410                 415

Pro Leu Ile Glu Pro Gly Ser Leu Phe Asn Lys Asp Gly Asp Ala Asp
            420                 425                 430

Glu Phe Val Asp Val His Met Pro Asp Val His Lys Leu Val Ser Asp
            435                 440                 445

Val Asp Leu Gly Leu Pro Asp Trp Ser Leu Tyr Ala Leu Ile Gly Ala
450                 455                 460

Thr Ile Ile Ala Phe Phe Ile Leu Ile Cys Leu Ile Arg Ile Cys Cys
465                 470                 475                 480

Lys Lys Arg Gly Arg Arg Asn Ser Pro Thr Asn Arg Pro Asp Leu Pro
            485                 490                 495

Ile Gly Leu Ser Thr Thr Pro Gln Pro Lys Ser Lys Val Ile Ser Ser
            500                 505                 510

Trp Glu Ser Tyr Lys Gly Thr Ser Asn Val
            515                 520

<210> SEQ ID NO 34
<211> LENGTH: 522
<212> TYPE: PRT
<213> ORGANISM: Lyssavirus sp.
<220> FEATURE:
<223> OTHER INFORMATION: Lag2CAR

<400> SEQUENCE: 34

Met Ser Gln Leu Ile Leu Ile Pro Phe Leu Cys Val Val Ile Val Ile
1               5                   10                  15

Ser Val Gly Asp Phe Pro Leu Tyr Thr Ile Pro Glu Lys Ile Gly Thr
            20                  25                  30

Trp Thr Pro Ile Asp Leu Ile His Leu Ser Cys Pro Asn Asn Leu Leu
        35                  40                  45

Ser Glu Asp Asp Gly Cys Ser Asn Thr Ala Thr Phe Asn Tyr Ile Glu
    50                  55                  60

Leu Lys Thr Gly Tyr Leu Thr His Gln Lys Val Ser Gly Phe Thr Cys
65                  70                  75                  80

Thr Gly Val Val Asn Glu Ala Val Tyr Thr Asn Phe Val Gly Tyr
            85                  90                  95

Val Thr Thr Thr Phe Lys Arg Lys His Phe Lys Pro Thr Ala Leu Ala
            100                 105                 110

Cys Arg Asp Ala Phe His Trp Lys Ile Ser Gly Asp Pro Arg Tyr Glu
            115                 120                 125

Glu Ser Leu His Thr Pro Tyr Pro Asp Asn Ser Trp Leu Arg Thr Val
            130                 135                 140

Thr Thr Thr Lys Glu Ser Leu Leu Ile Ile Ser Pro Ser Ile Val Glu
```

```
                145                 150                 155                 160
Met Asp Val Tyr Ser Arg Thr Leu His Ser Pro Met Phe Pro Gly Gly
                    165                 170                 175
Val Cys Ser Lys Phe Tyr Pro Ser Ser Pro Ser Cys Pro Thr Asn His
            180                 185                 190
Asp Tyr Thr Leu Trp Leu Pro Glu Asp Ala Asn Leu Ser Met Ala Cys
        195                 200                 205
Asp Ile Phe Ile Thr Ser Thr Gly Lys Lys Ser Met Asn Gly Ser Arg
    210                 215                 220
Met Cys Gly Phe Thr Asp Glu Arg Gly Phe Tyr Arg Thr Leu Lys Gly
225                 230                 235                 240
Ala Cys Lys Leu Thr Leu Cys Gly Lys Pro Gly Leu Arg Leu Tyr Asp
                245                 250                 255
Gly Thr Trp Val Ser Phe Thr Arg Pro Glu Ile Asn Val Trp Cys Ser
                    260                 265                 270
Pro Asn Gln Leu Val Asn Val His Asn Asn Arg Leu Asp Glu Ile Glu
            275                 280                 285
His Leu Ile Val Gly Asp Leu Ile Arg Lys Arg Glu Glu Cys Leu Asp
        290                 295                 300
Thr Leu Glu Thr Ile Leu Met Ser Lys Ser Ile Ser Phe Arg Arg Leu
305                 310                 315                 320
Ser His Phe Arg Lys Leu Val Pro Gly Tyr Gly Lys Ala Tyr Thr Ile
                325                 330                 335
Ile Asn Gly Ser Leu Met Glu Thr Asn Val His Tyr Leu Arg Val Asp
                340                 345                 350
Ser Trp Asn Asp Ile Leu Pro Ser Lys Gly Cys Leu Lys Met Asn Lys
            355                 360                 365
Gln Cys Val Asp Ser Tyr Arg Gly Val Phe Phe Asn Gly Ile Ile Lys
        370                 375                 380
Gly His Asp Gly His Ile Leu Ile Pro Glu Met Gln Ser Ser Leu Leu
385                 390                 395                 400
Lys Gln His Met Asp Leu Leu Lys Ala Ala Val Phe Pro Leu Arg His
                405                 410                 415
Pro Leu Ile Asp Gln Asn Ser Leu Phe Lys Lys Asp Gly Asp Ala Asp
                    420                 425                 430
Asp Phe Val Glu Val His Met Pro Asp Ile Gln Lys Leu Ile Ser Asp
            435                 440                 445
Val Asp Leu Gly Leu Pro Ser Trp Gly Leu Tyr Val Met Ile Gly Ala
        450                 455                 460
Ala Val Ile Ala Phe Leu Val Leu Ile Cys Leu Ile Arg Ile Cys Cys
465                 470                 475                 480
Lys Lys Lys Thr Arg Thr Arg Thr Ser Met Glu Arg Pro Asp Pro Pro
                485                 490                 495
Ile Ser Leu Ser Thr Thr Pro Gln Ser Arg Ala Lys Val Val Ser Ser
                500                 505                 510
Trp Glu Ser Tyr Lys Gly Ser Ser Asn Val
                515                 520

<210> SEQ ID NO 35
<211> LENGTH: 523
<212> TYPE: PRT
<213> ORGANISM: Lyssavirus sp.
<220> FEATURE:
<223> OTHER INFORMATION: Mok3ETP
```

<400> SEQUENCE: 35

| | | | | | | | | | | | | | | |
|---|---|---|---|---|---|---|---|---|---|---|---|---|---|---|
| Met | Asn | Ile | Pro | Cys | Phe | Ala | Val | Ile | Leu | Ser | Leu | Ala | Thr | Thr | His |
| 1 | | | | 5 | | | | | 10 | | | | | 15 | |

Cys Leu Glu Lys Phe Leu Ile Tyr Thr Ile Pro Glu Lys Ile Glu Lys
              20                  25                    30

Trp Thr Pro Ile Asp Met Ile His Leu Ser Cys Pro Asn Asn Met Leu
        35                  40                    45

Ser Glu Glu Gly Cys Asn Thr Glu Ser Pro Phe Thr Tyr Phe Glu
      50                55                60

Leu Lys Ser Gly Tyr Leu Ala His Gln Lys Val Pro Gly Phe Thr Cys
65                  70                  75                80

Thr Gly Val Val Asn Glu Ala Glu Thr Tyr Thr Asn Phe Val Gly Tyr
              85                  90                95

Val Thr Thr Thr Phe Lys Arg Lys His Phe Lys Pro Thr Val Ala Ala
            100               105              110

Cys Arg Asp Ala Tyr Asn Trp Lys Val Ser Gly Asp Pro Arg Tyr Glu
            115               120              125

Glu Ser Leu His Thr Pro Tyr Pro Asp Ser Ser Trp Leu Arg Thr Val
     130                135              140

Thr Thr Thr Lys Glu Ala Leu Leu Ile Ile Ser Pro Ile Val Glu Asp
145                150               155              160

Met Ile Ala Gly Arg Lys Thr Leu His Ser Pro Met Phe Pro Ser Gly
            165               170              175

Lys Cys Ser Lys Leu Tyr Pro Ser Val Pro Ser Cys Thr Thr Asn His
            180             185              190

Asp Tyr Thr Leu Trp Leu Pro Glu Asp Ser Ser Leu Ser Leu Ile Cys
        195              200              205

Asp Ile Phe Thr Ser Ser Gly Gln Lys Ala Met Asn Gly Ser Arg
    210                215              220

Ile Cys Gly Phe Lys Asp Glu Arg Gly Phe Tyr Arg Ser Leu Lys Gly
225                230               235              240

Ser Cys Lys Leu Thr Leu Cys Gly Lys Pro Gly Ile Arg Leu Phe Asp
            245             250              255

Gly Thr Trp Val Ser Phe Thr Lys Pro Asp Val His Val Trp Cys Thr
          260               265              270

Pro Asn Gln Leu Val Asn Ile His Asn Asp Arg Leu Asp Glu Val Glu
        275              280             285

His Leu Ile Val Asp Asp Ile Ile Lys Lys Arg Glu Glu Cys Leu Asp
    290                295              300

Thr Leu Glu Thr Ile Leu Met Ser Gln Ser Val Ser Phe Arg Arg Leu
305                310               315              320

Ser His Phe Arg Lys Leu Val Pro Gly Tyr Gly Lys Ala Tyr Thr Ile
            325             330              335

Leu Asn Gly Ser Leu Met Glu Thr Asn Val Tyr Tyr Lys Arg Val Asp
            340             345              350

Arg Trp Ala Asp Ile Leu Pro Ser Arg Gly Cys Leu Lys Val Gly Gln
            355             360              365

Gln Cys Met Asp Pro Val Lys Asn Leu Val Phe Phe Asn Gly Ile Ile
        370              375              380

Lys Gly Pro Asp Gly Gln Ile Leu Ile Pro Glu Met Gln Ser Glu Gln
385                390               395              400

Leu Lys Gln His Met Asp Leu Leu Lys Ala Ala Met Phe Pro Leu Arg
            405             410              415

His Pro Leu Ile Asn Arg Glu Ala Val Phe Lys Lys Asp Gly Asn Ala
              420                 425                 430

Asp Asp Phe Val Asp Leu His Met Pro Asp Val Gln Lys Ser Val Ser
          435                 440                 445

Asp Val Asp Leu Gly Leu Pro His Trp Gly Phe Trp Leu Leu Val Gly
    450                 455                 460

Ala Thr Val Val Ala Phe Val Leu Ala Cys Leu Arg Val Cys
465                 470                 475                 480

Cys Arg Arg Met Arg Arg Arg Ser Leu Arg Ala Thr Gln Asp Ile
                485                 490                 495

Pro Leu Ser Val Ala Pro Ala Pro Val Pro Arg Ala Lys Val Val Ser
          500                 505                 510

Ser Trp Glu Ser Ser Lys Gly Leu Pro Gly Thr
          515                 520

<210> SEQ ID NO 36
<211> LENGTH: 523
<212> TYPE: PRT
<213> ORGANISM: Lyssavirus sp.
<220> FEATURE:
<223> OTHER INFORMATION: Mok2ZIM

<400> SEQUENCE: 36

Met Asn Ile Pro Cys Phe Val Val Ile Leu Ser Leu Ala Thr Thr His
1               5                   10                  15

Ser Leu Gly Glu Phe Pro Leu Tyr Thr Ile Pro Glu Lys Ile Glu Lys
            20                  25                  30

Trp Thr Pro Ile Asp Met Ile His Leu Ser Cys Pro Asn Asn Leu Leu
        35                  40                  45

Ser Glu Glu Glu Gly Cys Asn Ala Glu Ser Ser Phe Thr Tyr Phe Glu
    50                  55                  60

Leu Lys Ser Gly Tyr Leu Ala His Gln Lys Val Pro Gly Phe Thr Cys
65                  70                  75                  80

Thr Gly Val Val Asn Glu Ala Glu Thr Tyr Thr Asn Phe Val Gly Tyr
                85                  90                  95

Val Thr Thr Thr Phe Lys Arg Lys His Phe Arg Pro Thr Val Ala Ala
            100                 105                 110

Cys Arg Asp Ala Tyr Asn Trp Lys Val Ser Gly Asp Pro Arg Tyr Glu
        115                 120                 125

Glu Ser Leu His Thr Pro Tyr Pro Asp Ser Ser Trp Leu Arg Thr Val
    130                 135                 140

Thr Thr Thr Lys Glu Ser Leu Leu Ile Ile Ser Pro Ser Ile Val Glu
145                 150                 155                 160

Met Asp Ile Tyr Gly Arg Thr Leu His Ser Pro Met Phe Pro Ser Gly
                165                 170                 175

Val Cys Ser Asn Val Tyr Pro Ser Val Pro Ser Cys Glu Thr Asn His
            180                 185                 190

Asp Tyr Thr Leu Trp Leu Pro Glu Asp Pro Ser Leu Ser Leu Val Cys
        195                 200                 205

Asp Ile Phe Thr Ser Ser Asn Gly Lys Lys Ala Met Asn Gly Ser Arg
    210                 215                 220

Ile Cys Gly Phe Lys Asp Glu Arg Gly Phe Tyr Arg Ser Leu Lys Gly
225                 230                 235                 240

Ala Cys Lys Leu Thr Leu Cys Gly Arg Pro Gly Ile Arg Leu Phe Asp
                245                 250                 255

```
Gly Thr Trp Val Ser Phe Thr Lys Pro Asp Val His Val Lys Thr Cys
            260                 265                 270

Asn Pro Asp Ile Leu Val Asn Ile His Asn Asp Arg Leu Asp Glu Ile
        275                 280                 285

Glu His Leu Ile Val Glu Asp Ile Ile Lys Lys Arg Glu Glu Cys Leu
    290                 295                 300

Asp Thr Leu Glu Thr Ile Leu Met Ser Gln Ser Val Ser Phe Arg Arg
305                 310                 315                 320

Leu Ser His Phe Arg Lys Leu Val Pro Gly Tyr Gly Lys Ala Tyr Thr
                325                 330                 335

Ile Leu Asn Gly Ser Leu Met Glu Thr Asn Val Tyr Tyr Lys Arg Val
            340                 345                 350

Asp Lys Trp Ala Asp Ile Leu Pro Ser Lys Gly Cys Leu Lys Val Gly
        355                 360                 365

Gln Gln Cys Met Glu Pro Val Lys Gly Val Leu Phe Asn Gly Ile Ile
    370                 375                 380

Lys Gly Pro Asp Gly Gln Ile Leu Ile Pro Glu Met Gln Ser Glu Gln
385                 390                 395                 400

Leu Lys Gln His Met Asp Leu Leu Lys Ala Ala Val Phe Pro Leu Arg
                405                 410                 415

His Pro Leu Ile Ser Arg Glu Ala Val Phe Lys Lys Asp Gly Asp Ala
            420                 425                 430

Asp Asp Phe Val Asp Leu His Met Pro Asp Val His Lys Ser Val Ser
        435                 440                 445

Asp Val Asp Leu Gly Leu Pro His Trp Gly Phe Trp Met Leu Ile Gly
    450                 455                 460

Ala Thr Ile Val Ala Phe Val Val Leu Val Cys Leu Leu Arg Val Cys
465                 470                 475                 480

Cys Lys Arg Val Arg Arg Arg Ser Gly Arg Ala Thr Gln Glu Ile
                485                 490                 495

Pro Leu Ser Phe Pro Ser Ala Pro Val Pro Arg Ala Lys Val Val Ser
            500                 505                 510

Ser Trp Glu Ser Tyr Lys Gly Leu Pro Gly Thr
        515                 520

<210> SEQ ID NO 37
<211> LENGTH: 129
<212> TYPE: PRT
<213> ORGANISM: Lyssavirus sp.
<220> FEATURE

```
Ser Leu Leu Lys Gln His Met Asp Leu Leu Lys Ala Ala Val Phe Pro
            100                 105                 110
Leu Arg His Pro Leu Ile Asp Gln Asn Ser Leu Phe Lys Lys Asp Gly
        115                 120                 125
Asp

<210> SEQ ID NO 38
<211> LENGTH: 129
<212> TYPE: PRT
<213> ORGANISM: Lyssavirus sp.
<220> FEATURE:
<223> OTHER INFORMATION: Lag4SAF

<400> SEQUENCE: 38

Cys Leu Asp Thr Leu Glu Thr Ile Leu Met Ser Lys Ser Ile Ser Phe
  1               5                  10                  15
Arg Arg Leu Ser His Phe Arg Lys Leu Val Pro Gly T

Asp

```
<210> SEQ ID NO 40
<211> LENGTH: 522
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (2)
<223> OTHER INFORMATION: variable amino acid
<220> FEATURE:
<221> NAME/KEY: MOD_RES
<222> LOCATION: (9)
<223> OTHER INFORMATION: variable amino acid
<220> FEATURE:
<221> NAME/KEY: MOD_RES
<222> LOCATION: (13)..(15)
<223> OTHER INFORMATION: variable amino acid
<220> FEATURE:
<221> NAME/KEY: MOD_RES
<222> LOCATION: (58)
<223> OTHER INFORMATION: variable amino acid
<220> FEATURE:
<221> NAME/KEY: MOD_RES
<222> LOCATION: (111)
<223> OTHER INFORMATION: variable amino acid
<220> FEATURE:
<221> NAME/KEY: MOD_RES
<222> LOCATION: (181)
<223> OTHER INFORMATION: variable amino acid
<220> FEATURE:
<221> NAME/KEY: MOD_RES
<222> LOCATION: (189)
<223> OTHER INFORMATION: variable amino acid
<220> FEATURE:
<221> NAME/KEY: MOD_RES
<222> LOCATION: (262)
<223> OTHER INFORMATION: variable amino acid
<220> FEATURE:
<221> NAME/KEY: MOD_RES
<222> LOCATION: (264)..(265)
<223> OTHER INFORMATION: variable amino acid
<220> FEATURE:
<221> NAME/KEY: MOD_RES
<222> LOCATION: (267)..(268)
<223> OTHER INFORMATION: variable amino acid
<220> FEATURE:
<221> NAME/KEY: MOD_RES
<222> LOCATION: (310)
<223> OTHER INFORMATION: variable amino acid
<220> FEATURE:
<221> NAME/KEY: MOD_RES
<222> LOCATION: (355)
<223> OTHER INFORMATION: variable amino acid
<220> FEATURE:
<221> NAME/KEY: MOD_RES
<222> LOCATION: (374)
<223> OTHER INFORMATION: variable amino acid
<220> FEATURE:
<221> NAME/KEY: MOD_RES
<222> LOCATION: (445)
<223> OTHER INFORMATION: variable amino acid
<220> FEATURE:
<221> NAME/KEY: MOD_RES
<222> LOCATION: (488)..(489)
<223> OTHER INFORMATION: variable amino acid
<220> FEATURE:
<221> NAME/KEY: MOD_RES
<222> LOCATION: (494)
<223> OTHER INFORMATION: variable amino acid
<220> FEATURE:
<221> NAME/KEY: MOD_RES
<222> LOCATION: (518)
<223> OTHER INFORMATION: variable amino acid
<220> FEATURE:
```

-continued

```
<221> NAME/KEY: MOD_RES
<222> LOCATION: (521)
<223> OTHER INFORMATION: variable amino acid

<400> SEQUENCE: 40
```

| | | | | | | | | | | | | | | |
|---|---|---|---|---|---|---|---|---|---|---|---|---|---|---|
| Met | Xaa | Leu | Gln | Ala | Val | Ile | Phe | Xaa | Leu | Leu | Leu | Xaa | Xaa | Xaa | Leu |
| 1 | | | | 5 | | | | | 10 | | | | | 15 | |
| Cys | Leu | Gly | Lys | Phe | Pro | Ile | Tyr | Thr | Ile | Pro | Asp | Lys | Leu | Gly | Pro |
| | | | 20 | | | | | 25 | | | | | 30 | | |
| Trp | Ser | Pro | Ile | Asp | Ile | His | His | Leu | Ser | Cys | Pro | Asn | Asn | Leu | Val |
| | | 35 | | | | | 40 | | | | | 45 | | | |
| Val | Glu | Asp | Glu | Gly | Cys | Thr | Thr | Leu | Xaa | Pro | Phe | Ser | Tyr | Met | Glu |
| 50 | | | | | | 55 | | | | | 60 | | | | |
| Leu | Lys | Val | Gly | Tyr | Ile | Thr | Thr | Ile | Lys | Val | Ser | Gly | Phe | Thr | Cys |
| 65 | | | | | 70 | | | | | 75 | | | | | 80 |
| Thr | Gly | Val | Val | Thr | Glu | Ala | Glu | Thr | Tyr | Thr | Asn | Phe | Val | Gly | Tyr |
| | | | | 85 | | | | | 90 | | | | | 95 | |
| Val | Thr | Thr | Thr | Phe | Lys | Arg | Lys | His | Phe | Arg | Pro | Thr | Val | Xaa | Ala |
| | | | 100 | | | | | 105 | | | | | 110 | | |
| Cys | Arg | Asp | Ala | Tyr | Asn | Trp | Lys | Ile | Ala | Gly | Asp | Pro | Arg | Tyr | Glu |
| | | 115 | | | | | 120 | | | | | 125 | | | |
| Glu | Ser | Leu | His | Asn | Pro | Tyr | Pro | Asp | Ser | His | Trp | Leu | Arg | Thr | Val |
| | 130 | | | | | 135 | | | | | 140 | | | | |
| Thr | Thr | Thr | Lys | Glu | Ser | Leu | Leu | Ile | Ile | Ser | Pro | Ser | Val | Val | Asp |
| 145 | | | | | 150 | | | | | 155 | | | | | 160 |
| Met | Asp | Ala | Tyr | Asp | Lys | Thr | Leu | His | Ser | Lys | Met | Phe | Pro | Asn | Gly |
| | | | | 165 | | | | | 170 | | | | | 175 | |
| Lys | Cys | Ser | Gly | Xaa | Ser | Pro | Ser | Ser | Pro | Phe | Cys | Xaa | Thr | Asn | His |
| | | | 180 | | | | | 185 | | | | | 190 | | |
| Asp | Tyr | Thr | Ile | Trp | Met | Pro | Glu | Asn | Pro | Asn | Pro | Gly | Leu | Ser | Cys |
| | | 195 | | | | | 200 | | | | | 205 | | | |
| Asp | Ile | Phe | Thr | Thr | Ser | Lys | Gly | Lys | Lys | Ala | Thr | Lys | Gly | Gly | Arg |
| | 210 | | | | | 215 | | | | | 220 | | | | |
| Leu | Cys | Gly | Phe | Val | Asp | Glu | Arg | Gly | Leu | Tyr | Lys | Ser | Leu | Lys | Gly |
| 225 | | | | | 230 | | | | | 235 | | | | | 240 |
| Ala | Cys | Lys | Leu | Lys | Leu | Cys | Gly | Ile | Pro | Gly | Leu | Arg | Leu | Met | Asp |
| | | | | 245 | | | | | 250 | | | | | 255 | |
| Gly | Ser | Trp | Val | Ser | Xaa | Gln | Xaa | Xaa | Glu | Xaa | Xaa | Lys | Trp | Cys | Ser |
| | | | 260 | | | | | 265 | | | | | 270 | | |
| Pro | Asp | Gln | Leu | Val | Asn | Ile | His | Asp | Phe | His | Ser | Asp | Glu | Ile | Glu |
| | | 275 | | | | | 280 | | | | | 285 | | | |
| His | Leu | Ile | Val | Glu | Glu | Leu | Val | Lys | Lys | Arg | Glu | Glu | Cys | Leu | Asp |
| | 290 | | | | | 295 | | | | | 300 | | | | |
| Ala | Leu | Glu | Thr | Ile | Xaa | Thr | Thr | Lys | Ser | Ile | Ser | Phe | Arg | Arg | Leu |
| 305 | | | | | 310 | | | | | 315 | | | | | 320 |
| Ser | His | Leu | Arg | Lys | Leu | Val | Pro | Gly | Phe | Gly | Lys | Ala | Tyr | Thr | Ile |
| | | | | 325 | | | | | 330 | | | | | 335 | |
| Ile | Asn | Lys | Thr | Leu | Met | Glu | Ala | Asp | Ala | His | Tyr | Lys | Ser | Val | Arg |
| | | | 340 | | | | | 345 | | | | | 350 | | |
| Glu | Trp | Xaa | Glu | Ile | Ile | Pro | Ser | Lys | Gly | Cys | Leu | Lys | Ala | Gly | Gly |
| | | 355 | | | | | 360 | | | | | 365 | | | |
| Arg | Cys | His | Pro | His | Xaa | Asn | Gly | Val | Phe | Phe | Asn | Gly | Ile | Ile | Leu |
| | 370 | | | | | 375 | | | | | 380 | | | | |
| Gly | Pro | Asp | Gly | His | Val | Leu | Ile | Pro | Glu | Met | Gln | Ser | Ala | Leu | Leu |

```
                                   -continued
385                 390                 395                 400

Gln Gln His Ile Glu Leu Leu Glu Ser Ser Val Ile Pro Leu Arg His
                405                 410                 415

Pro Leu Ala Asp Pro Ser Thr Val Phe Lys Lys Asp Asp Glu Ala Glu
                420                 425                 430

Asp Phe Val Glu Val His Leu Pro Asp Val Gln Lys Xaa Ile Ser Gly
            435                 440                 445

Ile Asp Leu Gly Leu Pro Glu Trp Lys Arg Tyr Phe Leu Ile Gly Ala
        450                 455                 460

Ser Ala Leu Ala Leu Leu Ala Leu Ala Ile Ile Ile Ala Val Cys Cys
465                 470                 475                 480

Lys Arg Val Lys Arg Arg Arg Xaa Xaa Lys Pro Asn Pro Xaa Glu Leu
                485                 490                 495

Ile Arg Lys Val Ser Val Thr Ser Gln Ser Gly Lys Val Ile Pro Ser
                500                 505                 510

Trp Glu Ser Tyr Lys Xaa Gly Thr Xaa Gly
            515                 520
```

What is claimed is:

1. An isolated chimeric lyssavirus glycoprotein encoded by a recombinant polynucleotide, wherein said recombinant polynucleotide comprises:
   a) a polynucleotide encoding the site III polypeptide of the glycoprotein from genotype GT1 lyssavirus, wherein said polynucleotide does not encode the entire lyssavirus glycoprotein of said virus, and
   b) a polynucleotide encoding the site II polypeptide sequence of the glycoprotein from genotype GT5 lyssavirus, wherein said polynucleotide further comprises a polynucleoticle encoding the transmembrane domain and the cytoplasmic domain of the glycoprotein of said genotype GT1 lyssavirus.

2. An immunogenic composition comprising the chimeric lyssavirus glycoprotein of claim 1 and at least one of an adjuvant, excipient, stabilizer, or antigen.

3. The immunogenic composition of claim 2, wherein said composition induces humoral and cellular immunity.

4. The immunogenic composition of claim 2, wherein said immunogenic composition induces a protective immune response.

5. The isolated chimeric lyssavirus glycoprotein of claim 1, wherein said glycoprotein further comprises a heterologous peptide, polypeptide, or protein other than a lyssavirus glycoprotein or a peptide or polypeptide fragment of a lyssavirus glycoprotein.

6. The isolated chimeric lyssavirus glycoprotein of claim 5, wherein the heterologous peptide, polypeptide, or protein is a B cell epitope, a CD8 cell epitope, or both.

* * * * *

UNITED STATES PATENT AND TRADEMARK OFFICE
CERTIFICATE OF CORRECTION

| | | |
|---|---|---|
| PATENT NO. | : 7,645,455 B2 | Page 1 of 1 |
| APPLICATION NO. | : 11/723761 | |
| DATED | : January 12, 2010 | |
| INVENTOR(S) | : Jacob et al. | |

It is certified that error appears in the above-identified patent and that said Letters Patent is hereby corrected as shown below:

Title page, item (75), line 3 under "Inventors," "Bards (TN)" should read --Bardo (TN)--.

Signed and Sealed this

Sixteenth Day of March, 2010

David J. Kappos
*Director of the United States Patent and Trademark Office*